United States Patent
Takahashi et al.

(10) Patent No.: US 9,283,561 B2
(45) Date of Patent: Mar. 15, 2016

(54) LIQUID CHANNEL DEVICE AND PRODUCTION METHOD THEREFOR

(71) Applicant: Fujikura Kasei Co., Ltd., Tokyo (JP)

(72) Inventors: Shigeru Takahashi, Kuki (JP); Masaaki Sakurai, Kuki (JP); Jiro Wakamatsu, Kuki (JP)

(73) Assignee: Fujikura Kasei Co., Ltd., Tokyo (JP)

( * ) Notice: Subject to any disclaimer, the term of this patent is extended or adjusted under 35 U.S.C. 154(b) by 247 days.

(21) Appl. No.: 13/934,310

(22) Filed: Jul. 3, 2013

(65) Prior Publication Data

US 2013/0294980 A1 Nov. 7, 2013

Related U.S. Application Data

(62) Division of application No. 12/739,325, filed as application No. PCT/JP2009/005711 on Oct. 28, 2009, now Pat. No. 8,499,794.

(30) Foreign Application Priority Data

| Oct. 28, 2008 | (JP) | 2008-276468 |
| Aug. 25, 2009 | (JP) | 2009-194590 |
| Aug. 25, 2009 | (JP) | 2009-194591 |
| Aug. 25, 2009 | (JP) | 2009-194592 |

(51) Int. Cl.
*B01J 19/00* (2006.01)
*B01L 3/00* (2006.01)
(Continued)

(52) U.S. Cl.
CPC ............... *B01L 3/56* (2013.01); *B01J 19/0093* (2013.01); *B01L 3/50273* (2013.01);
(Continued)

(58) Field of Classification Search
CPC ............... B01L 3/56; B01L 3/502738; B01L 3/502707; B01L 3/50273; F16K 99/003; F16K 99/0001; B01J 19/0093; G01N 35/00029
USPC .................................. 251/61.1; 422/502, 537
See application file for complete search history.

(56) References Cited

U.S. PATENT DOCUMENTS

| 5,932,799 A | 8/1999 | Moles |
| 6,610,253 B2 | 8/2003 | Kennedy et al. |

(Continued)

FOREIGN PATENT DOCUMENTS

| DE | 102006053452 A1 | 5/2008 |
| JP | 05005741 A | 1/1993 |

(Continued)

OTHER PUBLICATIONS

Search Report issued in International Patent Application No. PCT/JP2009/005711; Jan. 26, 2010; Japanese Patent Office.
(Continued)

*Primary Examiner* — Mary McManmon
*Assistant Examiner* — Nicole Wentlandt
(74) *Attorney, Agent, or Firm* — Wood, Herron & Evans, LLP

(57) ABSTRACT

The present invention relates to a liquid channel device capable of easily opening the liquid channel from the closed mode, including a base plate in which a liquid channel, through which a liquid containing at least one of a sample and a reagent, flows, and a metering chamber for holding the liquid, are formed to at least one side thereof, the metering chamber has a liquid transport section for transporting the liquid inside the chamber downstream, and this liquid transport section is operated by means of external pressing on a cover plate in the area opposite the metering chamber.

3 Claims, 33 Drawing Sheets

(51) Int. Cl.
*F16K 99/00* (2006.01)
*G01N 35/00* (2006.01)
*G01N 35/08* (2006.01)

(52) U.S. Cl.
CPC .... *B01L 3/502707* (2013.01); *B01L 3/502738* (2013.01); *F16K 99/0001* (2013.01); *F16K 99/003* (2013.01); *G01N 35/00029* (2013.01); *B01J 2219/00889* (2013.01); *B01J 2219/00891* (2013.01); *B01L 2300/0803* (2013.01); *B01L 2300/0816* (2013.01); *B01L 2300/0867* (2013.01); *B01L 2300/0887* (2013.01); *B01L 2400/0409* (2013.01); *B01L 2400/0481* (2013.01); *B01L 2400/0605* (2013.01); *B01L 2400/0655* (2013.01); *B01L 2400/0677* (2013.01); *F16K 2099/008* (2013.01); *F16K 2099/0084* (2013.01); *G01N 35/00069* (2013.01); *G01N 35/08* (2013.01); *G01N 2035/00495* (2013.01); *Y10T 137/0491* (2015.04); *Y10T 137/2202* (2015.04); *Y10T 137/2224* (2015.04); *Y10T 137/8811* (2015.04); *Y10T 156/10* (2015.01); *Y10T 156/1002* (2015.01)

(56) References Cited

U.S. PATENT DOCUMENTS

| | | | |
|---|---|---|---|
| 6,877,528 | B2 | 4/2005 | Gilbert et al. |
| 7,198,759 | B2 * | 4/2007 | Bryning et al. ............... 422/504 |
| 2005/0153430 | A1 | 7/2005 | Ohtaka |
| 2005/0266582 | A1 * | 12/2005 | Modlin et al. ............... 436/164 |
| 2006/0215155 | A1 | 9/2006 | Weber |
| 2007/0231216 | A1 | 10/2007 | Park et al. |

FOREIGN PATENT DOCUMENTS

| | | |
|---|---|---|
| JP | 05005741 B2 | 1/1993 |
| JP | 05119318 A | 5/1993 |
| JP | 2001510275 A | 7/2001 |
| JP | 2002505439 A | 2/2002 |
| JP | 2002066999 A | 3/2002 |
| JP | 2002282682 A | 10/2002 |
| JP | 2003107094 A | 4/2003 |
| JP | 2003287479 A | 10/2003 |
| JP | 2004516127 A | 6/2004 |
| JP | 2004291187 A | 10/2004 |
| JP | 2005017057 A | 1/2005 |
| JP | 2005031064 A | 2/2005 |
| JP | 2005176836 A | 7/2005 |
| JP | 2005283331 A | 10/2005 |
| JP | 2005534044 A | 11/2005 |
| JP | 2005535859 A | 11/2005 |
| JP | 2006058112 A | 3/2006 |
| JP | 2006078225 A | 3/2006 |
| JP | 2006136990 A | 6/2006 |
| JP | 2006187730 A | 7/2006 |
| JP | 2006283965 A | 10/2006 |
| JP | 2006329767 A | 12/2006 |
| JP | 2007501940 A | 2/2007 |
| JP | 2007139500 A | 6/2007 |
| JP | 2007303674 A | 11/2007 |
| JP | 2009509134 A | 3/2009 |
| JP | 2009168216 A | 7/2009 |
| WO | 2004011147 A1 | 2/2004 |
| WO | WO 2004011149 A1 * | 2/2004 |
| WO | 2007034404 A2 | 3/2007 |

OTHER PUBLICATIONS

Search Report issued in International Patent Application No. PCT/JP20009/005711; Jan. 26, 2010; Japanese Patent Office.
Notice of Allowance issued in Japanese Patent Application No. 2008-167005; Jul. 24, 2012; 6 pages; Japanese Patent Office.
Office Action issued in Japanese Patent Application No. 2008-276468; Nov. 27, 2012; 6 pages, Japanese Patent Office.
Office Action issued in Japanese Patent Application No. 2009-194590; Nov. 27, 2012; 6 pages, Japanese Patent Office.
Office Action issued in Japanese Patent Application No. 2009-194591; Nov. 27, 2012; 6 pages, Japanese Patent Office.
Office Action issued in Japanese Patent Application No. 2009-194592; Nov. 27, 2012; 6 pages, Japanese Patent Office.
Office Action issued in U.S. Appl. No. 12/739,325; Jan. 4, 2013; 11 pages; U.S. Patent and Trademark Office.
Notice of Allowance issued in U.S. Appl. No. 12/739,325; Apr. 8, 2013; 18 pages; U.S. Patent and Trademark Office.
Japanese Patent Office, Office Action issued in Application No. 2009-194590, mailed Aug. 6, 2013, 4 pp.
Chinese Patent Office, Office Action issued in corresponding Chinese Patent Application No. 201310221154.9 and partial English-language translation mailed Aug. 27, 2014 (8 pages).
Office Action issued in U.S. Appl. No. 13/934,314, mailed Jun. 11, 2015, 19 pages.
United States Patent and Trademark Office, Final Office Action issued in copending U.S. Appl. No. 13/934,314 mailed Dec. 17, 2015.
Pal, Rohit, et al., "Phase Change Microvalve for Integrated Devices," Anal. Chem., vol. 76, No. 13, pp. 3740-3748 (Jul. 1, 2004).

* cited by examiner

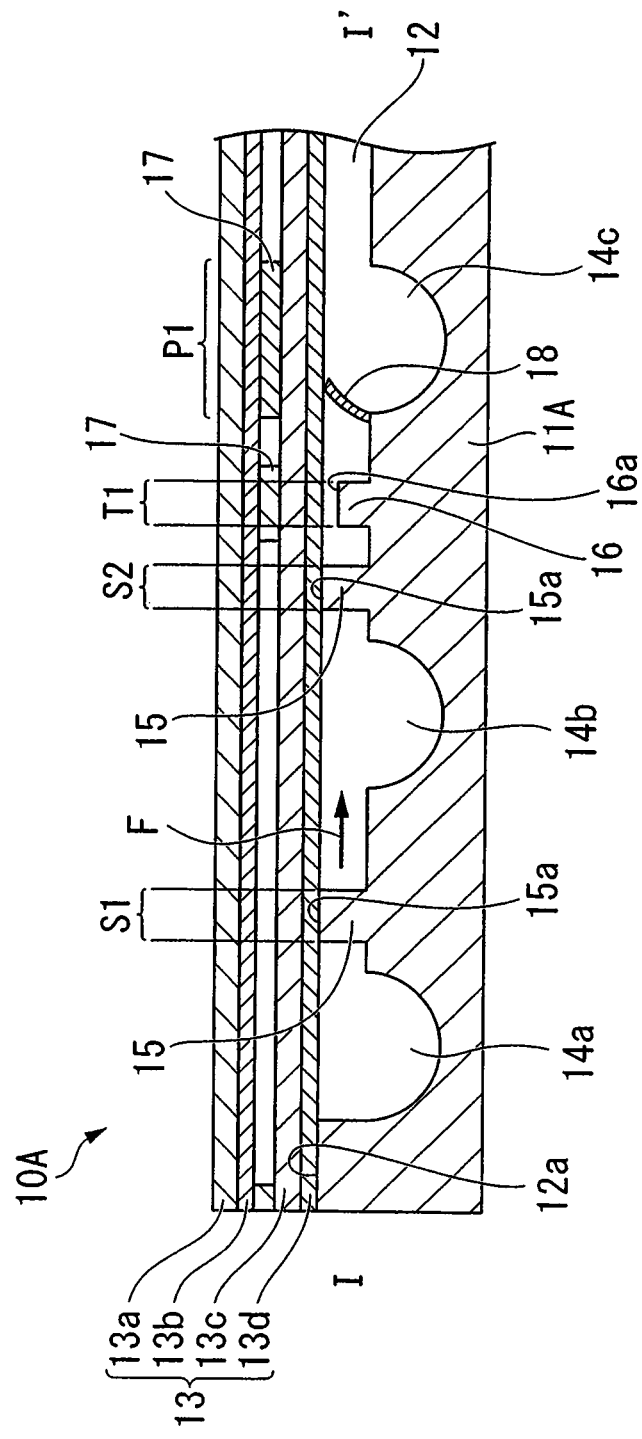

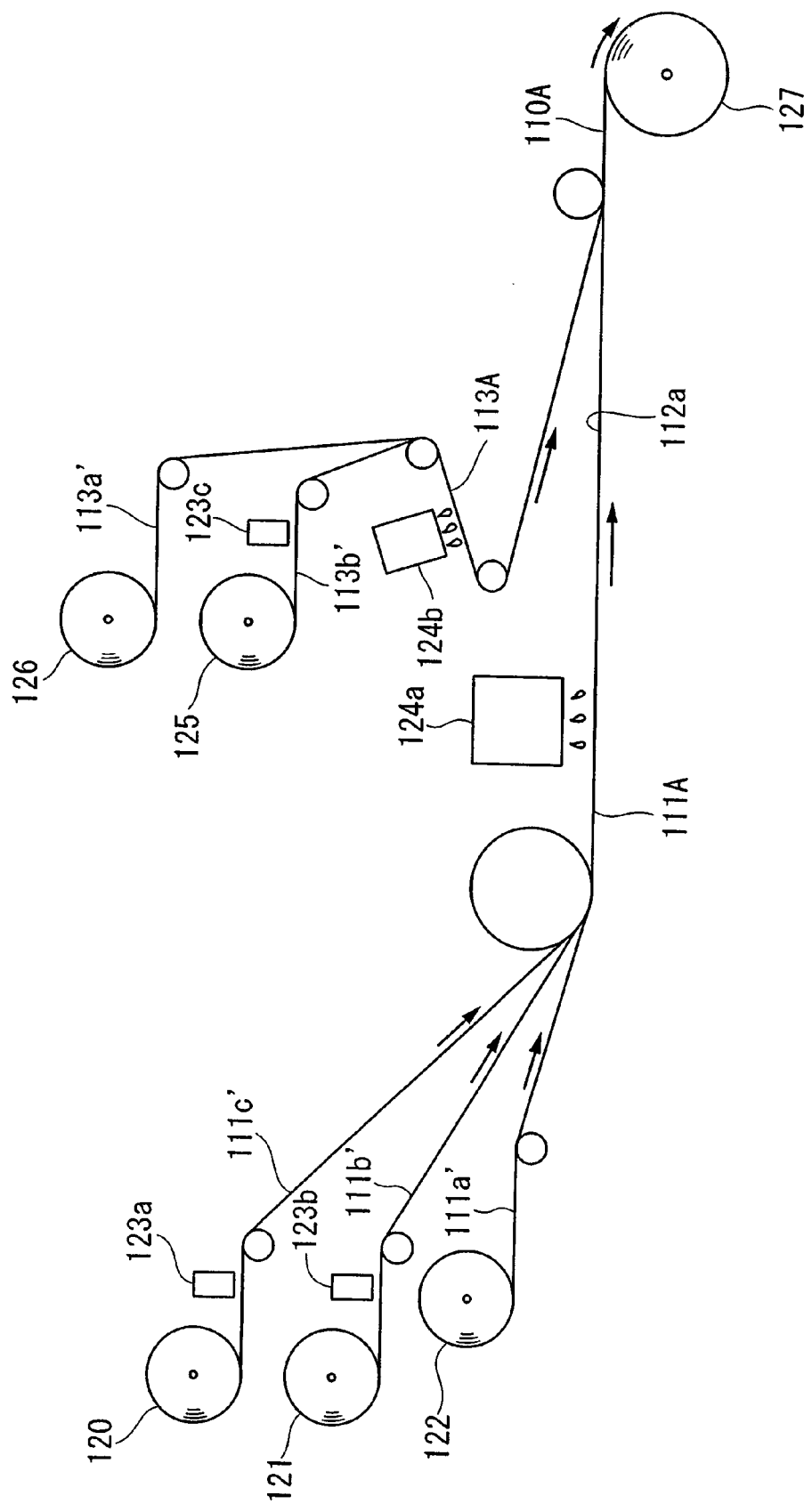

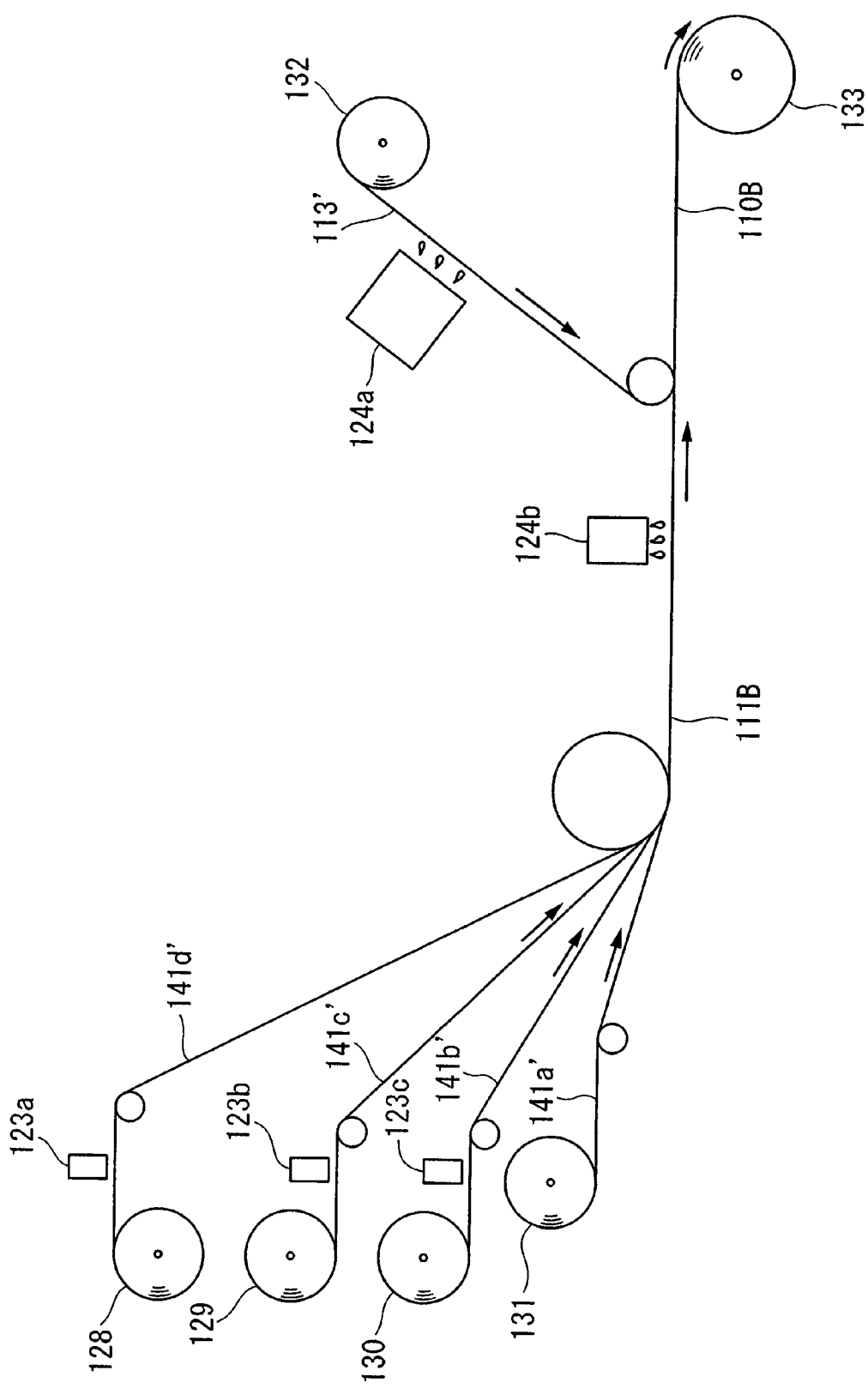

LIQUID CHANNEL DEVICE AND PRODUCTION METHOD THEREFOR

FIELD OF THE INVENTION

The present invention relates to a liquid channel device in the form of a flat plate, which is optimally employed in the detection and analysis of blood antigens for example, and further relates to a production method therefore.

BACKGROUND OF THE INVENTION

Recently, detection and analysis of trace components in liquid samples is frequently carried out in the medical and environmental fields. In this case, a liquid channel device, referred to as a microchip, in which channels are formed in a base plate, is often employed in the medical field, for example.

For example, Patent Document No. 1 discloses a technique in which an antibody-containing reagent and blood are mixed in the liquid channel formed in the microchip and allowed to react. Each microchip is then set in a detection device where the antigen-antibody reaction is detected. Further, Patent Document No. 2 discloses a disk-type liquid channel device in which multiple channels are formed in the radial direction in a rotatable disk and antibodies are adhered in advance to a portion of the channels. By subsequently allowing the bodily fluid to flow through the channels, the antigens in the liquid can be captured through the antibody-antigen reaction.

PRIOR ART REFERENCES

Patent Documents

[Patent Document No. 1] Japanese Unexamined Patent Application, First Publication No. 2007-139500
[Patent Document No. 2] Japanese Unexamined Patent Application, First Publication No. Hei 05-005741

DISCLOSURE OF THE INVENTION

Problems to be Solved by the Invention

However, the liquid channel device disclosed in Patent Reference Document No. 1 requires a separate micropump in order to cause the sample or reagent to flow through the channel. The liquid device disclosed in Patent Document No. 2 requires a device for rotating the disk.

Further, in a conventional liquid channel device of this type, it is impossible to close and open the liquid channels. This is inconvenient when detecting and analyzing a target component.

In addition, in this type of conventional liquid channel device, it is impossible to open a portion of the liquid channel from the closed mode, close a portion of the liquid channel from the open mode, or to close or open a portion of the liquid channel. This is inconvenient with respect to the detection and analysis of a target component.

It is the object of the present invention to provide a liquid channel device at low cost which is capable of easily opening the liquid channel from the closed mode without requiring a separate device for inducing flow of the liquid, i.e., a liquid channel device which is capable of causing a liquid to flow easily and smoothly in the channel.

It is the further object of the present invention to provide a liquid channel device at low cost which is capable of easily opening the liquid channel from the closed mode, closing the liquid channel from the open mode, and changing the liquid channel from the open to the closed mode and from the closed to the open mode.

Means for Solving the Problem

The liquid channel device according to the present invention is a liquid channel device including a base plate having a liquid channel through which a liquid containing at least one of a sample and a reagent, flows, and one or more liquid chambers for holding the liquid, are formed to at least one side thereof, and a cover plate which is laminated onto a channel formation surface of the base plate where the liquid channel and the liquid chambers are formed, wherein at least one of the liquid chambers has a liquid transport section for transporting the liquid from the inside to the outside of the liquid chamber, and the liquid transport section is operated by external pressing on a floor of the liquid chamber or to the cover plate in the area corresponding to the liquid chamber.

In the liquid channel device according to the present invention, it is preferable that the liquid channel device further include an opening section which opens a portion of the liquid channel from a closed mode and a closing section which closes a portion of the liquid channel from an open mode;

the cover plate have a first base layer which forms the surface of the cover plate, a strongly adhered layer which is formed to the inside of the first base layer, a second base layer which is formed to the inside of the strongly adhered layer, and a weakly adhered layer which is formed to the inside of the second base layer and is adhered to the channel formation surface;

in the opening section, a first convex section be formed to the liquid channel, the top part of the first convex section and the weakly adhered layer be adhered, and the strongly adhered layer and the second base layer be separated;

in the closing section, a second convex section be formed to the liquid channel, the top part of the second convex section and the weakly adhered layer be separated, and a spacer be interposed between the strongly adhered layer and the second base layer, and the spacer and the strongly adhered layer be adhered together;

in the liquid transport section, a spacer be interposed between the strongly adhered layer and the second base layer, and the spacer and the strongly adhered layer be adhered.

In the liquid channel device according to the present invention, it is preferable that the base plate include an outer layer, a middle layer which is laminated to the inside of the outer layer, and an inner layer which is laminated to the inside of the middle layer;

a top part of the liquid chamber, the liquid channel, the first convex section, and the second convex section be formed to the inner layer; and a bottom part of the liquid chamber be formed to the middle layer.

In the liquid channel device according to the present invention, it is preferable that the base plate include an outer layer, and an inner layer which is laminated to the inside of the outer layer; and the liquid chamber, the liquid channel, the first convex section, and the second convex section be formed to the inner layer.

In the liquid channel device according to the present invention, it is also preferable that a reverse flow check for preventing reverse flow of the liquid transported by the liquid transport section be provided to the liquid chambers that are provided with a liquid transport section.

Further, in this case, it is preferable that the reverse flow check be formed to the inner layer.

When the liquid transport section is operated by external pressing on the floor of the liquid chambers, it is preferable that the floor be formed expanding outward.

The liquid channel device according to the present invention is a liquid channel device including a base plate in which a liquid channel, through which a liquid containing at least one of a sample and a reagent flows, is formed to at least one side thereof, and a cover plate which is laminated to a channel formation surface of the base plate where the liquid channel is formed, wherein the liquid channel device further includes an opening section for opening a portion of the liquid channel from a closed mode;

the cover plate includes a first base layer forming a surface of the cover plate, a strongly adhered layer formed to the inside of the first base layer, a second base layer formed to the inside of the strongly adhered layer, and a weakly adhered layer which is formed to the inside of the second base layer and is adhered to the channel formation surface; and in the opening section, a first convex section is formed to the liquid channel, a top part of the first convex section and the weakly adhered layer are adhered, and the strongly adhered layer and the second base layer are separated.

In the liquid channel device according to the present invention, it is preferable that the liquid channel device further includes a closing section for closing a portion of the liquid channel from an open mode, and in the closing section, a second convex section is formed to the liquid channel, a top part of the second convex section and the weakly adhered layer be separated, a spacer be interposed between the strongly adhered layer and the second base member, and the spacer and the strongly adhered layer be adhered.

In the liquid channel device according to the present invention, it is also preferable that the liquid channel device further include a metering chamber for quantifying a specific volume of the liquid provided to the liquid channel, and the closing section is provided upstream with respect to the metering chamber, and the opening section is provided downstream with respect to the metering chamber.

In the liquid channel device according to the present invention, it is also preferable that the metering chamber include an overflow section for allowing overflow of the liquid in excess of the specific volume.

The liquid channel device according to the present invention is a liquid channel device including a base plate in which a liquid channel through which a liquid flows and one or more liquid chambers for holding the liquid are formed to at least one surface thereof, and a cover plate which is laminated to a channel formation surface in which the liquid channel and the liquid chambers of the base plate are formed, wherein the liquid channel device further includes an opening section for opening a portion of the liquid channel from a closed mode, the opening section includes a stopper which is disposed to a portion of the liquid channel, and which undergoes plastic deformation by means of external pressing on the cover plate or the floor of the liquid channel, thereby opening the liquid channel.

In the liquid channel device according to the present invention, it is preferable that the cover plate or the floor of the liquid channel that is in contact with the stopper be subjected to a releasing treatment.

The production method for the liquid channel device according to the present invention is a production method including:

a first step of forming the liquid chambers and the liquid channel to the base plate, a second step of forming the stopper to a portion of the liquid channel, and a third step of laminating the cover plate to the channel formation surface of the base plate, in the first step, a top part of the liquid chambers and the liquid channel are formed to a sheet which forms the inner layer of the base plate, and after a bottom part of the liquid chambers is formed to a sheet which forms the middle layer of the base plate, the sheet forming the inner layer, the sheet forming the middle layer, and a sheet forming the outer layer of the base plate are laminated sequentially.

In the production method, it is preferable that, in the second step, the stopper be formed by coating a stopper forming material for forming the stopper to a portion of the liquid channel.

The liquid channel device according to the present invention is a liquid channel device including a base plate in which a liquid channel through which a liquid flows and one or more liquid chambers for holding the liquid that are formed to at least one surface thereof, and a cover plate which is laminated to a channel formation surface of the base plate in which the liquid channel and the liquid chambers are formed, wherein the liquid channel device further includes a closing section for closing a portion of the liquid channel from the open mode;

the closing section includes a sealing material supply chamber which is formed branching from a portion of the liquid channel, a sealing material which fills the sealing material supply chamber and is extruded out into part of the liquid channel by external pressing on a floor of the sealing material supply chamber or on the cover plate in an area corresponding to the sealing material supply chamber, thereby closing the liquid channel.

The production method for the liquid channel device according to the present invention is a production method including:

a first step in which the liquid channel, the liquid chambers, and the sealing material supply chamber are formed to the base plate;

a second step in which the sealing material supply chamber is filled with the sealing material;

a third step in which the cover plate is laminated to the channel formation surface of the base plate; and in the first step, a top part of the liquid chambers, the liquid channel, and the sealing material supply chamber are formed to a sheet which forms an inner layer of the base plate, and a bottom part of the liquid chambers is formed to a sheet which forms a middle layer of the base plate, then the sheet forming the inner layer, the sheet forming the middle layer and a sheet forming an outer layer of the base plate are laminated sequentially.

In the production method, it is preferable that, in the second step, the sealing material is filled by coating the sealing material to the sealing material supply chamber.

The liquid channel device according to the present invention is a liquid channel device including a base plate in which a liquid channel through which a liquid flows and one or more liquid chambers for holding the liquid are formed to at least one surface thereof, and a cover plate which is laminated to a channel formation surface of the base plate where the liquid channel and the liquid chambers are formed, wherein the liquid channel device further includes an opening section for opening a portion of the liquid channel from a closed mode;

the opening section is equipped with a stopper which is disposed to a portion of the liquid channel, and a concave section capable of housing the stopper at a position on an inner surface of the cover plate or a floor of the liquid channel that is opposite the stopper; and the stopper is moved from the portion of the liquid channel to within the concave section by external pressing on the cover plate or the floor, thereby opening the liquid channel.

The production method for a liquid channel device according to the present invention is a production method for the liquid channel device in which the concave section is formed to an inner surface of the cover plate, wherein the production method includes:

a first step of forming the liquid channel and the liquid chambers to the base plate, and forming the concave section to the cover plate;

a second step of forming the stopper to a portion of the liquid channel; and a third step of laminating the cover plate to the channel formation surface of the base plate, in the first step, a top part of the liquid chambers and the liquid channel are formed to a sheet that forms an inner layer of the base plate, and a bottom part of the liquid chambers is formed to a sheet that forms a middle layer of the base plate, then the sheet forming the inner layer, the sheet forming the middle layer and a sheet forming an outer layer of the base plate are laminated sequentially, thereby forming the liquid channel and the liquid chambers to the base plate, and the concave section is formed to the sheet that forms the inner layer of the cover plate, after that, the sheet that forms the inner layer of the cover plate and the sheet that forms the outer layer of the cover plate are laminated to form the concave section in the cover plate.

The production method for a liquid channel device according to the present invention is a production method for the liquid channel device in which the concave section is formed to the floor of the liquid channel, wherein the production method includes:

a first step of forming the liquid channel, the liquid chambers, and the concave section to the base plate, a second step of forming the stopper to a position opposite the concave section on the inner surface of the cover plate, and a third step of laminating the cover plate to the channel formation surface of the base plate, in the first step, a top part of the liquid chambers and the liquid channel are formed to a sheet that forms an inner layer of the base plate, the middle part of the liquid chambers and the concave section are formed to a sheet that forms an inside middle layer of the base plate, and the bottom part of the liquid chambers are formed to a sheet that forms an outside middle layer of the base plate, after which the sheet forming the inner layer of the base plate, the sheet forming the inside middle layer, the sheet forming the outside middle layer, and the sheet forming an outer layer of the base plate are laminated sequentially.

Further, the liquid channel device according to the present invention is a liquid channel device including a base plate in which a liquid channel through which a liquid flows and one or more liquid chambers for holding the liquid are formed to at least one surface thereof, and a cover plate which is laminated to a channel formation surface of the base plate in which the liquid channel and the liquid chambers are formed, wherein the liquid channel device further includes a closing section for closing a portion of the liquid channel from an open mode;

the closing section includes a stopper which is housed within a concave section formed to an inner surface of the cover plate or a floor of the liquid channel, the stopper moves from within the concave section to a portion of the liquid channel due to external pressing on the cover plate or the floor, thereby closing the liquid channel.

The production method for a liquid channel device according to the present invention is a production method for the liquid channel device in which the concave section is formed to the inner surface of the cover plate, including:

a first step of forming the liquid channel and liquid chambers to the base plate, and forming the concave section to the cover plate;

a second step of forming the stopper within the concave section; and a third step of laminating the cover plate to the channel formation surface of the base plate;

in the first step, a top part of the liquid chambers and the liquid channel are formed to a sheet that forms the inner layer of the base plate, and a bottom part of the liquid chambers is formed to a sheet that forms the middle layer of the base plate, after which the sheet forming the inner layer of the base plate, the sheet forming the middle layer of the base plate and a sheet forming the outer layer of the base plate are laminated sequentially, to form the liquid channel and the liquid chambers to the base plate, and a concave section is formed to the sheet forming the inner layer of the cover plate, after which the sheet forming the inner layer of the cover plate and the sheet forming the outer layer of the cover plate are laminated to form the concave section in the cover plate.

The production method for a liquid channel device according to the present invention is a production method for the liquid channel device in which the concave section is formed to the floor of the liquid channel, including:

a first step of forming the liquid channel, liquid chambers and the concave section to the base plate;

a second step of forming the stopper within the concave section; and a third step of laminating the cover plate to the channel formation surface of the base plate;

in the first step, a top part of the liquid chambers and the liquid channel are formed to a sheet that forms the inner layer of the base plate, a middle part of the liquid chambers and the concave section are formed to a sheet that forms the inside middle layer of the base plate, and a bottom part of the liquid chambers is formed to a sheet that forms the outside middle layer of the base plate, after which the sheet forming the inner layer of the base plate, the sheet forming the inside middle layer, the sheet forming the outside middle layer, and a sheet forming the outer layer of the base plate are laminated sequentially.

In the production method, it is preferable that, in the second step, the stopper is formed by coating the stopper forming material for forming the stopper.

Effects of the Invention

The present invention enables the provision of a low cost liquid channel device in which the liquid channel can be easily opened from the closed mode, i.e., which is capable of causing a liquid to flow in the channel easily and smoothly, without requiring a separate device for causing flow of the liquid.

Further, the present invention provides a liquid channel device at low cost which is capable of easily opening the liquid channel from the closed mode, closing the liquid channel from the open mode, or changing the liquid channel from the open to the closed and from the closed to the open modes.

BRIEF DESCRIPTION OF THE DRAWINGS

FIG. 3 is a cross-sectional view along the line I-I' in FIG. 2.

FIG. 27 is a process figure for schematically explaining the production process for the liquid channel device in FIG. 21.

FIG. 34 is a process figure for schematically explaining the production method for the liquid channel device in FIG. 30.

BEST MODE FOR CARRYING OUT THE INVENTION

The present invention will now be explained in detail.

First Embodiment

Figure 1:
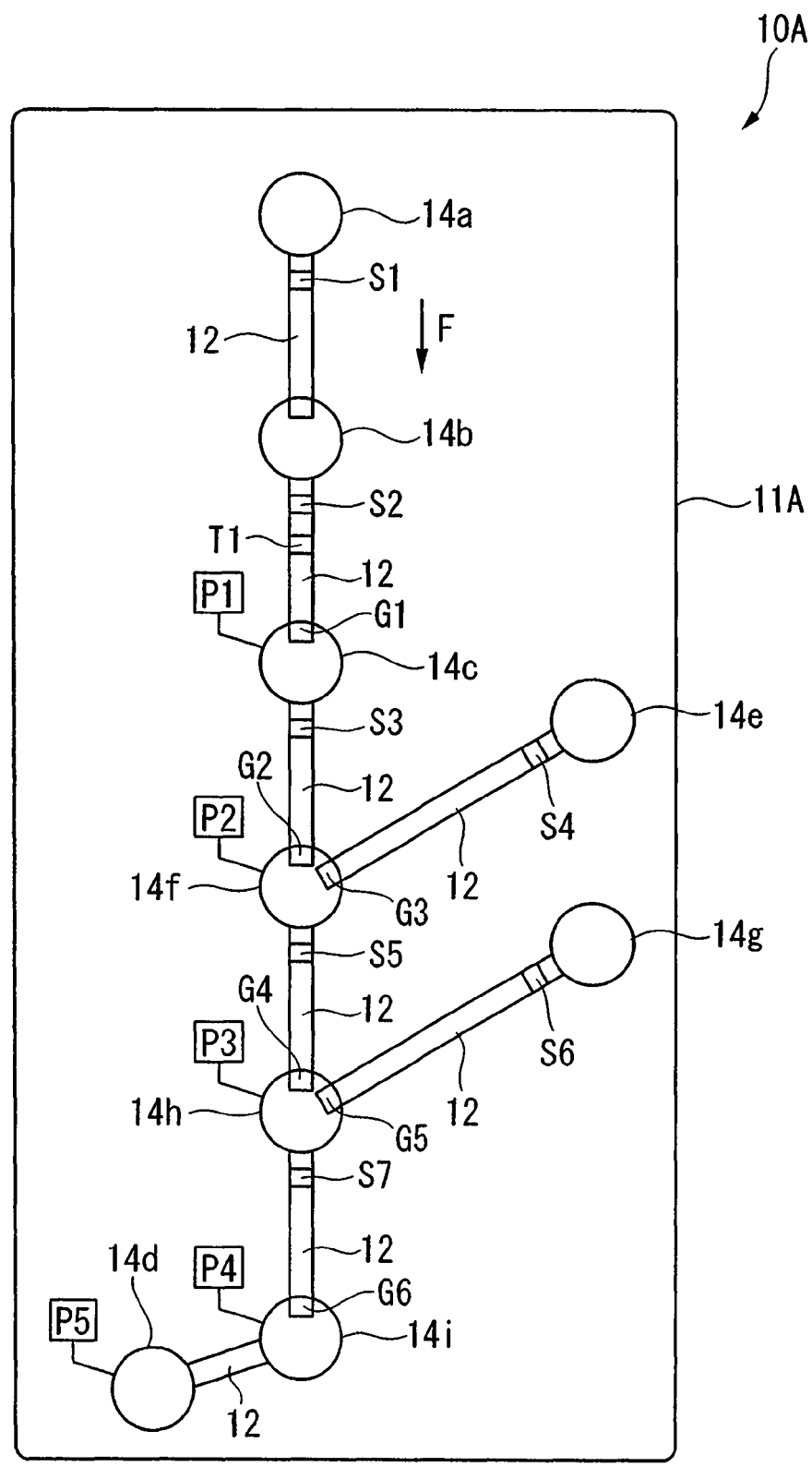
FIG. 1 is a schematic planar perspective view showing the liquid channel device according to a first embodiment.
Figure 2:
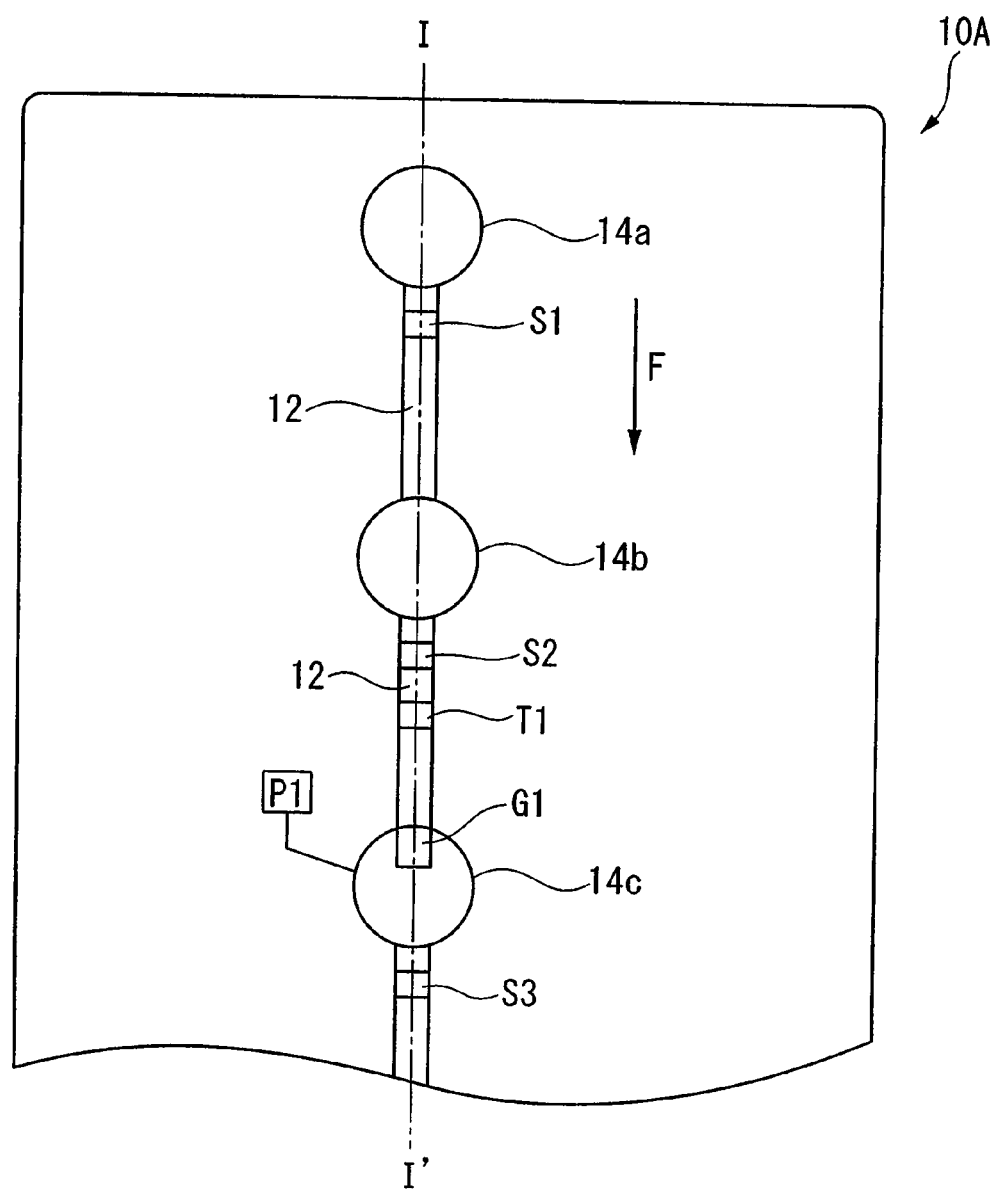
FIG. 2 is a planar perspective view in which a portion of the liquid channel device in FIG. 1 is enlarged.

FIG. 1 is a planar perspective view schematically showing a liquid channel device 10A according to a first embodiment of the present invention. FIG. 2 is a planar perspective view in which a part of the liquid channel device 10A in FIG. 1 is enlarged. FIG. 3 is a cross-sectional view along the line I-I' in FIG. 2.

In this liquid channel device 10A, a groove-like liquid channel 12 through which a liquid, which contains at least one of a sample and a reagent, flows, and a plurality (nine in this embodiment) of liquid chambers 14a~14i for storing the liquid at the ends of or along the liquid channel 12, are formed to one side of a flat square base plate 11A. Further, a cover plate 13 is laminated onto a channel formation surface 12a on the side of the base plate 11A where the liquid channel 12 and the liquid chambers 14a~14i are formed.

In the liquid channel device 10A according to this embodiment, by merely directing the top part in FIG. 1 upward and the bottom part in FIG. 1 downward, the sample flows under the force of gravity from the upstream to the downstream end of the liquid channel 12 in the direction of arrow F. Along the way, various procedures and mixing with reagents occur to the sample, thereby formulating a measured liquid which is supplied to various detection and analyses. However, as will be explained in detail below, a smooth and easy flow of the liquid is obtained in this embodiment by incorporating the use of liquid transport sections at the liquid chambers.

A sample introduction chamber 14a, which holds the introduced sample, is provided to the upstream end of the liquid channel 12. A filtering chamber 14b housing a filter, which is not shown in figures, and filters the sample which has flowed from the sample introduction chamber 14a, is provided downstream from the sample introduction chamber 14a. A metering chamber 14c, which is formed so that its internal capacity has a specific volume and which can quantify the filtered sample, is provided downstream from the filtering chamber 14b.

An overflow section, which includes an overflow path 12b and a waste solution chamber 14d provided downstream from the overflow path 12b, is provided to the metering chamber 14c in this embodiment. For this reason, sample in excess of a specified quantity overflows at the metering chamber 14c, flows through the overflow path 12b, and flows into the waste solution chamber 14d. As a result, a specific quantity of the sample can be quantified at the metering chamber 14c.

A first mixing chamber 14f is provided downstream from the metering chamber 14c for mixing the sample which was quantified in the metering chamber 14c and a liquid first reagent, a specific quantity of which was sealed in advance in the first reagent chamber 14e. A second mixing chamber 14h is provided downstream from the first mixing chamber 14f for mixing the intermediate solution formulated in first mixing chamber 14f and a liquid second reagent, a specific quantity of which was sealed in advance in the second reagent chamber 14g.

A measuring chamber 14i is provided downstream from the second mixing chamber 14h. A measured liquid formulated in the second mixing chamber 14h is stored in the measuring chamber 14i. The detection and analysis of various components are carried out by a detecting and analyzing section not shown in the figures.

Note that in this embodiment, a mixing tank 14d is provided downstream from the measuring chamber 14i, the mixing tank 14d communicating with the measuring chamber 14i via the liquid channel 12. As will be explained in detail below, once the measured liquid inside the measuring chamber 14i is sent to the mixing tank 14d, by repeating as needed the mixing operation, in which the liquid is sent back into the measuring chamber 14i, the measured liquid can be sufficiently stirred and mixed, so that it is in a more suitable condition for detection and analysis.

Communicating holes, not shown in the figures, which are capable of opening and closing and which communicate with the outside environment, are provided to each of the liquid chambers.

As shown in FIG. 3, the cover plate 13 of the liquid channel device 10A includes a first base layer 13a which forms the front surface of the cover plate 13; a strongly adhered layer 13b which is formed on the inner side of the first base layer 13a; a second base layer 13c which is formed on the inner side of the strongly adhered layer 13b; and a weakly adhered layer 13d which is formed on the inner side of second base layer 13c and which is adhered to a channel formation surface 12a.

The first base layer 13a is made of a material that will bend when a vertically directed (i.e., in the direction which intersects vertically with the first base layer 13) load is applied on its front surface side, and which has restorative force that will return to its original state once the load is removed. In contrast, the second base layer 13c is made of a material which easily bends when the same load is subjected, but does not return to its original state even when the load is removed, i.e., a material which readily undergoes plastic deformation. Further, the adhesive strength of the strongly adhered layer 13b is formed to be greater than that of the weakly adhered layer 13d.

This liquid channel device 10A includes opening sections S1~S7, for changing a part of the liquid channel 12 from the closed state to the open state, and a closing section T1 for changing a part of the liquid channel 12 from the open state to the closed state.

In this embodiment, one of the opening sections S1~S7 is disposed along the various liquid channels 12 between the sample introduction chamber 14a and the filtering chamber 14b; between the filtering chamber 14b and the metering chamber 14c; between the metering chamber 14c and the first mixing chamber 14f; between the first mixing chamber 14f and the second mixing chamber 14h; between the first reagent chamber 14e and the first mixing chamber 14f; between the second reagent chamber 14g and the second mixing chamber 14h; and the second mixing chamber 14h and the measuring chamber 14i.

The closing section T1 is provided farther downstream than the opening section S2 on the liquid channel 12 that is between the filtering chamber 14b and the metering chamber 14c.

S1 and S2 in FIG. 3 will now be used as examples for explaining the various opening sections S1~S7. A first convex section 15 is formed to the liquid channel 12. The top part 15a of the first convex section 15 and the weakly adhered layer 13*d* are adhered together, and the strongly adhered layer 13*b* and the second base layer 13*c* are separated from one another.

Figure 4A:
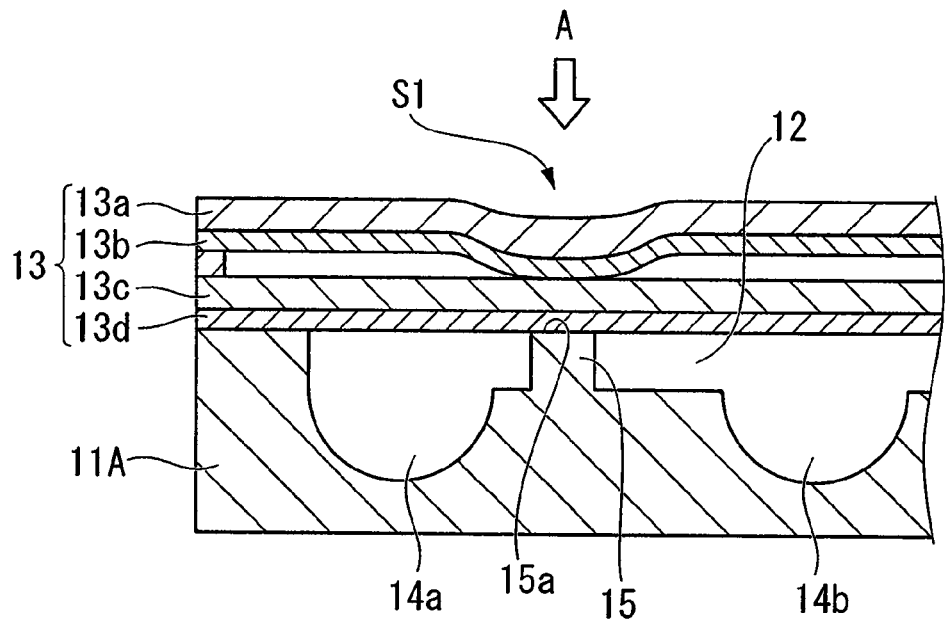
FIG. 4A is an explanatory figure for explaining the condition in the open channel portion operates in the liquid channel device of FIG. 1.
Figure 4B:
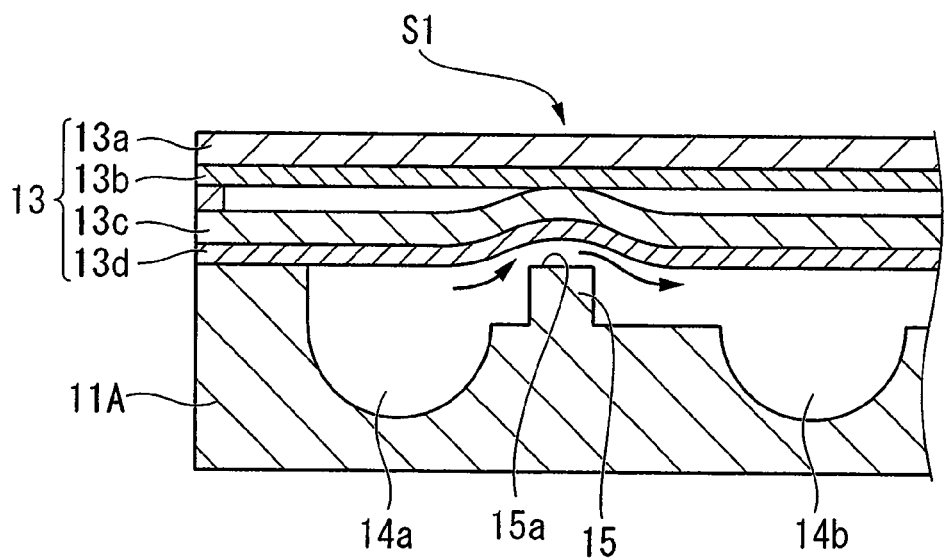
FIG. 4B is an explanatory figure for explaining the condition when the open channel portion operates in the liquid channel device of FIG. 1.

Thus, the liquid channel 12 at the various opening sections S1~S7 is closed off by the first convex section 15 and the weakly adhered layer 13*d* which is adhered to the top part 15*a* of the first convex section 15, and is typically in the closed state. However, as shown by the example of opening section S1 in FIGS. 4A and 4B, when the first base layer 13*a* at the opening section S1 is pressed from the front surface in the direction of arrow A, so that a vertically directed load is applied to the first base layer 13*a*, then, as shown in FIG. 4A, the first base layer 13*a* bends and the strongly adhered layer 13*b* on the inside of the first base layer 13*a* adheres to the second base layer 13*c*. When the load is subsequently removed, then, as shown in FIG. 4B, the first base layer 13*a* is restored to its original state due to its restorative force. At this time, the strongly adhered layer 13*b* which is adhered to the inside of the first base layer 13*a*, the second base layer 13*c* which is adhered to the strongly adhered layer 13*b* and is easily elastically deformable, and the weakly adhered layer 13*d* which is adhered to the inside of the second base layer 13*c*, are lifted up accompanying the restoration of the first base layer 13*a*. As a result, the space between the top part 15*a* of the first convex section 15 and the weakly adhered layer 13*d* separates for the first time, so that liquid can flow through.

In the thus-designed opening sections S1~S7, a vertically directed load is applied by pressing the cover plate 13 from the front surface. Subsequently, a pressing operation to remove the load is performed, so that space separates between the top part 15*a* of the first convex section 15 and the weakly adhered layer 13*d* which were originally adhered together. As a result, the liquid channel 12 in this area opens from the closed mode.

A second convex section 16 is formed in the liquid channel 12 at the closing section T1, as shown in FIG. 3. The top part 16*a* of this second convex section 16 and the weakly adhered layer 13*d* are separated from one another, and a spacer 17 is interposed between the strongly adhered layer 13*b* and the second base layer 13*c*. The spacer 17 and the strongly adhered layer 13*b* are adhered.

Figure 5A:
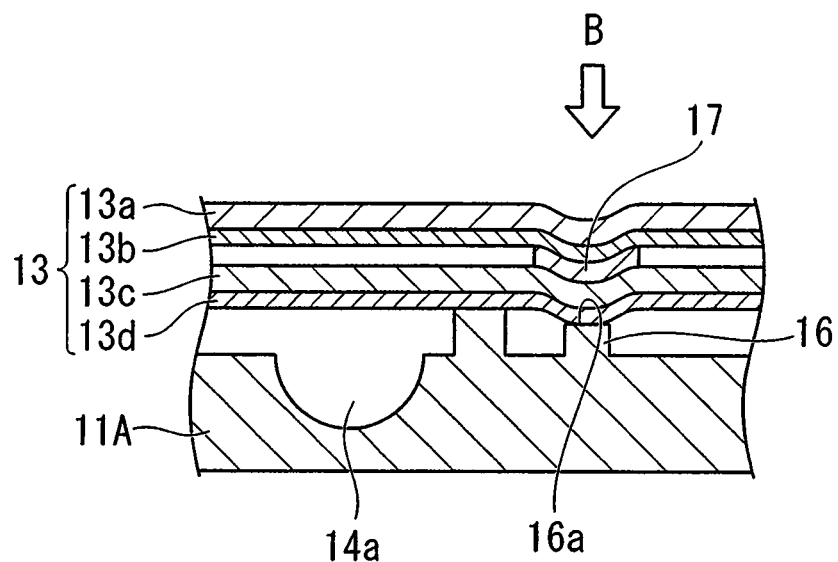
FIG. 5A is an explanatory figure for explaining the condition when the closing part operates in the liquid channel device of FIG. 1.
Figure 5B:
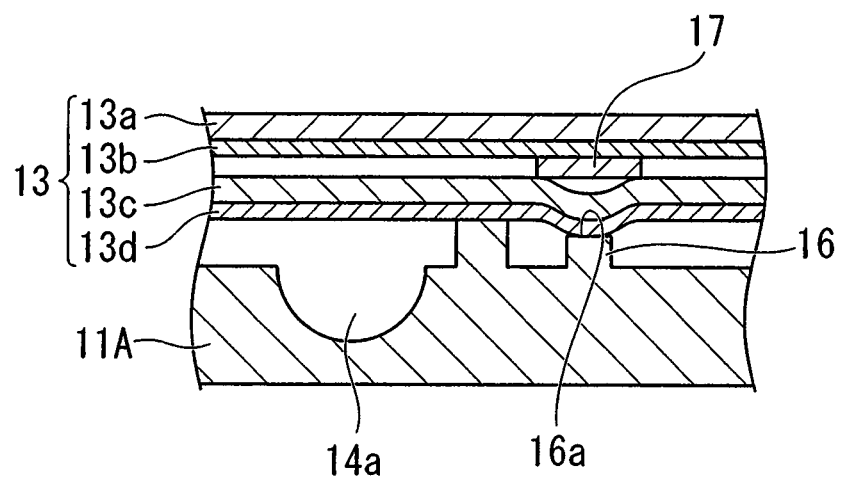
FIG. 5B is an explanatory figure for explaining the condition when the closing part operates in the liquid channel device of FIG. 1.

Thus, in the liquid channel 12 at the closing section T1, the channel is maintained by the separation of space between the top part 16*a* of the second convex section 16 and the weakly adhered layer 13*d*, and is typically in the open state. However, as shown in FIG. 5A, when the first base layer 13*a* at the closing section T1 is pressed from the front surface in the direction of arrow B, so that a vertically directed load is applied to the first base layer 13*a*, then the first base layer 13*a* bends and the weakly adhered layer 13*d* on the inside of the cover plate 13 adheres to the top part 16*a* of the second convex section 16. When the load is subsequently removed, then, as shown in FIG. 5B, the first base layer 13*a* is restored to its original state due to its restorative force. At this time, the strongly adhered layer 13*b* which is adhered on the inside of the first base layer 13*a*, and the spacer 17 which is adhered to the strongly adhered layer 13*b*, are lifted up accompanying the restoration of the first base layer 13*a*. The space between the spacer 17 and the second base layer 13*c* are not adhered, and the second base layer 13*c* is easily plastically deformable, so that, even if the load is removed, the second base layer 13*c* and the weakly adhered layer 13*d* do not follow the restoration of the first base layer 13*a*. As a result, the top part 16*a* of the second convex section 16 and the weakly adhered layer 13*d* are in an adhered state, thereby closing the liquid channel 12 so that the liquid cannot flow through.

In the thus-designed closing section T1, a vertically directed load is applied by pressing the cover plate 13 from the front surface side. By employing a pressing operation to remove the load, the space between the originally separated top part 16*a* of the second convex section 16 and the weakly adhered layer 13*d* adheres and closes. As a result, the liquid channel 12 in this area closes from the open mode.

In the liquid channel device 10A in this embodiment, the metering chamber 14*c*, first mixing chamber 14*f*, second mixing chamber 14*h*, measuring chamber 14*i*, and mixing tank 14*d* each have a liquid transport section P1~P5 for sending the liquid from inside to outside the various chambers.

Among the various liquid transport sections P1~P5, the liquid transport section P1 of the metering chamber 14*c* sends the liquid inside metering chamber 14*c* downstream, i.e., toward the first mixing chamber 14*f*. Similarly, the liquid transport section P2 of the first mixing chamber 14*f* sends the liquid inside first mixing chamber 14*f* downstream, i.e., toward the second mixing chamber 14*h*. The liquid transport section P3 of the second mixing chamber 14*h* sends the liquid inside second mixing chamber 14*h* downstream, i.e., toward the measuring chamber 14*i*. The liquid transport section P4 of the measuring chamber 14*i* sends the liquid inside the measuring chamber 14*i* downstream, i.e., toward the mixing tank 14*d*.

In contrast, the liquid transport section P5 of the mixing tank 14*d* sends the liquid inside mixing tank 14*d* upstream, i.e., toward the measuring chamber 14*i*.

Further, in this embodiment, in the cover plate 13 at the area corresponding to the various liquid chambers having the liquid transport sections P1~P5 (the cover plate at the part for closing the liquid chambers), the space between the strongly adhered layer 13*b* and the second base layer 13*c* is not separated, but rather has a spacer 17 interposed there between. The spacer 17 and the strongly adhered layer 13*b* are adhered and the layers are tightly formed.

Figure 6A:
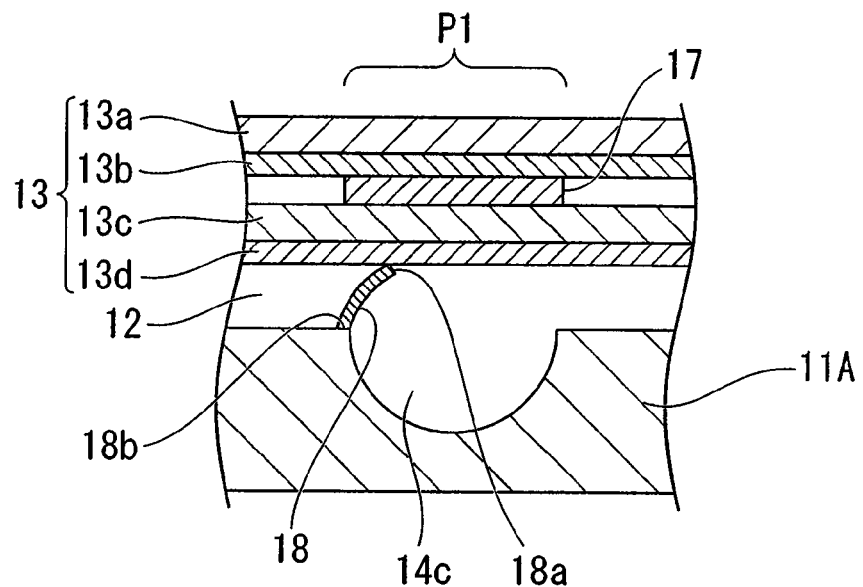
FIG. 6A is an explanatory figure for explaining the condition when the liquid sending portion operates in the liquid channel device of FIG. 1.
Figure 6B:
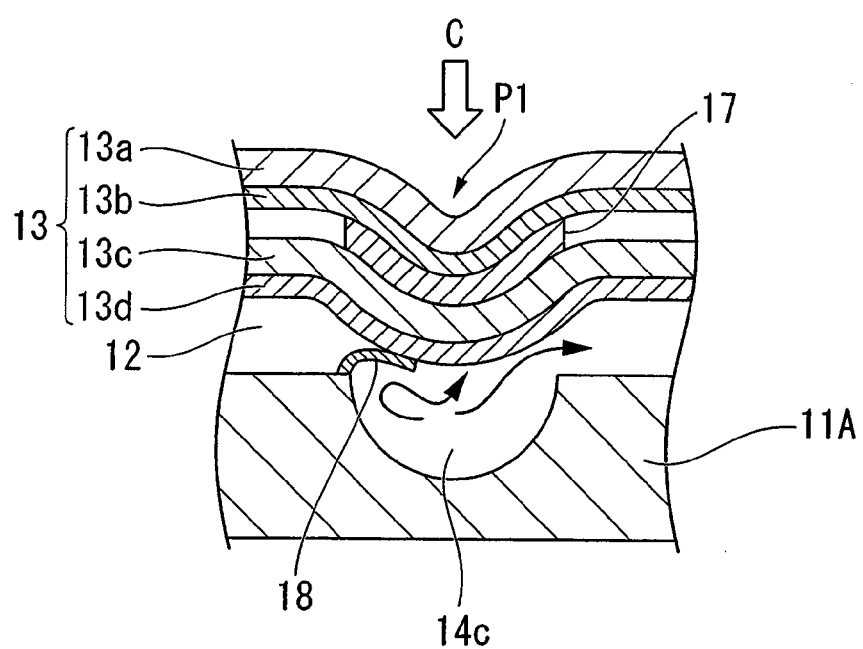
FIG. 6B is an explanatory figure for explaining the condition when the liquid sending portion operates in the liquid channel device of FIG. 1.

For this reason, as shown in FIGS. 6A and 6B and employing liquid transport section P1 as an example, when the cover plate 13 at this area is pressed from the outside in the direction shown by arrow C (FIG. 6B), then the cover plate 13 at this pressed portion bends inward. As a result, the internal capacity of the metering chamber 14*c* becomes smaller, causing the liquid inside the metering chamber 14*c* to be expelled and transported, thereby realizing the function as the liquid transport section P1. Hypothetically, if the space between the strongly adhered layer 13*b* and the second base layer 13*c* is separated without interposing a spacer 17, so that the layers are not tight, then it is possible that the internal capacity of the metering chamber 14*c* will not be decreased simply by the adhesion of the strongly adhered layer 13*b* to the second base layer 13*c* even when the cover plate 13 of this portion is pressed from the outside. In this case, the function as a liquid transport section will not be realized.

In this embodiment, the metering chamber 14*c*, first mixing chamber 14*f*, second mixing chamber 14*h* and measuring chamber 14*i* which are each provided with this type of liquid transport section P1~P4, are also provided with a reverse flow check G1~G6 for stopping the reverse flow of the liquid sent from the liquid transport section P1~P4 upstream, as shown in FIGS. 1 and 2. Thus, when the liquid transport sections P1~P4 are operated, the liquid inside the various chambers cannot undergo reverse flow but can only flow downstream.

In this embodiment, the reverse flow checks G1~G6 are a flexible dam plate 18.

Figure 7:
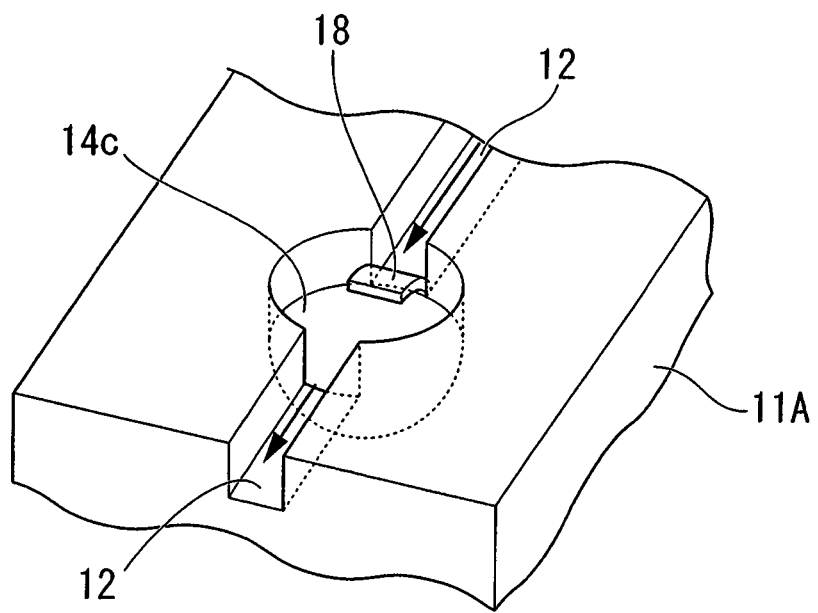
FIG. 7 is a perspective view in which a portion of the base plate of the liquid channel device in FIG. 1 is enlarged.

For example, using the metering chamber 14*c* as an example, as shown in FIGS. 6A, 6B and 7, at the boundary between the metering chamber 14*c* and the liquid channel 12 on the upstream side of the metering chamber 14c, only the base end 18b of the dam plate 18 is fixed to the floor of the liquid channel 12 so that the front end 18a of the dam plate 18 is directed downstream. The distal end 18a and either lateral edges are not fixed in place.

For this reason, when liquid is transported from the filtering chamber, not shown in the figures, to the metering chamber 14c in FIGS. 6A, 6B and 7, the liquid can surpass the distal end 18a of the dam plate 18 and flow into the metering chamber 14c.

On the other hand, when the liquid transport section P1 of metering chamber 14c operates, and the internal capacity of the metering chamber 14c decreases, the liquid inside the metering chamber 14c can only flow downstream due to the disposition of this dam plate 18, and cannot flow upstream, i.e., undergo reverse flow toward the filtering chamber.

Note that the mixing tank 14d is provided for sufficiently stirring and mixing the measured liquid by bringing the measured liquid from and sending the measured liquid to the upstream measuring chamber 14i as described above. Thus, it is not necessary to provide a reverse flow check for preventing reverse flow of the liquid upstream to the mixing tank 14d.

As a specific method for formulating the measured liquid using the liquid channel device 10A, first the liquid channel device 10A is placed so that the sample introduction chamber 14a is positioned upward and the measuring chamber 14i is positioned downward, so that the liquid easily flows from upstream to downstream under the force of gravity.

The sample is sampled in a syringe or the like, the needle of the syringe is pierced into the cover plate 13 at the portion corresponding to the sample introduction chamber 14a of the syringe, and the sample is injected into the sample introduction chamber 14a. Thereafter, the opening section S1 which is provided in between the sample introduction chamber 14a and the filtering chamber 14b is subjected to pressing as described above, i.e., has a load applied by pressing the front surface of the first base layer 13a. The load is subsequently removed, and the liquid channel 12 at this portion is rendered in the open state, so that the sample is introduced to the filtering chamber 14b by the force of gravity.

The pressing operation may be carried out by means of the operator using his finger to perform a pressing action from the front surface of the first base layer 13a, or by employing a preprogrammed pressing device in which the pressing position is defined by XY coordinates, and pressing in a specific position.

Once filtering has been carried out at filtering chamber 14b, the opening section S2 which is provided in between the filtering chamber 14b and the metering chamber 14c is operated by pressing, so that the liquid channel 12 in this area is opened, and the sample is introduced into the metering chamber 14c under the force of gravity.

Once a specific amount of sample is held and quantified at the metering chamber 14c, the closing section T1 that is provided in between the filtering chamber 14b and the metering chamber 14c is operated by pressing, so that the liquid channel 12 in this area is closed. In this way, the further introduction into the metering chamber 14c of liquid from upstream is prevented. Thus, by operating the opening section S3 that is provided downstream from the metering chamber 14c by pressing, it is possible to open the liquid channel 12 in this area. Next, the liquid transport section P1 is operated by applying external pressure to the cover plate 13 in the area covering the metering chamber 14c. The quantified sample is thus introduced into the first mixing chamber 14f due to the force of gravity and the action of the liquid transport section P1.

The thus quantified sample is introduced into the first mixing chamber 14f, and the opening section S4 in between the first reagent chamber 14e and the first mixing chamber 14f is operated by pressing so that the first reagent is introduced into the first mixing chamber 14f. The sample and the first reagent are mixed in the first mixing chamber 14f, to formulate an intermediate solution.

Next, the opening section S5 in between the first mixing chamber 14f and the second mixing chamber 14h is operated by pressing so that the liquid channel 12 in the areas is opened. Next, the liquid transport section P2 is operated in the same manner as the liquid transport section P1. The intermediate solution formulated at the first mixing chamber 14f is introduced into the second mixing chamber 14h through the force of the gravity and the action of liquid transport section P2. The opening section S6 in between the second reagent chamber 14g and the second mixing chamber 14h is operated by pressing so that the second reagent is introduced into second mixing chamber 14h. The intermediate solution and the second reagent are mixed in the second mixing chamber 14h, to formulate a measured liquid.

Next, the opening section S7 which is provided in between the second mixing chamber 14h and the measuring chamber 14i is operated by pressing, so that the liquid channel 12 in this area is opened. Next, the liquid transport section P3 is operated, and the measured liquid formulated in second mixing chamber 14h is introduced into the measuring chamber 14i through the force of gravity and the action of the liquid transport section P3.

Next, the liquid transport section P4 is operated and the measured liquid inside the measured chamber 14i is transported at once to the mixing tank 14d. Next, the liquid transport section P5 is operated to transport the measured liquid inside the mixing tank 14d back to the measuring chamber 14i. This mixing operation is repeated as necessary until the measured liquid is sufficiently stirred and mixed. This is then supplied to the detecting and analyzing section for each liquid channel device 10A, and detection and measurement of the target components is carried out on the measured liquid inside the measuring chamber 14i.

Note that when the liquid transport sections P1~P5 are operated and the liquid is made to flow into the liquid channel 12 of the liquid channel device 10A, it is optimal to suitably open and close the communicating holes, not shown in the figures, which are provided to the various liquid chambers so that the liquid flows more smoothly. For example, the cover plate 13 in the area corresponding to the metering chamber 14c is pressed when operating the liquid transport section P1. Next, the communicating holes provided in the metering chamber 14c are switched from the closed to the open state prior to releasing the pressure. Next, by releasing the pressing force, the pressure inside the metering chamber 14c is reduced and the liquid transported downstream can be prevented from flowing backward into the metering chamber 14c.

According to the liquid channel device 10A, the liquid transport sections P1~P5 for transporting the liquid inside the liquid chambers are provided to the metering chamber 14c, the first mixing chamber 14f, the second mixing chamber 14h, the measuring chamber 14i and the mixing chamber 14d, respectively. As a result, easy and smooth flow of the liquid can be accomplished and it is not necessary to separately provide a device for forcing flow of the liquid, even in the case where the sample, intermediate solution and measured liquid are viscous and do not readily flow through the liquid channel 12.

Further, the liquid transport sections P1~P5 are provided with a design which utilizes the cover plate 13 of the liquid channel device 10A. Thus, it is not necessary to newly prepare a separate material for the liquid transport sections P1~P5. Thus, low cost and simple construction is achieved. In addition, since the liquid transport sections P1~P5 are operated by simple pressing alone, operability is superior.

Further, in this embodiment, a dam plate 18 is provided to serve as reverse flow checks G1~G6 to the metering chamber 14c, the first mixing chamber 14f, the second mixing chamber 14h, and the measuring chamber 14i which are provided to the liquid transport sections P1~P4, respectively. For this reason, when the liquid transport sections P1~P4 are operated, the liquid does not undergo reverse flow upstream.

Further, the liquid channel device 10A of this embodiment is provided with opening sections S1~S7 which open the liquid channel 12 from the closed mode, and the closing section T1 which closes the liquid channel 12 from the open mode. The flow of the liquid in the liquid channel 12 can thus be controlled, making it possible to quickly carry out a highly accurate detection and analysis.

For example, a closing section T1 is provided upstream and an opening section S3 is provided downstream from the metering chamber 14c in this embodiment. As a result, it is possible to quickly and accurately quantify the sample, and introduce it into the first mixing chamber 14f. If, hypothetically, a opening section S3 was not provided downstream from the metering chamber 14c so that the liquid channel 12 in this area was always in the open state, then the sample would continuously be flowing out from the metering chamber 14c even during the process of quantification. Accordingly, quantification would become difficult because it would not be possible to hold a specific quantity of the sample. In addition, when a closing section T1 is not provided upstream from the metering chamber 14c, then, depending on the amount of sample injected into the sample introduction chamber 14a, the sample which has passed through the filtering chamber 14b may continue to flow into the metering chamber 14c even after a specific quantity of sample accumulates in the metering chamber 14c. Thus, quantification itself may of course become difficult. On this point, when a closing section T1 is provided upstream from the metering chamber 14c as in this embodiment, then, even if the entire amount of sample that passed through the filter 14b has not completely finished flowing into the metering chamber 14c, it is possible to operated the closing section T1 at the point in time when a fixed quantity of sample has been quantified in the metering chamber 14c, thereby preventing further flow of sample into the metering chamber 14c. The sample can thus be accurately and quickly quantified.

Further, in this embodiment, a opening section S5 is provided in between the first mixing chamber 14f and the second mixing chamber 14h, and a opening section S7 is provided in between the second mixing chamber 14h and the measuring chamber 14i. For this reason, once the targeted mixing and reaction has progressed sufficiently in the first mixing chamber 14f and the second mixing chamber 14h, these opening sections S5, S7 are opened and the liquid transport sections P2, P3 are operated, so that the intermediate solution and the measured liquid can each be introduced into the second mixing chamber 14h and the measuring chamber 14i, respectively. Thus, it is possible to prevent a deterioration in the accuracy of the detection and analysis which is caused by insufficient mixing and reaction.

Further, in this embodiment, opening sections S4,S6 are provided in between the first reagent chamber 14e and the first mixing chamber 14f, and the second reagent chamber 14g and the second mixing chamber 14h. As a result, these opening sections are opened at the desired point in time, and the first reagent and the second reagent, which are sealed in advance in the first reagent chamber 14e and the second reagent chamber 14g respectively, can be introduced into the first mixing chamber 14f and the second mixing chamber 14h. Hypothetically, if these opening sections S4, S6 were not provided, then there would be a concern that the first reagent and the second reagent would begin to flow downstream during maintenance and the like of the liquid channel device 10A.

The opening sections S1~S7 and the closing section T1 of the liquid channel device 10A are made by incorporating a first convex section 15, and a second convex section 16, which are formed to the liquid channel 12, and the cover plate 13. For this reason, it is not necessary to newly prepare a separate member for opening or closing the liquid channel 12. Thus, low cost and a simple structure can be achieved. Further, operability is superior since the opening and closing operation can be performed by a simple pressing operation.

Note that in the liquid channel device 10A described in the preceding example, the metering chamber 14c, the first mixing chamber 14f, the second mixing chamber 14h, the measuring chamber 14i, and the mixing chamber 14d are each provided with the liquid transport section P1~P5. However, it is also acceptable not to provide all of these liquid chambers with a liquid transport section. In addition, it is also acceptable to provide a liquid transport section to liquid chambers other than those cited here. In other words, it is acceptable to suitably determine which liquid chambers to provide with a liquid transport section depending on the type and characteristics of the sample and the reagents, etc. For example, this embodiment described an arrangement in which, when formulating a measured liquid using the liquid channel device 10A, the liquid channel device 10A is first disposed so that the sample introduction chamber 14a is directed upward and the measuring chamber 14i is directed downward so that the liquid readily flows from upstream to downstream under the force of gravity, and, with this arrangement in place, liquid transport sections P1~P5 are also utilized in transporting the liquid, i.e., the liquid is made to flow through a combination of the force of gravity and the action of the liquid transport sections. However, by providing liquid transport sections to all the liquid chambers, it is also possible to design a liquid channel device that can transport a liquid without utilizing gravity.

Further, an embodiment was provided in which nine liquid chambers were formed in this liquid channel device 10A. However, the type, number, disposition sequence and the like can be suitably adjusted according to the objects.

In the liquid channel device 10A of this embodiment, a dam plate 18 is employed for the reverse flow checks G1~G6 which are disposed to the liquid chambers which are provided with liquid transport sections P1~P4. However, the present invention is not limited to this embodiment of a reverse flow check. Rather, embodiments other than dam plate 18 are acceptable. When a dam plate 18 is provided, two or more dam plate 18 may be disposed in a series, or a design which more effectively will obtain the reverse flow check effect may be used. Alternatively, the dam plate 18 may be combined with other reverse flow checks.

In place of providing reverse flow checks G1~G6, a closing section for closing the liquid channel 12 from the open mode may be provided at these sites. By operating the closing section before actuating the liquid transport sections P1~P4, the liquid can be prevented from flowing back upstream.

The embodiment which employs a closing section for the objective of checking flow in this way is particularly effective in the case the metering chamber has an overflow section including an overflow path which communicates with the metering chamber and a waste solution chamber which is provided downstream from the overflow path. In this type of metering chamber, sample which exceeds a specific quantity in the metering chamber overflows and flows down the overflow path and into the waste solution chamber. As a result, it is possible to quantify a specific amount of sample in the metering chamber. For this reason, it is necessary that the sample flow smoothly into the overflow path from the metering chamber during quantification. On the other hand, when operating the liquid transport section that is provided to the metering chamber to send the quantified sample downstream, the sample must be prevented from flowing into the overflow path from the metering chamber. As explained, a reverse flow check cannot be provided a place through which the sample flows in both directions. Accordingly, it is preferable to provide the closing section to such a place in order to make the place be closed only when necessary.

Figure 8:
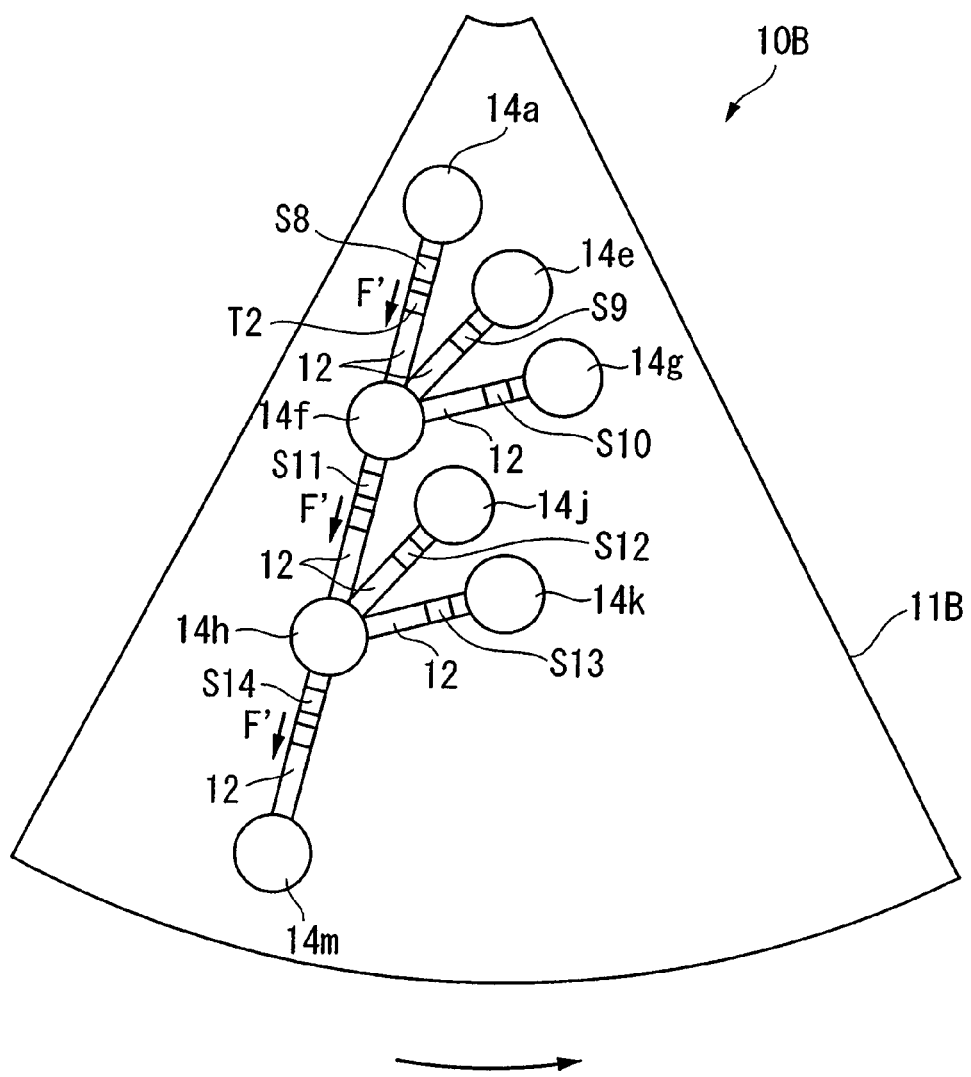
FIG. 8 is a schematic planar perspective view showing a second embodiment of the liquid channel device according to the present invention.

FIG. 8 shows a second embodiment of the liquid channel device according to the present invention. As in the case of the liquid channel device 10A explained above, this liquid channel device 10B is formed by forming the groove-like liquid channel 12, through which the liquid is the sample and/or the reagent flows, and a plurality of liquid chambers (14a, 14e~14h, 14J, 14k, 14m) for holding the liquid at either end or a part of the liquid channel 12, to one surface of the base plate 11B made of a fan-shaped flat plate, and laminating the cover plate 13 to the channel formation surface 12a which is on the side of the base plate 11 where the liquid channel 12 is formed. In this liquid channel device 10B, when the upper end as shown in FIG. 8 is rotated about the center, the sample flows under centrifugal force in the direction of the arrow F' from the upstream end toward the downstream end of the liquid channel 12. Various treatments and mixing with reagents are carried out along the way, to form the measured liquid.

In other words, the sample introduction chamber 14a in which the introduced sample is held is provided to the upstream end of the liquid channel 12, and a first mixing chamber 14f is provided downstream from the sample introduction chamber 14a for mixing the first reagent from the first reagent chamber 14e, the second reagent from the second reagent chamber 14g and the sample from the sample introduction chamber 14a, to formulate an intermediate solution.

A second mixing chamber 14h is provided downstream from the first mixing chamber 14f for mixing the third reagent from the third reagent chamber 14j, the fourth reagent from the fourth reagent chamber 14k, and the intermediate solution from the first mixing chamber 14f.

In this embodiment, the second mixing chamber 14h is employed as a measuring chamber, and detection and analysis of various components is carried out using the detecting and analyzing section not shown in the figures on the measured liquid which was formulated in the second mixing chamber 14h.

In this embodiment, a waste solution chamber 14m is formed in which the measured liquid is stored after being measured at the second mixing chamber 14h.

Note that communicating holes, not shown in the figures, which communicate with the air are provided to the various liquid chambers.

Further, in this liquid channel device 10B, the cover plate 13 has the same structure as shown in FIG. 3 for the case of the above-described liquid channel device 10A, i.e., has the first base layer 13a forming the front surface of the cover plate 13, the strongly adhered layer 13b which is formed on the inside of the first base layer 13a, the second base layer 13c formed to the inside of the strongly adhered layer 13b, and the weakly adhered layer 13d which is formed to the inside of the second base layer 13c and is adhered to the channel formation surface.

Opening sections S8~S14 for opening the liquid channel 12 from the closed mode are disposed respectively between the sample introduction chamber 14a and the first mixing chamber 14f; between the first sample chamber 14e and the first mixing chamber 14f; between the second sample chamber 14g and the first mixing chamber 14f; between the first mixing chamber 14f and the second mixing chamber 14h; between the third sample chamber 14j and the second mixing chamber 14h; between the fourth sample chamber 14k and the second mixing chamber 14h; and between the second mixing chamber 14h and the waste solution chamber 14m.

A closing section T2 is provided downstream from the opening section S8 in the liquid channel 12 between the sample introduction chamber 14a and the first mixing chamber 14f.

As in the case of the liquid channel device 10A, in the various opening sections S8~S14, the first convex section 15 is formed to the liquid channel 12, as shown in FIG. 3. The top part 15a of the first convex section 15 and the weakly adhere layer 13d are adhered and the strongly adhered layer 13b and the second base layer 13c are separated. The second convex section 16 is formed to the liquid channel 12 at the closing section T2. The top part 16a of the first convex section 16 and the weakly adhered layer 13d are separated from one another. The spacer 17 is interposed between the strongly adhered layer 13b and the second base layer 13c. The spacer 17 and the strongly adhered layer 13b are adhered.

When formulating the measured liquid using the liquid channel device 10B, first, the liquid channel device 10B is set in a centrifuge so that the sample introduction chamber 14a side is positioned on the rotational center side and the measuring chamber 14i is positioned on the outer periphery side of the rotation.

Next, the sample is sampled using a syringe or the like, and the syringe needle is used to pierce the cover plate 13 in the area corresponding to the sample introduction chamber 14a and inject the sample into the sample introduction chamber 14a. Next, the centrifuge is operated to generate a centrifugal force that acts from the center of rotation to the outer periphery. As a result of this centrifugal force, the liquid starts to flow from upstream to downstream.

Next, in the same manner as in the case of the liquid channel device 10A, pressing is applied to the opening section S8 which is provided in between the sample introduction chamber 14a and the first mixing chamber 14f, so that the liquid channel 12 in this area is opened to the from the closed mode and the sample is introduced into the first mixing chamber 14f under the centrifugal force.

The sample is introduced into the first mixing chamber 14f as the centrifugal force is being generated in this way. Meanwhile, the opening section S9 in between the first sample chamber 14e and the first mixing chamber 14f is activated by pressing, to introduce the first reagent, which was sealed in advance, into the first mixing chamber 14f. Next, the opening section S10 in between the second reagent chamber 14g and the first mixing chamber 14f is activated by pressing, to introduce the second reagent, which was sealed in advance, into the first mixing chamber 14f. The sample, the first reagent and the second reagent are mixed in the first mixing chamber 14f.

At this time, as necessary, the closing section T2 may be operated prior to the entire sample flowing completely into the first mixing chamber 14f, so that overflow of the sample into the first mixing chamber 14f can be prevented.

Next, the opening section S11 in between the first mixing chamber 14f and the second mixing chamber 14h is operated by pressing, to introduce the intermediate solution formulated in the first mixing chamber 14f into the second mixing chamber 14h. Meanwhile, the opening section S12 in between the third reagent chamber 14j and the second mixing chamber 14h, and the opening section S13 in between the fourth reagent chamber 14k and the second mixing chamber 14h are operated by pressing, to introduce the third reagent and the fourth reagent, which were sealed in advance, into the second mixing chamber 14h. The intermediate solution, the third reagent and the fourth reagent are mixed in the second mixing chamber 14h.

Next, the liquid channel device 10B is supplied to the detecting and analyzing section, and detection and analysis of the target components is carried out on the measured liquid formulated in the second mixing chamber.

Once the detection and analysis is completed, the opening section S14 is operated and liquid on which measurements are completed can be discarded to the waste solution chamber 14m.

This type of liquid channel device 10B is provided with opening sections S8~S14 opening the liquid channel 12 from the closed mode, and a closing section T2 for closing the liquid channel 12 from the open mode. As a result, it is possible to control the flow of the liquid in the liquid channel 12, so that detection and analysis can be carried out over a short time with good accuracy.

Further, the opening sections S8~S14 and the closing section T2 are low cost and simple in design, and can be operated by means of simple pressing alone.

Note that the pressing operation applied to the opening sections S8~S14 and closing section T2 may be carried out manually in the case of the liquid channel device 10B of this embodiment. However, if the pressure is applied by means of a pressure disk that is in contact with the front surface of the cover plate 13 of the liquid channel device 10B, then it is possible to carry out continuous pressing to a plurality of liquid channel devices 10B, which is preferable.

Figure 9:
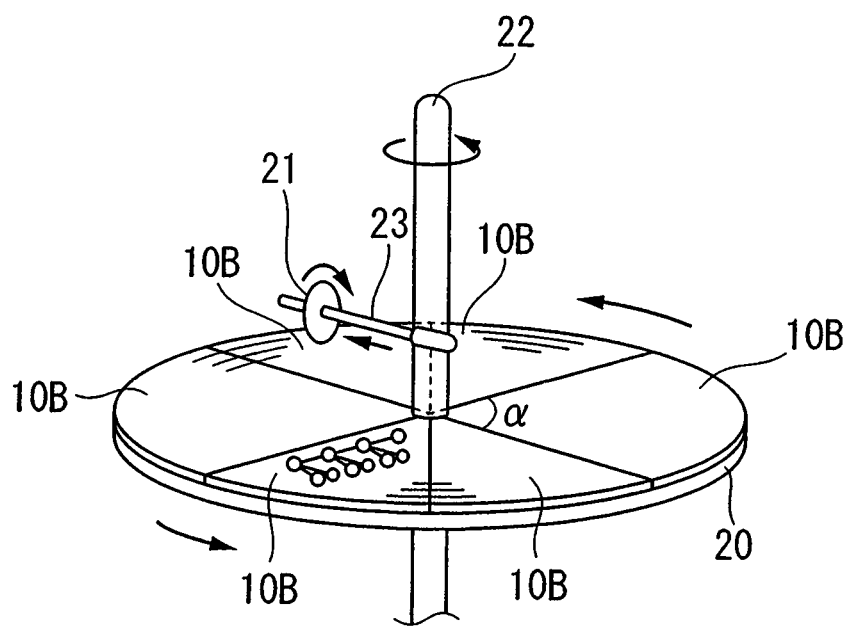
FIG. 9 is a schematic explanatory view for explaining an example of the method of use for the liquid channel device in FIG. 8.

FIG. 9 shows a method for using a pressure disk 21 to carry out pressing to a plurality (six in this embodiment) of the fan-shaped (central angle α=60°) liquid channel devices 10B which are aligned in a circle and set on the base 20 of a centrifuge. The pressure disk 21 of this embodiment is installed on an arm 23 that extends laterally from the rotational axis 22 of the centrifuge for rotating the liquid channel devices 10B. While rotating about arm 23, this pressure disk 21 moves along the longitudinal direction of the arm 23 (the radial direction of rotation of the liquid channel device) from the center to the outer periphery of rotation of the liquid channel device 10B. The pressure disk 21 undergoes which movement while the liquid channel device 10B is rotated by the centrifuge. As a result, the pressure disk 21 scans in a relatively spiraling pattern from the center to the outer periphery of rotation on the liquid channel devices 10B which are aligned in a circle, and pressing can be applied sequentially to the opening sections S8~14 and the closing section T2 that are provided on these liquid channel devices 10B.

Note that the above explanation employed a method in which the cover plate 13 was pierced with a syringe needle as an example of a method for injecting the sample into the sample introduction chamber 14a of the liquid channel devices 10A, 10B. However, for example, it is also acceptable to form a sample injection hole in the cover plate 13 in advance, and to then inject the sample from there. In this case, a protective tape may be used to cover the sample injection hole, with the injection carried out by piercing the protective tape with the syringe. Alternatively, it is also acceptable to peel off the protective tape and then carry out the injection by introducing the syringe into the sample injection hole.

A plate made from glass or a resin such as styrene resin, acrylic resin, polycarbonate resin, vinyl chloride resin, PEN resin, polyester resin, epoxy resin, phenol resin, ABS resin, polypropylene resin, fiber-reinforced plastic or the like, may be employed in the base plate 11A, 11B in which the liquid channel 12 and liquid chambers are formed in the above-described liquid channel devices 10A, 10B. Among these, a glass plate, styrene resin, acrylic resin, polycarbonate resin, vinyl chloride resin, PEN resin, and polyester resin are preferred because they are transparent and enable visual inspection of the condition of the liquid flowing through the liquid channel 12 from the base plate 11A, 11B side. Resin plates are preferred over a glass plate as they do not readily break and are easier to handle.

The thickness of the base plate 11A, 11B is not particularly restricted, but may be determined based on the depth of the liquid channel 12 which is formed therein. Typically, the thickness is 0.5~7 mm The liquid channel 12 and the liquid chambers are formed in the shape of a groove to one side of the base plates 11A, 11B using a technique such as photolithography, injection molding, blow molding, bonding, fusion, cutting, machining or the like.

The cross-sectional shape (i.e., cross-sectional in the direction perpendicular to flow) of the liquid channel 12 is not particularly restricted. For example, semi-circle, square, or inverted triangle is all acceptable shapes which may be cited. The width and depth of the liquid channel 12 are not particularly restricted, and may be determined based on the liquid flow volume which is to be obtained. A width and depth in the range of from 10 to 5,000 um is preferred as the liquid flows with low channel resistance and a small volume of liquid can be made to flow.

Further, in order to facilitate the flow of the liquid in the liquid channel 12, it is preferable to carry out surface processing in response to the type of liquid. Examples of such surface treatments include coating treatments with a coating material, plasma treatment, frame treatment, chemical treatment, biologically active treatment, antibody treatment and the like. Further, as necessary, it is also acceptable to provide a baffle, stirring plate, or projection, and form a divide, so that the flowing liquid has a uniform mixing state.

The shape of the various chambers is not particularly restricted. Rather, the chambers may be suitably formed according to the capacity, etc., required of each.

The various dam plates may be formed of a flexible resin sheet and disposed at specific sites, and, when forming the liquid channel 12 or liquid chambers, may be formed in a unitary manner from the base plate 11A.

The first base layer 13a possesses a restorative force which returns it to its original state after bending when a vertically directed load is applied from the front surface thereof. Any material may be employed as the first base layer 13a provided it is one which has these characteristics, i.e., flexibility and restorative force. The material and thickness thereof are not particularly restricted. Films having a thickness in a range of from 50 to 500 um, and being made of polyethylene terephthalate (PET), polyethylene naphthalate (PEN), polycarbonate (PC), polyimide and the like, are preferable for use as the first base layer 13a due to their suitable properties of flexibility and restorative force.

For the second base layer 13c, on the other hand, a material is acceptable which can easily bend as a result of a vertically directed load, with a material lacking restorative force being more preferable. Any base material having these properties may be employed for second base layer 13c. The material and thickness thereof are not particularly restricted. Films having a thickness in a range of from 5 to 50 μm, and being made of metal foils such as aluminum foil or copper foil, paper, or resins such as PET, PEN, PC or polyimide are preferred for use as the second base layer 13c. Where employing paper, it is preferable to use a paper that has been treated for resistance to water. In the case of metal foil, it is preferable to use a metal foil that has been treated for rust resistance.

The material for the strongly adhered layer 13b and the weakly adhered layer 13d can be suitably selected from among conventional adhesive agents in response to the material for first base layer 13a and the second base layer 13c. In this case, the adhesive force (adhesive strength) of the adhesive agent forming the strongly adhered layer 13b needs to be stronger than the adhesive force of the adhesive agent forming the weakly adhered layer 13d. When the adhesive force of the adhesive agent forming the strongly adhered layer 13b is less than the adhesive force of the adhesive agent forming the weakly adhered layer 13d, it is not possible to separate the top part 15a of the first convex section 15 and the weakly adhered layer 13d when pressing on the openings section S1~S14. As a result, the liquid channel 12 cannot be opened. It is preferable that the adhesive force of the adhesive agent forming the strongly adhered layer 13b be 0.1 N/cm or more greater than the adhesive force of the adhesive agent forming the weakly adhered layer 13d, with a value in the range of 0.1~30 N/cm being more preferred. When the adhesive force of the adhesive agent forming the strongly adhered layer 13b is 0.1 N/cm or more than the adhesive force of the adhesive agent forming the weakly adhered layer 13d, the opening sections S1~S14 can be operated with certainty. On the other hand, when the difference in the adhesive forces exceeds 30 N/cm, it becomes difficult to form the adhesive layers.

For this reason, it is preferable to set the adhesive force of the strongly adhered layer 13b to be in the range of 1~30 N/cm, and of the weakly adhered layer 13d to be in the range of 0.05~5 N/cm.

Examples of adhesive agents employed in the strongly adhered layer 13b and the weakly adhered layer 13d which may be cited include acrylics, rubbers, polyurethanes, polyesters, silicon-based adhesive agents and the like. Among these, an acrylic or rubber may be used for the strongly adhered layer 13b, with non-woven cloth or polyester fiber used as the wick material. Acrylic adhesive agents or silicon-based adhesive agents are preferably employed for the weakly adhered layer 13b. In order to maintain the difference between the adhesive force of the strongly adhered layer 13b and the weakly adhered layer 13d within the above-described suitable range, methods may be cited such as suitably adjusting the glass transition temperature of the resin forming the various adhesive agents, including additives in the adhesive such as tackifiers, curing agents or wick material, and adjusting the amount of these additives.

The thickness of the strongly adhered layer 13b and the weakly adhered layer 13d is not limited, but generally in a range of from 10 to 100 μm.

Note that the term "adhesive force" as employed here is defined as the adhesive strength at 180° peeling from a stainless plate as specified in JIS Z 0237.

In addition to resins such as PET, PEN, PC, acrylic resin, epoxy resin, phenol resin, polyurethane resin and the like, paper or the like may also be employed for the spacer 17. The thickness of the spacer 17 is not particularly restricted. However, when the thickness is in the range of 50~2,000 um, the strongly adhered layer 13b and the second base layer 13c can be separated with certainty prior to the operating the opening sections S1~S14, and the strongly adhered layer 13b and the second base layer 13c can be adhered with certainty during the operation.

Third Embodiment

In the liquid channel device 10A according to the first embodiment explained above, the liquid transport sections P1~P5 were exemplified by an arrangement in which pressing was applied from the outside to the cover plate 13 in the area corresponding to the liquid chambers, causing the cover plate 13 to bend in this area and decreasing the capacity of the liquid chamber and thereby transporting the liquid. In the third embodiment, an explanation is made of a liquid transport section in which external pressing is applied to the floor of the liquid chamber rather than to the cover plate 13, thereby decreasing the capacity of the liquid chamber and transporting the liquid inside the liquid chamber.

Figure 10A:
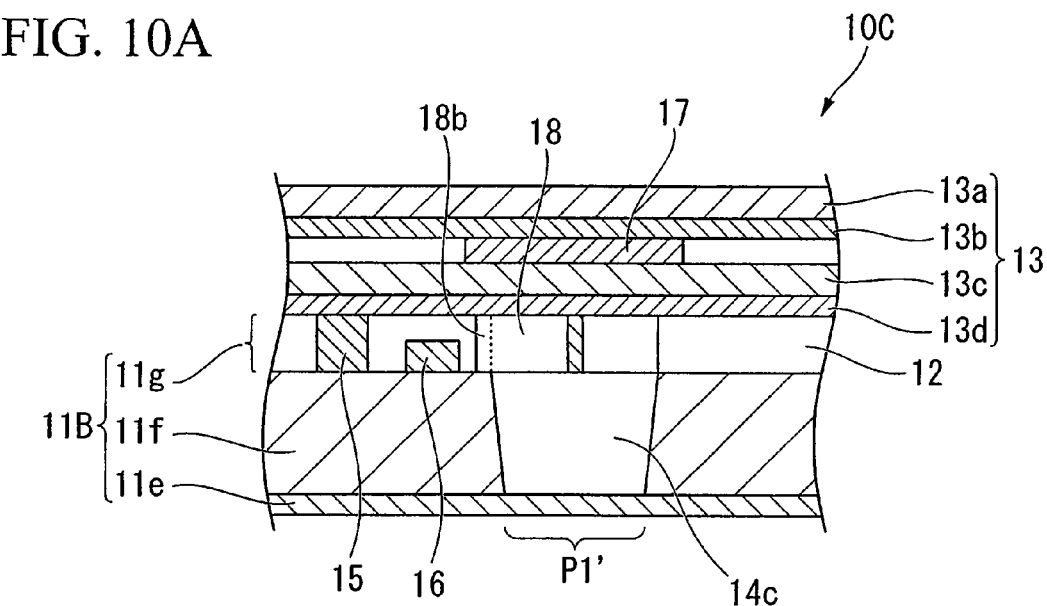
FIG. 10A is an explanatory figure for explaining the condition when the liquid sending part is operating in the liquid channel device according to the third embodiment.
Figure 10B:
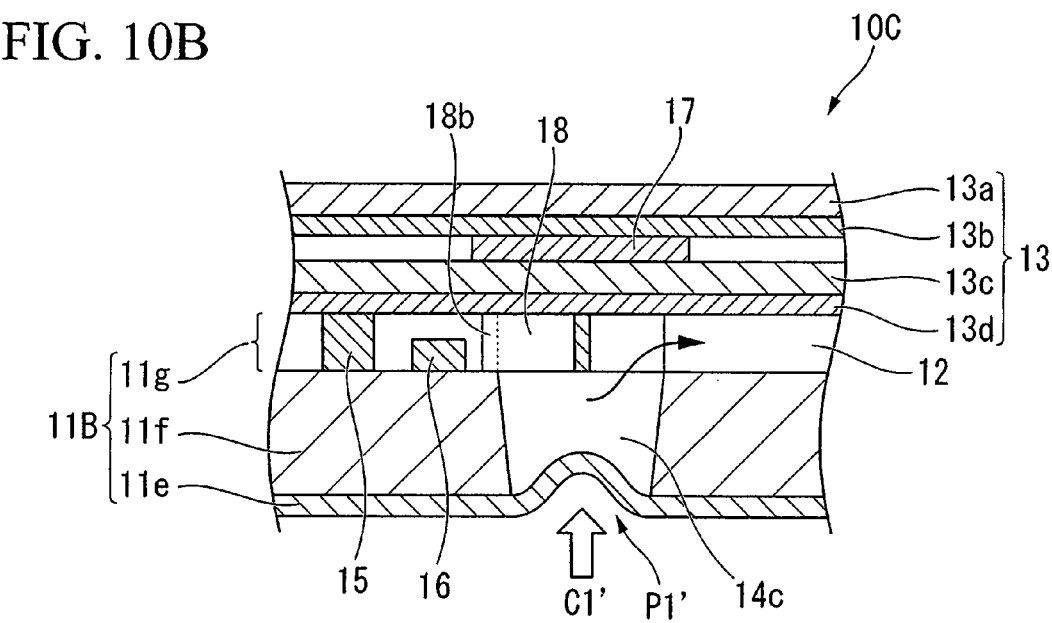
FIG. 10B is an explanatory figure for explaining the condition when the liquid sending part is operating in the liquid channel device according to the third embodiment.

FIGS. 10A and 10B show the essential components including the metering chamber 14c having a liquid transport section P1' for a liquid channel device 10C according to the third embodiment which is equipped with nine liquid chambers in the same manner as in the first embodiment.

In this embodiment, the base plate 11B is made of the three layers of an outer layer 11e, a middle layer 11f which is laminated on the inside of the outer layer 11e, and an inner layer 11g which is laminated on the inside of the middle layer 11f.

The top part of the liquid chambers (only metering chamber 14c is shown in this embodiment), the liquid channel 12, the first convex section 15, and the second convex section 16 are formed to the inner layer 11g.

The bottom part of the liquid chambers is formed to the middle layer 11f, and this middle layer 11f forms the floor of the liquid channel 12.

The outer layer 11e is disposed to the outermost side of the base plate 11B and forms the floor of the liquid chamber. In this embodiment, the liquid transport section P1' operates when external pressing is applied to the floor of the liquid chamber as shown by arrow C', causing the outer layer 11e which forms the floor of the liquid chamber to bend inward and decrease the internal capacity of the metering chamber 14c as a result.

Figure 11:
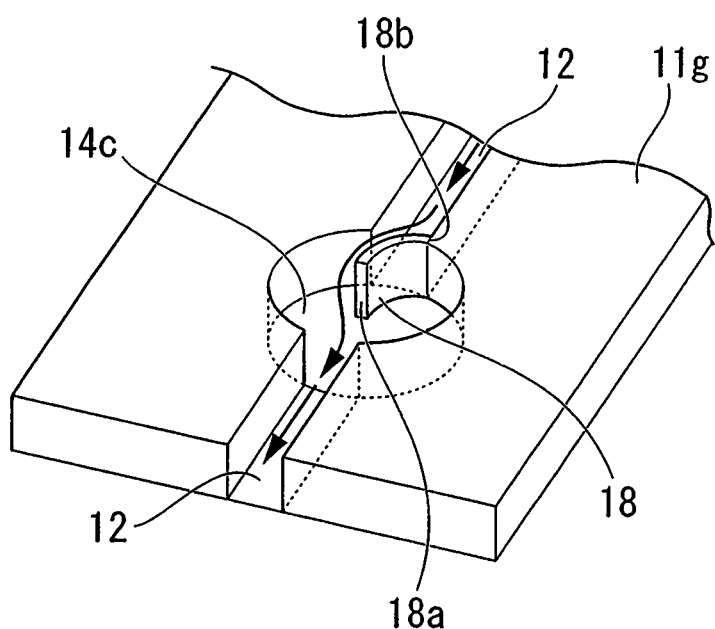
FIG. 11 is a perspective view in which a portion of the base plate of the liquid channel device in FIG. 10A, 10B is enlarged.

In this embodiment, as shown in FIG. 11, a dam plate 18 is formed as a reverse flow check in the inner layer 11g. In the dam plate 18 in this embodiment, the base end 18b is fixed to one side wall of the liquid channel 12 and the distal end 18a and the lateral ends are not fixed in place, so that the distal end 18a of the dam plate 18 is directed downstream at the boundary of the metering chamber 14c and the liquid channel 12 upstream there from.

For this reason, when the liquid is transported from the upstream filter chamber, not shown, into the metering chamber 14c, the liquid surpasses the distal end 18a of the dam plate 18 and can flow into the metering chamber 14c. When the liquid transport P1' of the metering chamber 14c operates, the liquid inside the metering chamber 14c can only flow downstream, and cannot undergo reverse flow upstream, due to the action of the dam plate 18.

Figure 12:
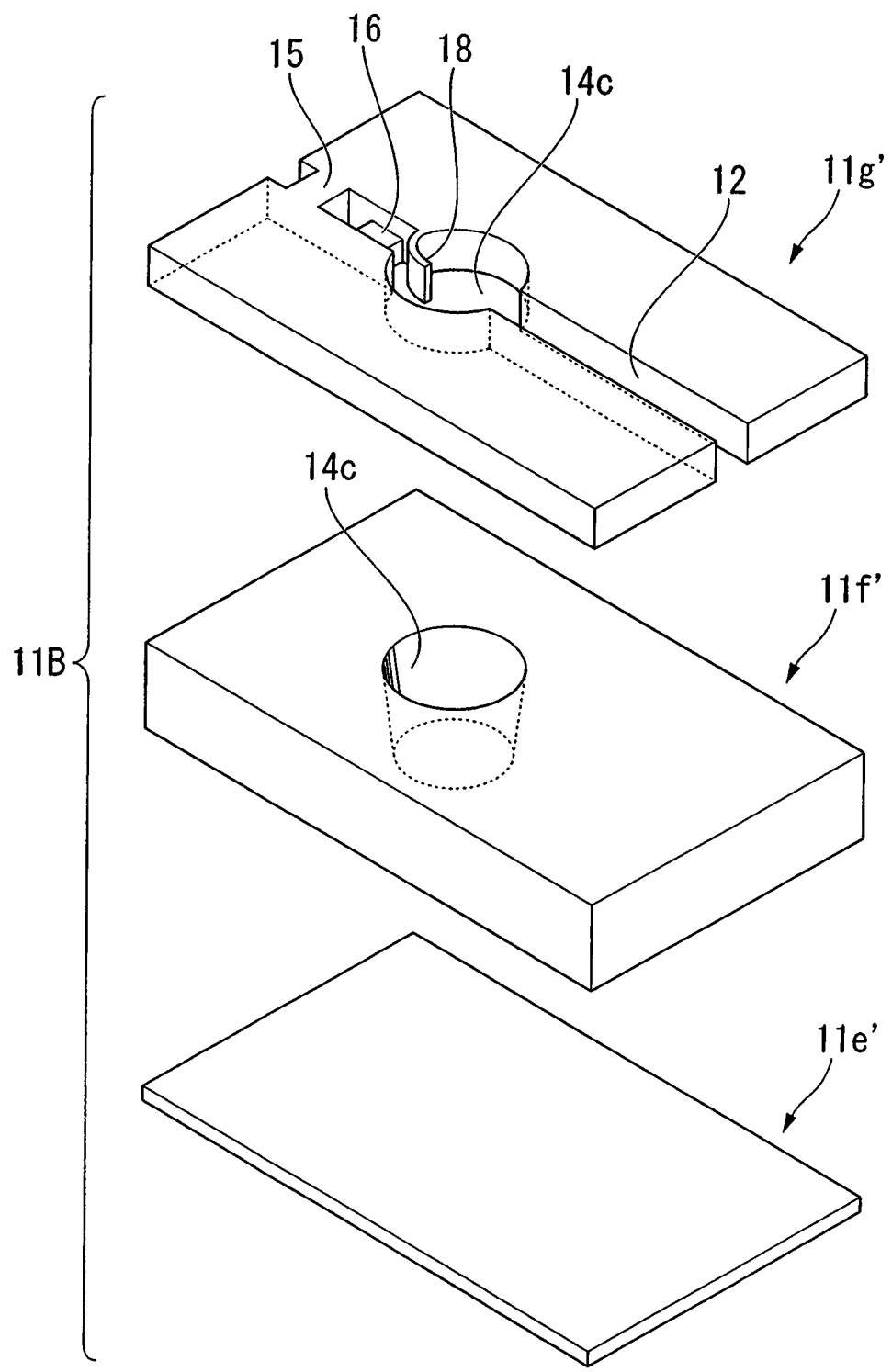
FIG. 12 is a schematic view showing the production process of the base plate of the liquid channel device in FIGS. 10A and 10B.

The base plate 11B of this embodiment can be formed as shown in FIG. 12. First, the sheet 11g' for forming the inner layer 11g is prepared in advance. The site corresponding to the liquid channel 12 in this sheet 11g' is punched out in a linear form, and the area corresponding to the top part of the liquid chamber is punched out in the shape of a hole. Further, in this case, the areas forming the first convex section 15 and the second convex section 16 are not punched out but rather are left remaining, and polishing or the like is employed to adjust the height of the second convex section 16 so that the height of the second convex section 16 is less than that of the first convex section 15. Further, in this embodiment, the dam plate 18 is also formed from the inner layer 11$g$, so that the area forming the dam plate 18 is not punched out but is left remaining in the sheet 11$g'$.

The sheet 11$f'$ for forming the middle layer 11$f$ is prepared in advance. The sites corresponding to the bottom parts of the metering chamber 14$c$ and the other chambers are punched out in the form of a hole in the sheet 11$f$.

Next, the sheet 11$e'$ forming the outer layer 11$e$ is prepared in advance, and the sheet 11$f'$ forming the middle layer 11$f$ and the sheet 11$g'$ forming the inner layer 11$g$ are laminated and adhered to the sheet 11$e'$, thereby forming the base plate 11B as a result.

For the material for the various sheets 11$e'$, 11$f'$, 11$g'$, a selection may be made from among the materials employed for the base plate 11A exemplified in the first embodiment. In particular, the sheet 11$e'$ forms the floor of the liquid chamber and is subjected to external pressing during operation of the liquid transport section. Accordingly, it is necessary to use a material having flexibility.

In addition, the thickness of the sheet 11$g'$ corresponds to the depth of the liquid channel 12 which is formed, with the sum of the thicknesses of the sheet 11$g'$ and the sheet 11$f'$ corresponding to the total depth of the liquid chamber. Thus, the thicknesses of the sheet 11$f'$ and the sheet 11$g'$ is determined after taking into consideration the depth which is obtained for the liquid chamber and the liquid channel 12. The depth of the liquid chamber may be suitably set in response to the required capacity. Further, the optimal depth of the liquid channel 12 is within the same range as in the first embodiment. The sheet 11$e'$ is required to bend during the operation of the transport section as described above. Accordingly, while it will depend on the material, a value in the range of 20~300 μm is ideal.

The base plate 11B may be formed from two layers consisting of outer layer 11$e$ and inner layer 11$g$, in which the sheet 11$e'$ and the sheet 11$g'$ are laminated. In this case, the depth of the liquid channel 12 and liquid chamber are the same.

Figure 13:
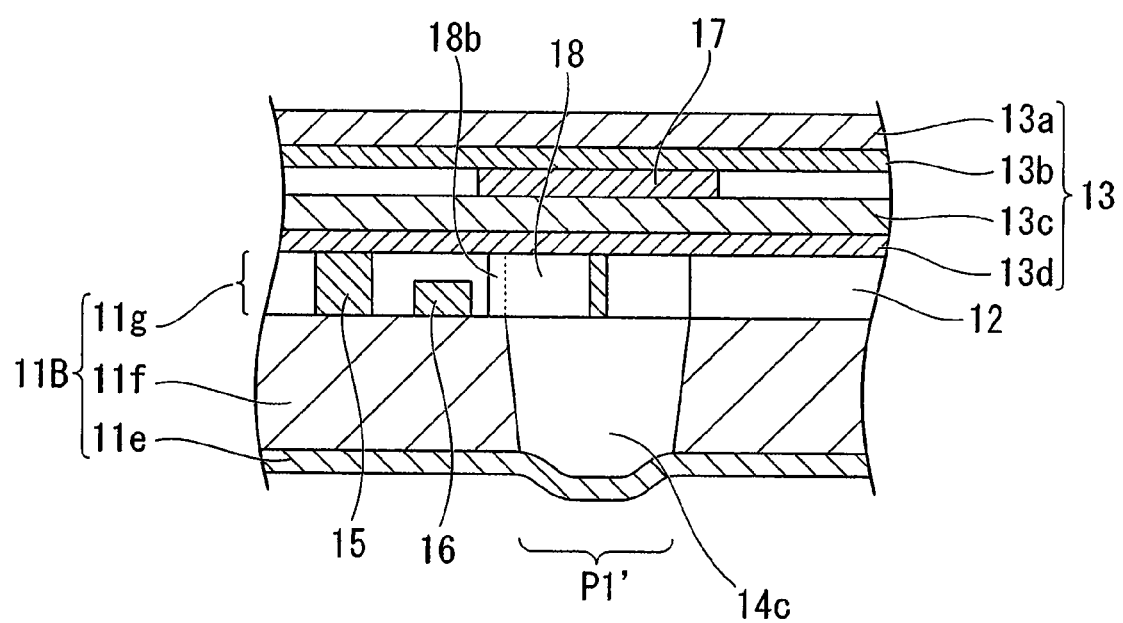
FIG. 13 is a cross-sectional view showing another embodiment of the base plate of the liquid channel device according to the third embodiment.

In the liquid channel device 10C according to this embodiment, in order to more effectively operate the liquid transport section P1', the outer layer 11$e$ of the base plate 11B in the area corresponding to the metering chamber 14$c$, i.e., the floor of the metering chamber 14$c$, may be expanded in the outer direction, as shown in FIG. 13. By expanding the floor in this way, the internal capacity of the metering chamber 14$c$ can be further decreased when pressing this area inward in the case where operating the liquid transport section P1'. As a result, the liquid in the metering chamber 14$c$ can be more effectively transported.

The liquid channel device 10C according to the third embodiment can be obtained by providing a cover plate 13 with the same design as in the first embodiment to this type of base plate 11B. Namely, in this embodiment, as shown in FIG. 10A and FIG. 10B, the strongly adhered layer 13$b$ and the second base layer 13$c$ are not separated from one another in the cover plate 13 at the area corresponding to the metering chamber 14$c$. Rather, a spacer 17 is interposed, and the spacer 17 and the strongly adhered layer 13$b$ are adhered and the layers are tightly formed. For this reason, when external pressing is applied to the floor of the metering chamber 14$c$ and the floor bends, causing the liquid transport section P1' to operate, the internal capacity of the metering chamber 14$c$ is decreased and the function as a liquid transport section is realized. Here, hypothetically, if there was a space of separation between the strongly adhered layer 13$b$ and the second base layer 13$c$ and the spacer 17 was not interposed so that the layers were not tight, then the second base layer 13$c$ and the weakly adhered layer 13$d$ would not bend toward the outside based on the inner pressure of the metering chamber 14$c$ when external pressing is applied to the floor of the metering chamber 14$c$. Thus, the internal capacity of the metering chamber 14$c$ would not decrease, and it is possible that the effect as the liquid transport section could not be realized.

In a liquid channel device 10C of this type, base plate 11B is made of three layers, namely the outer layer 11$e$, the middle layer 11$f$ and the inner layer 11$g$, or two layers, namely the outer layer 11$e$ and the inner layer 11$g$. The liquid chambers, liquid channel 12, dam plate 18, first convex section 15 and second convex section 16 are formed by punching out sheet 11$f'$ which forms the middle layer 11$f$ and sheet 11$g'$ which forms the inner layer 11$g$. For this reason, the liquid chambers, etc. can be formed simply and at low production cost, enabling large volume production, as compared to a method in which photolithography or the like is employed to form the liquid chamber and liquid channel to a base plate made of a single flat plate, or a method for molding a base plate in which the liquid chamber and liquid channel are formed using injection molding.

Note that the first through third embodiments explained above show as examples liquid channel devices 10A, 10B, 10C in which the liquid channel 12 is formed to only one side of the base plates 11A, 11B. However, the liquid channel 12 may be formed to both sides of the base plates 11A, 11B.

There are no restrictions on the arrangement for the communicating holes which can be opened/closed which are provided to the various liquid chambers. Namely, an embodiment is acceptable in which the communicating holes can be opened and closed by removing and placing an engageable cap in the communicating holes formed in the cover plate. It is also acceptable to provide opening sections and a closing section having the same structure as the opening sections S1~S7 and the closing section T1 provided to the liquid channel 12.

In the case where a base plate 11A is made of a single flat plate as in the first embodiment, it is acceptable to provide a liquid transport section to the liquid chamber which is operated by pressing the floor of the liquid chamber. When the base plate 11B is formed from a plurality of layers as in the third embodiment, a liquid transport section which is operated by pressing the cover plate 13 corresponding to the liquid chamber may be provided to the liquid chamber. Further, the explanation above employed the example of a liquid channel device provided with a closing section and opening sections, and therefore exemplified a design for the cover plate 13 comprising the first base layer 13$a$, strongly adhered layer 13$b$, second base layer 13$c$, weakly adhered layer 13$d$ and spacer 17. However, it is not necessary for the cover plate 13 to be formed of a plurality of layers in this way in order to actuate the liquid transfer section. Rather, it is also acceptable if cover plate 13 is comprised of a single layer.

Further, the preceding example illustrated an embodiment which utilized gravitational force and the action of a liquid transport section in order to cause the liquid to flow. However, it is also acceptable to incorporate a method for causing movement and flow of the liquid by heating the liquid channel 12, a portion of the liquid chamber, or both to expand the air inside the liquid channel 12 or inside the liquid chamber, or a method for causing movement and flow of the liquid by sealing an oxygen absorbing agent (such as readily oxidizable iron powder, etc.) inside a portion of the liquid channel 12 and causing a reduction in the pressure inside the liquid channel 12 due to absorption of the oxygen within.

In the preceding explanation, a method in which the cover plate 13 was pierced with a syringe needle was employed as an example of a method for injecting a sample into the sample introduction chamber 14a. For example, a sample injection hole may be formed in the cover plate 13 in advance, with the sample then injected through this hole. In this case, the sample injection hole may be covered with a protective tape and the injection may be carried out by piercing the protective tape with the syringe, or the protective tape may be peeled away and the injection carried out by inserting the syringe into the sample injection hole.

From the perspective of preventing contamination, etc., it is preferable that the communicating holes provided in the various liquid chambers be sealed prior to the use of the liquid channel devices 11A, 11B, and then opened at the time of use. Thus, opening sections of the same design as the opening sections S1~14 may be provided to the liquid channel 12 in front of the communicating holes.

Further, in the above discussion, explanations were made of methods for causing the liquid to flow by utilizing gravitational force in the liquid channel device 10A and employing centrifugal force in the liquid channel device 10B, respectively. However, the present invention is not limited thereto. For example, it is also acceptable to employ a method for causing movement and flow of the liquid by, for example, pressurizing a portion of the liquid channel 12, expanding the air inside the liquid channel 12 by heating part of the liquid channel 12, or reducing the pressure inside the liquid channel 12 by introducing an oxygen absorbing agent (readily oxidizable iron powder, etc.) to a portion of the liquid channel 12 and absorbing the oxygen inside the liquid channel 12. Further, it is also acceptable to pressurize, heat or reduce the pressure of the metering chamber 14 rather than a portion of the liquid channel 12, or, depending on the circumstances, to pressurize, heat or reduce the pressure of both the metering chamber 14 and the liquid channel 12.

The sample and reagent that flow through the liquid channel devices 10A, 10B are not particularly restricted. Samples and reagents that are conventionally employed in the medical and environmental fields as well as others, may be suitably combined in use. For example, such biological derivatives as blood (whole blood), plasma, serum, buffy coat, urine, stercus, saliva, sputum or the like, as well as viruses, or bacterial, mold, yeast, or plant cells, may be cited.

It is also acceptable to employ DNA or RNA isolated from these products. Alternatively, it is also acceptable to employ as a sample the products obtained by performing any kind of pre-treatment or dilution on the preceding. In the case where analyzing for the presence of an antigen in the sample, it is preferable to use a reagent which includes an antibody to the antigen.

As a detecting and analyzing section for the measured liquid formulated by the liquid channel devices 10A, 10B, a conventionally known photochemical means, electrical means or the like may be suitably employed.

Fourth Embodiment

Figure 14:
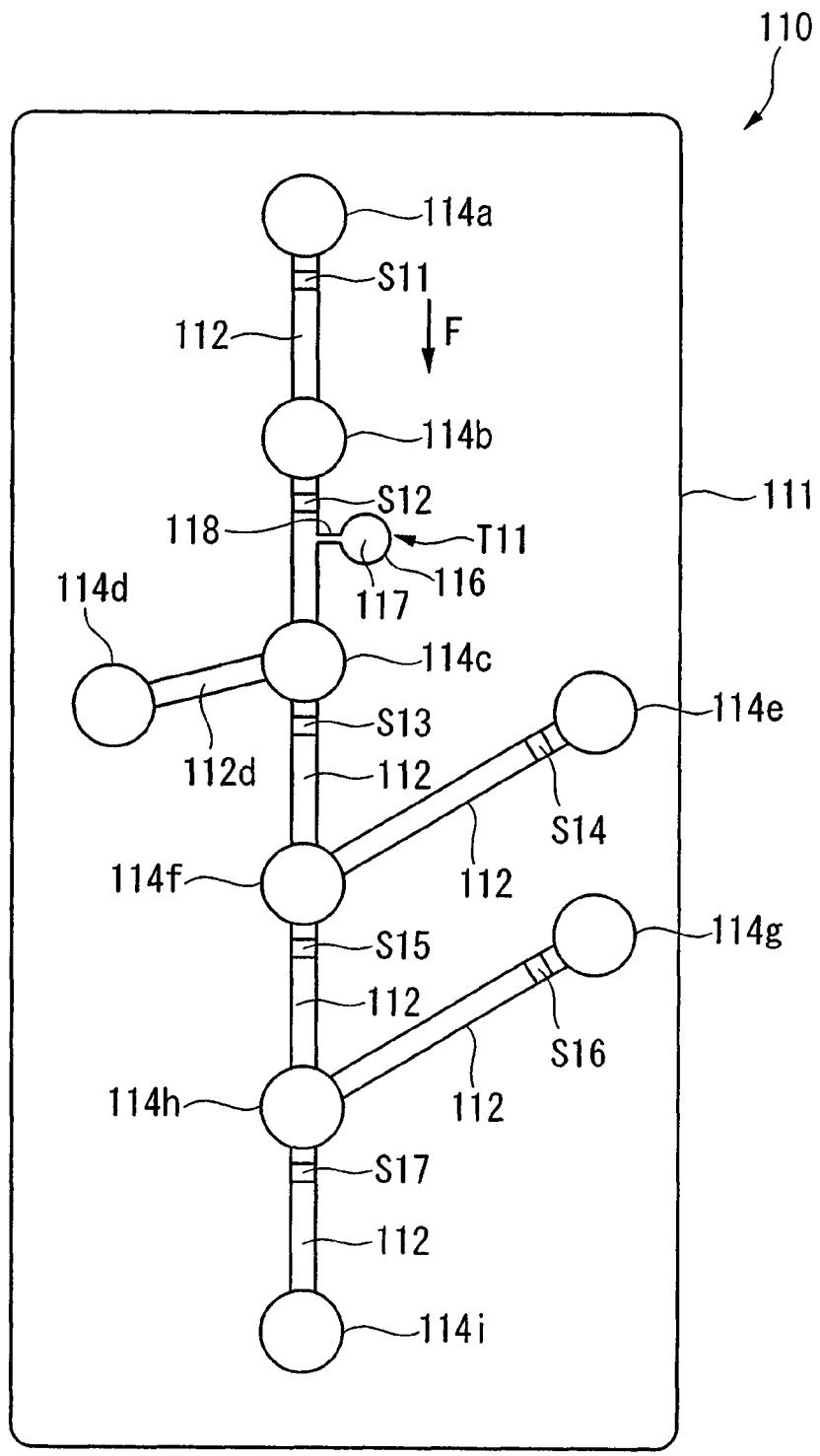
FIG. 14 is a schematic planar perspective view showing the liquid channel device according to a fourth embodiment of the present invention.
Figure 15:
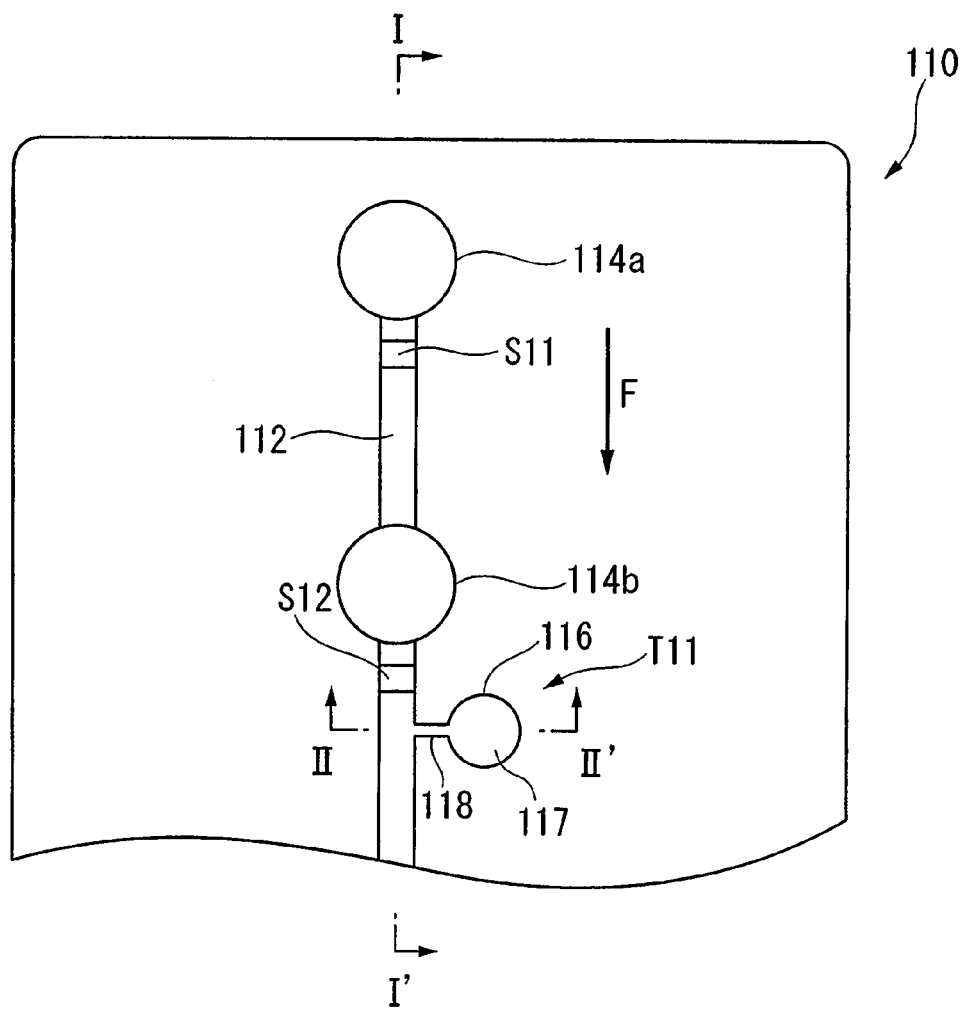
FIG. 15 is a planar perspective view showing an expanded view of a portion of the liquid channel device in FIG. 14.
Figure 16:
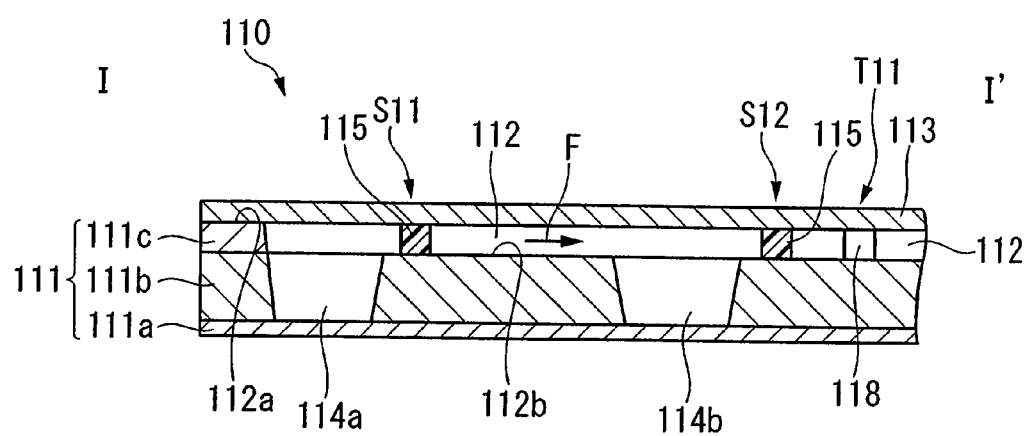
FIG. 16 is a cross-sectional view along the line I-I' in FIG. 15.

FIG. 14 is a planar perspective view schematically showing the liquid channel device according to a fourth embodiment. FIG. 15 is a planar perspective view showing an expanded view of part of the liquid channel device in FIG. 14. FIG. 16 is a cross-sectional view along the line I-I' in FIG. 15.

In this liquid channel device 110, a groove-like liquid channel 112, through which a liquid being at least one of either a sample and a reagent flows, and a plurality (9 in this embodiment) of liquid chambers (114a~114i) for holding the liquid at the ends of or along the liquid channel 112, are formed to at least one side of a flat square base plate 111, and a cover plate 113 is laminated to the channel formation surface 112a of base plate 111 on which the liquid channel 112 is formed. When the upper end of the liquid channel device 110 is positioned in the upward direction and the lower end of the liquid channel device 110 is positioned in the downward direction as shown in FIG. 14, then the sample flows under the force of gravity from the upstream end to the downstream end of the liquid channel 112 in the direction indicated by arrow F. A variety of treatments and mixing with reagents may be carried out to the sample along the way, to formulate the measured liquid that is supplied for various detection and analyses.

In other words, a sample introduction chamber 114a, in which the introduced sample is held, is provided at the upstream end of the liquid channel 112, and a filtering chamber 114b, which houses a filter not shown in the figures and carries out filtering of sample which has flowed from the sample introduction chamber 114a, is provided downstream from the sample introduction chamber 114a.

A metering chamber 114c for quantification of a fixed amount of filtered sample is provided downstream from the filtering chamber 114b. An overflow section including an overflow path 112d and a waste solution chamber 114d provided downstream from the overflow path 112d, is provided to the metering chamber 114c in this embodiment. Sample which exceeds a fixed quantity at the metering chamber 114c, overflows, flowing through the overflow path 112d and into the waste solution chamber 114d. As a result, a fixed quantity of sample can be quantified at the metering chamber 114c.

A first mixing chamber 114f is provided downstream from the metering chamber 114c. The first mixing chamber 114f is for mixing the sample quantified at the metering chamber 114c and a liquid first reagent, a specific quantity of which has been sealed into the first reagent chamber 114e in advance. A second mixing chamber 114h is provided downstream from the mixing chamber 114f. The second mixing chamber 114h is for mixing the intermediate solution formulated at first mixing chamber 114f and a liquid second reagent, a specific quantity of which has been sealed into the second reagent chamber 114g in advance.

A measuring chamber 114i is provided downstream from the second mixing chamber 114h (at the downstream end of the liquid channel 112). The measured liquid formulated at the second mixing chamber 114h is held in the measuring chamber 114i, and detection and analyses of the various components is carried out by an analyzing and detecting section not shown in the figures.

Note that opening/closing communicating holes, not shown in the figures, which communicate with the outside environment, are provided as needed to each liquid chamber.

As shown in FIG. 16, the base plate 111 of the liquid channel device 110 includes three layers, namely, an outer layer 111a, an middle layer 111b laminated to the inside of the outer layer 111a, and an inner layer 111c laminated to the inside of the middle layer 111b.

The top part (cover plate 113 side) of the liquid chamber (FIG. 3 shows only the sample introduction chamber 114a and the filtering chamber 114b) and the liquid channel 112 are formed to the inner layer 111c. The bottom part of the liquid chamber (the section on the floor side of the liquid chamber, excluding the aforementioned top part) is formed to the middle layer 111b. In the middle layer 111b, the surface on the inner layer 111c side forms the floor 112b of the liquid channel 112. The outer layer 111a is disposed to the outermost side of the base plate 111, and the surface of the outer layer 111a that is on the middle layer 111b side forms the floor of the liquid chamber.

This liquid channel device 110 is provided with opening sections S11~S17 for opening a portion of the liquid channel 112 from the closed mode, and a closing section T11 for closing a portion of the liquid channel 112 from the open mode.

In this embodiment, one opening section S11~S17 is disposed to each of the various liquid channels 112 between, respectively, the sample introduction chamber 114a and the filtering chamber 114b; the filtering chamber 114b and the metering chamber 114c; the metering chamber 114c and the first mixing chamber 114f; then first mixing chamber 114f and the second mixing chamber 114h; the first reagent chamber 114e and the first mixing chamber 114f; the second reagent chamber 114g and the second mixing chamber 114h; and the second mixing chamber 114h and the measuring chamber 114i.

The closing section T11 is provided farther downstream than the opening section S12 on the liquid channel 112 that is between the filtering chamber 114b and the metering chamber 114c.

As exemplified by S11 and S12 in FIG. 16, the opening sections S11~S17 are formed by a resin stopper 115 which is designed to stop the flow of liquid when disposed inside the liquid channel 112 so as to cover a portion of the liquid channel 112, thereby closing this portion of the liquid channel 112. This stopper 115 is made of a plastically deformable resin. The stopper 115 undergoes plastic deformation by external pressing on the cover plate 113 in the area where the stopper 115 is disposed, opening the liquid channel 112 from the closed mode.

Figure 17A:
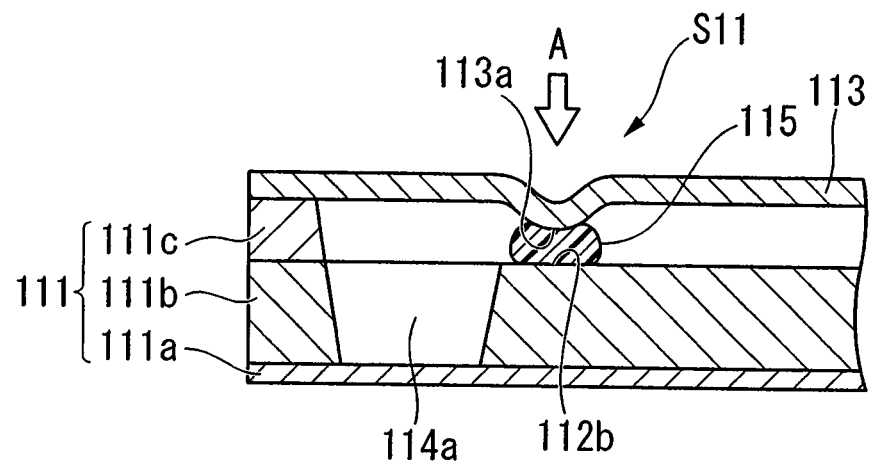
FIG. 17A is a view for explaining the condition when the opening part operates in the liquid channel device in FIG. 14, and is a cross-sectional view showing the state when a weight is applied to the stopper.
Figure 17B:
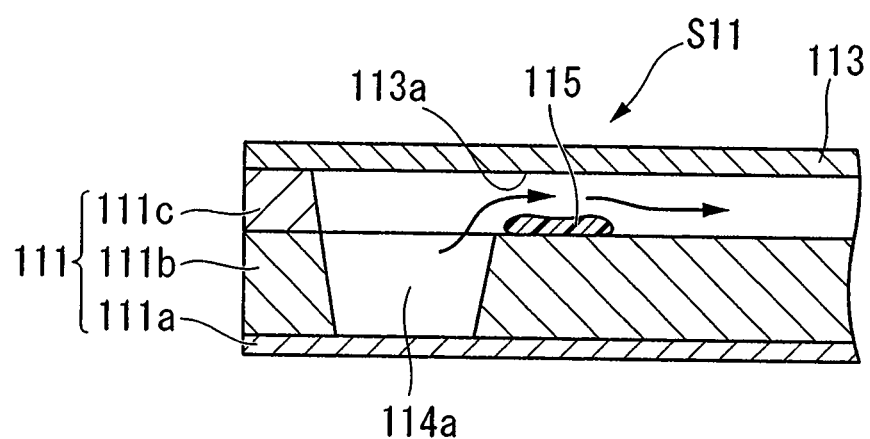
FIG. 17B is a view for explaining the condition when the opening part operates in the liquid channel device in FIG. 14, and is a cross-sectional view showing the state when a weight is removed.

Specifically, as shown by the opening section S11 exemplified in FIGS. 17A and 17B, when a load is applied by pressing in the direction of arrow A from the outside of the cover plate 113 on the stopper 115 which forms the opening section S11, the cover plate 113 bends as shown in FIG. 17A, and the stopper 115 which contacts with the cover plate 113 is pressed down and undergoes plastic deformation to become flat. When the load is subsequently removed, then, as shown in FIG. 17B, the cover plate 113 is restored to its original state due to its restorative force. However, the stopper 115 does not undergo restoration but remains in the flat deformed state. As a result, the space between the stopper 115 and the cover plate 113 is again separates, enabling the liquid to flow through.

In the thus-designed opening sections S11~S17, when a load is applied by applying pressure to the stopper 115 from the outside of the cover plate 113, the space between the stopper 115 and the cover plate 113, which had been very closely adhered, separates due to the pressing to remove the load. As a result, the liquid channel 112 in this area opens from the closed state.

Figure 18:
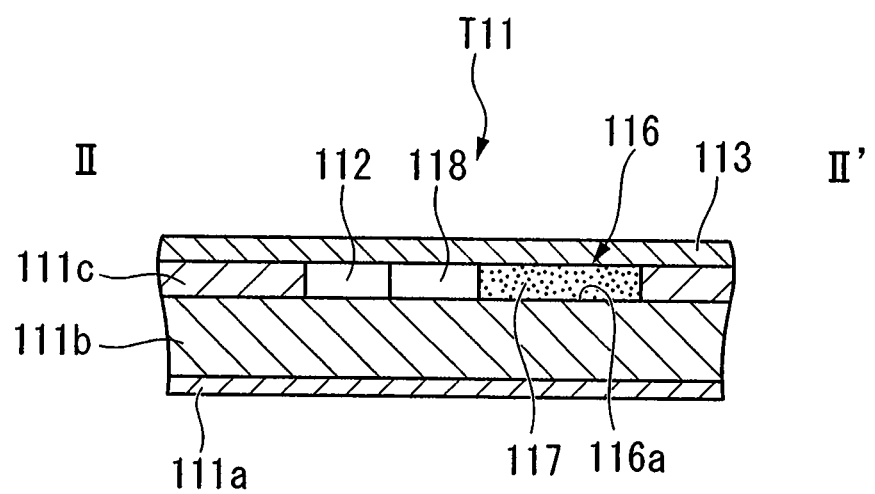
FIG. 18 is a cross-sectional view along the line II-II' in FIG. 15.

As shown in FIG. 18, the closing section T11 of the liquid channel device 110 is provided with a sealing material supply chamber 116 which is formed to the base plate 111 and branches from the liquid channel 112, and a paste-like sealing material 117 which fills this sealing material supply chamber 116.

Figure 19A:
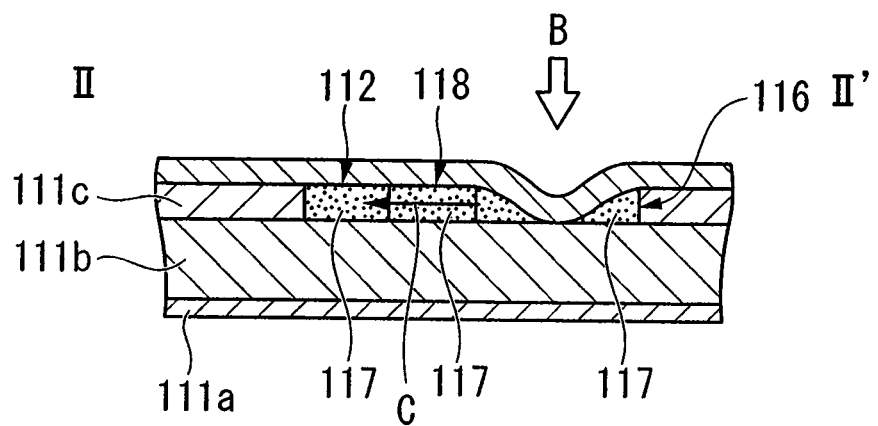
FIG. 19A is a view for explaining the condition when the closing part operates in the liquid channel device in FIG. 14, and is a cross-sectional view showing the state when the sealing material is pressed out.
Figure 19B:
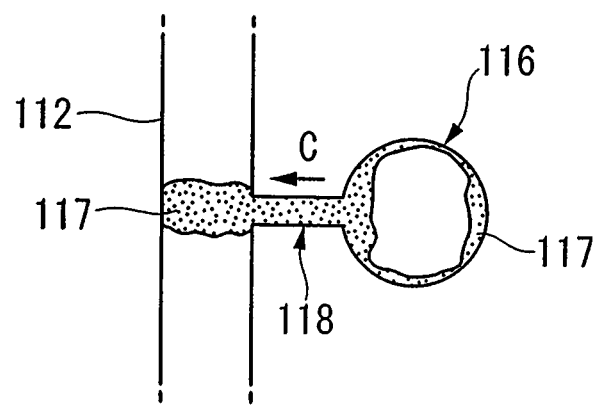
FIG. 19B is a view for explaining the condition when the closing part operates in the liquid channel device in FIG. 14, and is a planar view.

As shown by the cross-sectional view in FIG. 19A and the planar view in FIG. 19B, by applying external pressing on the cover plate 113 in the area corresponding to the sealing material supply chamber 116, this sealing material 117 passes through a supply channel 118 which is connected to the sealing material supply chamber 116 and the liquid channel 112, and is extruded out into the liquid channel 112, thereby closing this section from the open mode.

Specifically, when a load is applied by pressing from the outside on the cover plate 113 in the area corresponding to the sealing material supply chamber 116 as shown by arrow B, the cover plate 13 bends. As a result, as shown by arrow C, the sealing material 117 which fills the sealing material supply chamber 116 is extruded out into the liquid channel 112 via the supply channel 118. As a result, the liquid channel 112 is closed by the extruded sealing material 117, so that the liquid cannot flow through this section.

Note that in the case of a liquid channel device that can close from the open mode, the sealing material supply chamber 116 and the liquid channel 112 communicate via the supply channel 118. In this case as well, it is acceptable to have the sealing material supply chamber 116 and the liquid channel 112 directly communicate without forming the supply channel 118.

As a specific example of a method for formulating the measured liquid using this type of liquid channel device 110, an arrangement is provided in which the liquid channel device 110 is positioned so that the sample introduction chamber 114a side is directed upward and the measuring chamber 114i side is directed downward, so as to facilitate the flow of liquid from upstream to downstream under the force of gravity.

Next, the sample is sampled with a syringe, and the cover plate 113 in the area corresponding to the sample introduction chamber 114 is pierced with the needle of the syringe and the sample is injected into the sample introduction chamber 114a. Thereafter, the opening section S11 provided in between the sample introduction chamber 114a and the filtering chamber 114b, i.e., the liquid channel 112 in the area where the stopper 115 undergoes plastic deformation due to external pressing on the outside of the cover plate 113, opens, and the sample is introduced under the force of gravity into the filtering chamber 114b.

In this case, the pressing operation may be carried out manually by the operator pressing with his finger. Alternatively, a specific site may be pressed by employing a pressing device in which the pressing position has been programmed in advance as XY coordinates.

Once the filtering has been completed at the filtering chamber 114b, the stopper 115 of the opening sections S12 which is provided in between the filtering chamber 114b and the metering chamber 114c undergoes plastic deformation in the same manner. The liquid channel 112 in this area opens, and the sample is introduced into the metering chamber 114c under the force of gravity.

In the metering chamber 114c, once it is confirmed that the introduced liquid has begun to overflow, the closing section T11 which is provided in between the filtering chamber 114b and the metering chamber 114c is operated, and the liquid channel 112 in this area is closed. Specifically, the cover plate 113 in the area corresponding to the sealing material supply chamber 116 is pressed as shown by arrow B to apply a load. The sealing material 117 which fills the sealing material supply chamber 116 is extruded out into the liquid channel 112, and the liquid channel 112 in this area is closed.

In this way, the liquid from upstream is prevented from flowing into the metering chamber 114c, and the opening section S13 which is provided downstream from the metering chamber 114c is operated so that the sample quantified at the metering chamber 114c is introduced into the first mixing chamber 114f.

The thus-quantified sample is introduced into the first mixing chamber 114f. The opening section S14 which is in between the first reagent chamber 114e and the first mixing chamber 114f is subjected to plastic deformation in the same manner as the stopper, to introduce the first reagent into the first mixing chamber 114f. The sample is then mixed with the first reagent in the first mixing chamber 114f, to formulate an intermediate solution.

The opening section S15 which is in between the first mixing chamber 114f and the second mixing chamber 114h is subjected to plastic deformation in the same manner as the stopper, to introduce the intermediate solution produced at first mixing chamber 114f into the second mixing chamber 114h. The opening section S16 which is in between the second reagent chamber 114g and the second mixing chamber 114h is subjected to plastic deformation in the same manner as the stopper, to introduce the second reagent into the second mixing chamber 114h. The intermediate solution and the second reagent are mixed in the second mixing chamber 114h, to formulate the measured liquid.

The opening section S17 which is in between the second mixing chamber 114h and the measuring chamber 114i is subjected to plastic deformation in the same manner as the stopper, to introduce the measured liquid formulated in the second mixing chamber 114h into the measuring chamber 114i.

Once the measured liquid is introduced into the measuring chamber 114i, each liquid channel device 110 is supplied to a detecting and analyzing section, and detection and measurement of the target components is carried out.

It is acceptable to control the flow of liquid, so that it flows more easily or the accuracy of the flow volume is improved for example, during the process for formulating the measured liquid in this way, by suitably opening and closing as needed the communicating holes, not shown in the figures, which are provided to the various chambers.

This type of liquid channel device 110 has opening sections S11~S17 for opening the liquid channel 112 from the closed mode, and a closing section T11 for closing the liquid channel 112 from the open mode. As a result, it is possible to control the flow of the liquid in the liquid channel 112. As a result, highly accurate detection and analysis can be carried out in a short period of time.

For example, in this embodiment, the closing section T11 is provided upstream and the opening section S13 is provided downstream from the metering chamber 114c. For this reason, the sample can be quickly and accurately quantified at the metering chamber 114c, and introduced into the first mixing chamber 114f. If, hypothetically, the opening section S13 is not provided downstream from the metering chamber 114c here, then the liquid channel 112 in this section is continuously in the open state. As a result, the sample continuously flows out from the metering chamber 114c even during quantification, so that so that a constant amount of sample cannot be retained. Thus, quantification itself becomes impossible. When the closing section T11 is not provided upstream from the metering chamber 114c, then it is necessary to introduce the quantified sample into the first mixing chamber 114f by operating the opening section S13 in between the metering chamber 114c and the first mixing chamber 114f after the entire amount of sample which has passed through the filtering chamber 114b has completely finished flowing into the metering chamber 114c. In this case, when the sample is a liquid having viscosity, such as blood, then time is required for the entire sample which has passed through the filter to completely enter the metering chamber 114c. Thus, it becomes difficult to carry out quantification within a short period to time. By providing the closing section T11 to the upstream side of the metering chamber 114c as in this embodiment, then, even if the entire sample which has passed through the filtering chamber 114b is not completely finished flowing into the metering chamber 114c, it is possible to operate the closing section T11 once the sample begins to overflow at metering chamber 114c, so that further introduction of the sample into the metering chamber 114c can be prevented. Thus, an accurate quantification can be carried out in a short period of time.

Further, in this embodiment, the opening section S15 is provided in between the first mixing chamber 114f and the second mixing chamber 114h, and an opening section S17 is provided in between the second mixing chamber 114h and the measuring chamber 114i. For this reason, the desired mixing and reactions can be sufficiently carried out in the first mixing chamber 114f and the second mixing chamber 114h, after which the opening sections S15, S17 are opened, allowing the intermediate solution and the measured liquid to be introduced into the second mixing chamber 114h and the measuring chamber 114i. Thus, it is possible to prevent a deterioration in the accuracy of detection and analysis that is caused when the mixing or reaction is insufficient.

In this embodiment, the opening sections S14, S16 are provided in between the first reagent chamber 114e and the first mixing chamber 114f, and the second reagent chamber 114g and the second mixing chamber 114h. For this reason, these opening sections can be opened at the desired time, enabling the first reagent and the second reagent, which were sealed in advance in the first reagent chamber 114e and the second reagent chamber 114g, to be introduced into the first mixing chamber 114f and the second mixing chamber 114h. If, hypothetically, the opening sections S14, S16 were not provided, then there is a concern that the first regent and the second reagent would begin to flow downstream during maintenance, etc. of the liquid channel device 110.

Moreover, the opening sections S11~S17 and the closing section T11 of the liquid channel device 110 of this embodiment have a simple construction and can be formed at low cost. Thus, liquid channel device 110 can be made to be a disposable type. Further, the opening and closing operation is accomplished by means of simple pressing. Thus, operability is superior.

This type of liquid channel device 110 can be produced by a method provided with a first step of forming the liquid channel 112, the liquid chamber, the sealing material supply chamber 116, and the supply channel 118 to the base plate 111; a second step of forming the stopper 115 at a specific position on the formed liquid channel 112; and a third step of laminating the cover plate 113 to the channel formation surface 112a which is on the side of base plate 111 where the liquid channel 112, etc. is formed.

Note that in the case where the liquid channel device is able to close from the open mode, then the second step differs from that above and is for filling the formed sealing material supply chamber 116 with a sealing material.

The steps for producing the liquid channel device 110 will be explained by further referencing FIG. 20, which schematically shows the steps for producing the liquid channel device 110.

In the first step, a roll 120 of sheet 111c' which forms the inner layer 111c of the base plate 111, a roll 121 of sheet 111b' which forms the middle layer 111b of the base plate 111, and a roll 122 of sheet 111a' which forms the outer layer 111a of the base plate 111, are prepared.

Next, sheet 111c' is continuously supplied from roll 120 of sheet 111c' forming the inner layer 111c, and a die-cutter 123a is used to punch out a linear form at the site corresponding to the liquid channel 112, and punch out a hole at the area corresponding to the top part of metering chamber 114c and the other various liquid chambers. Forms are punched out in the sheet 111c' at the sites corresponding to the supply channel 118 and the sealing material supply chamber 116 in order to provide this liquid channel device 110 with a sealing material supply chamber 116 and a supply channel 118 formed branching off from part of the liquid channel 112.

Next, sheet 111b' is continuously supplied from roll the 121 of the sheet 111b' forming the middle layer 111b, and a die-cutter 123b is employed to punch out holes at the sites corresponding to the bottom part of the metering chamber 114c and the other various liquid chambers.

Next, sheet 111a' is continuously supplied from roll 122 of sheet 111a' forming the outer layer 111a. Next, the various sheets 111a', 111b' and 111c' are sequentially laminated to form the base plate 111.

Here, it is preferable that the various sheets 111a', 111b', and 111c' be adhered together by means of an adhesive supplied from an adhesive supplying device not shown in the figures. However, depending on the material of the various sheets 111a', 111b' and 111c', it is also acceptable to stick the sheets together using heat fusion or the like. In addition, it is also acceptable to employ a sheet coated with an adhesive or the like.

A process is employed for the first step in this way in which the various sheets 111a', 111b', and 111c' from respective rolls 120, 121, and 122 are supplied, punch-outs in respective specific shapes are formed in sheets 111b' and 111c', and these sheets 111a', 111b' and 111c' are sequentially laminated and adhered. As a result, it is possible to continuously produce multiple base plates 111 in which a liquid channel 112 and liquid chambers are formed. This type of method has reduced production costs and enables large scale production easily as compared to a method in which, for example, lithography or machining, is used to form the liquid chambers and liquid channel in respective base plates comprising a single flat base plate, or a method in which injection molding or the like is used to form a base plate in which liquid chambers and a liquid channel are formed. Accordingly, this method is ideal from an industrial perspective.

Note that a method in which specific shapes are punched out in sheets 111b' and 111c' to form the liquid channel 112 and the liquid chambers, etc., is low cost and superior in productivity. However, it is also acceptable to use other methods (lasering, drilling using a knife, etc., heating) to form the liquid channel 112 and liquid chambers by opening specific shapes in the sheets 111b' and 111c'.

Further, this embodiment shows a three-layer design for the base layer 111 of the liquid channel device 110 comprising the outer layer 111a, the middle layer 111b, and the inner layer 111c. However, it is also acceptable to employ a two layer design comprising the outer layer 111a and the inner layer 111c. In this case, the liquid channel 112, liquid chambers, supply channel 118, and sealing material supply chamber 116 are formed to the sheet 111c' forming the inner layer 111c. In this case, the depth of the liquid chambers and the liquid channel 112 formed are the same.

The sealing material supply chamber 116 is formed to the sheet 111c' which forms the inner layer 111c. However, particularly in the case of a liquid channel device which can close from the open mode, the top part of the sealing material supply chamber may be formed to the sheet 111c' which forms the inner layer 111c, the bottom part of the sealing material supply chamber may be formed to the sheet 111b' which forms the middle layer 111b, and the sealing material supply chamber may be formed to have the same depth as the liquid chambers.

Examples of materials for the various sheets 111a', 111b', and 111c' forming the outer layer 111a, the middle layer 111b, and the inner layer 111c of the base plate 111 include such resins as styrene resin, acrylic resin, polycarbonate resin, vinyl chloride resin, PEN resin, polyester resin, epoxy resin, phenol resin, ABS resin, polypropylene resin, fiber-reinforced plastic or the like. Among these, styrene resin, acrylic resin, polycarbonate resin, vinyl chloride resin, PEN resin, and polyester resin are preferred because they are transparent and enable visual inspection of the condition of the liquid flowing through the liquid channel 112.

Note that in this embodiment, examples of resins were disclosed for the sheet material in order to explain an optimal method for producing a liquid channel device 110 when employing a resin roll as the base plate 111. However, the production method is not particularly restricted. For example, when it is necessary to stably support the liquid channel device, then a non-resin transparent material, such as a glass plate, may be employed for the base plate, and a method such as machining may be applied to this material to form the liquid channel and the liquid chambers.

The thickness of the various sheets 111a', 111b', and 111c' can be suitably designed. However, in the case of the liquid channel device 110 in the figures, the thickness of the sheet 111c' forming the inner layer 111c corresponds to the depth of the liquid channel 112 which is formed, and the sum of the thicknesses of the sheet 111c' forming the inner layer 111c and the sheet 111b' forming the middle layer 111b corresponds to the total depth of the liquid chambers. Thus, the thicknesses of the sheet 111b' and sheet 111c' are determined after taking into consideration the depth required for the liquid chambers and the liquid channel 112.

Specifically, the thickness of the sheet 111b' is preferably in the range of 25~500 μm, and the thickness of the sheet 111c' is preferably in the range of 10~300 μm.

Further, in this embodiment (i.e., the case where the cover plate 113 is pressed), when the thickness of the sheet 111a' is preferably 50 μm or greater, or more preferably in the range of 100~1000 μm, then sheet 111a' sufficiently functions as a support layer for the liquid channel device 110.

The width of the liquid channel 112, and the capacity and shape of the various chambers and the sealing material supply chamber 116 are not particularly restricted and may be optimally designed. For example, the width of the liquid channel 112 is preferably in the range of 25~2,000 μm and more preferably in the range of 500~2,000 μm, and the capacity of the liquid chamber is preferably in the range of 50~50,000 μl and more preferably in the range of 100~1,000 μl.

However, with regard to the waste solution chamber 114d and the like, there is not a particularly optimal capacity; rather these may be freely designed according to the function of the various chambers.

Note that in the case of a liquid channel device which can close to the open mode, the thickness of the 111c forming the inner layer 111c corresponds to the depth of the sealing material supply chamber 116 and the supply channel 118 which are formed.

Next, in the case of a liquid channel device which can open from the closed mode, the second step of forming a stopper 115 to a part of the liquid channel 112 which was formed to the base plate 111 in the first step above, i.e., to the various positions at which the opening sections S11~S17 are provided, is carried out.

In this second step, the stopper 115 is formed using a method in which a stopper forming material for forming the stopper 115 is coated to specific positions on the liquid channel 112 of a continuously supplied base plate 111 using a coating device 124a such as a printer (a screen printer, for example), dispenser, coater (roll coater, knife coater) or the like.

Next, in the second step in the case of a liquid channel device capable of closing from the open mode, a stopper 115 is formed to the part of the liquid channel 112 which was formed to the base plate 111 in the first step above, i.e., to the various positions at which the opening sections S11~S17 are provided, and the sealing material supply chamber 116 which was formed to the base plate 111 in the first step is filled with the sealing material 117.

The formation of the stopper 115 is carried out using a method which employs a coating device 124a such as a printer (screen printing, for example), dispenser, coater (roll coater, knife coater) or the like, to coat a stopper forming material for forming stopper 115 to specific positions on the liquid channel 112 of a continuously supplied base plate 111.

The stopper forming material is not particularly restricted as long as it is a material which is not mutually reactive with the liquid flowing through the liquid channel 112, which can stop the liquid with assurance when in the closed state and which will undergo plastic deformation when subjected to pressing. For example, a resin composition including a resin component, a plastic component, a filler and a solvent, may be used. Further, when employing a dispenser as the coating device 124a, the viscosity of the resin composition is preferably in the range of 30~500 dPa·s. When employing a screen printer or the like, the viscosity of the resin composition is preferably in the range of 50~500 dPa·s.

From the perspective of sealing strength, stability, solubility, coating properties (printability, dispensability, etc.) and the like, it is optimal to employ as the resin component, a resin for which, preferably, the glass transition temperature is −10° C. or less and weight average molecular weight is 300,000 or less. Types of resins which may be cited include ester resins, such as epoxy resin, polyester resin, chloride resins, acrylic resins, and phthalates. One or more of these resins may be used.

A plasticizer for which the glass transition temperature is 30° C. or less is optimally employed as the plastic component. Types of plasticizers which may be cited include thermoplastic resins which a low melting point such as hard resin type resins, epoxy resins, polyester resins and the like. One or more of these plasticizers may be employed.

The filler is added to adjust the viscosity and formability of the stopper forming material. Suitable examples that may be cited include barium sulfate sediment, talc, needle silicon oxide, hollow beads, etc. One or more of the aforementioned may be employed.

A stopper formed from a resin composition which incorporates hollow beads (made of glass, resin, etc.) not only undergoes plastic deformation but also may experience breaking and destruction of the hollow beads. As a result, the volume of the stopper will decrease by the proportion of broken hollow beads. For this reason, a stopper which uses hollow beads undergoes a flatter plastic deformation when subjected to pressing and crushing, so that the liquid can flow more readily when in the open state.

A solvent is incorporated in order to adjust the viscosity of the stopper forming material, and any suitable organic solvent may be employed therefor. Note that as long as printing or other such coating is possible without including a solvent, then it is acceptable, and even desirable, not to include a solvent in the stopper forming material.

By employing a method for coating the stopper formation material using a printing, dispensing or coating method in this way, the stopper 115 can be continuously formed to specific sites with good efficiency.

In the second step, the coating device 124b was used to fill the sealing material supply chamber 116 forming the stopping part T11 with a paste-like sealing material 117. Provided that the method employed is one which coats the sealing material 117 using the aforementioned printing method, dispenser method, or coating method, then it is possible to continuously and efficiently fill a specific site with the sealing material 117.

Any material may be employed for the paste-like sealing material 117 provided that it is one which does not have a reciprocal action with the liquid flowing through the liquid channel 112 and that it is a material which, when pressed down, can seal the liquid channel 112. For example, a resin composition is optimally employed which includes a resin component, a plastic component, and a filler, and which has, for example, a viscosity of 30~500 dPa·s. In addition, the resin composition is preferred that ultimately has a coefficient of extension which is 500% or more.

From the perspective of coating properties (printability, dispensability, etc.), fluidity, sealing ability, stability and the like, it is optimal to employ as the resin component, a resin which preferably has a glass transition temperature of −40° C. or less and a weight average molecular weight of 50,000 or less. Examples of types of such resins include ester resins such as epoxy resins, polyester resins, chlorine containing resins, acrylic resins, phthalate and the like. One or more of these may be used.

A plasticizer having a glass transition temperature of 30° C. or less is optimally employed for the plastic component. Examples of types of plasticizer include thermoplastic resins having a low melting point such as hard resin-type resins, epoxy resins, and polyester resins. One or more plasticizers may be used.

The filler is added to adjust the viscosity of the sealing material 117 and to render the sealing material 117 into a form which readily seals the liquid channel 112 when the sealing material 117 is pressed into the liquid channel 112. Fiber pieces, body pigments, and thixotropy adding agents may be used. Specifically, fumed silica such as AEROSIL (product name, Nippon Aerosil), barium sulfate sediment, or talc can be preferably used.

After coating the stopper forming material and the sealing material 117 to the respective specific sites in this way, various steps not shown in the figures, such as a heat drying step, curing step, etc. are carried out as needed based on the stopper forming material and sealing material 117 compositions.

Next, in the third step, the sheet 113' which forms the cover plate 113 is laminated and adhered to the channel formation surface 112a of the base plate 111. It is desirable in this case to continuously supply the sheet 113' forming the cover plate 113 from the roll 125. Further, while it is desirable to adhere the base plate 111 and the sheet 113' using an adhesive agent supplied from an adhesive agent supplying device, not shown in the figures, it is also acceptable, depending on the materials, to paste together the base plate 111 and the sheet 113' using heat fusion, etc. As a result, it is possible for a plurality of liquid channel devices 110 to produce a continuously linked body.

Figure 20:
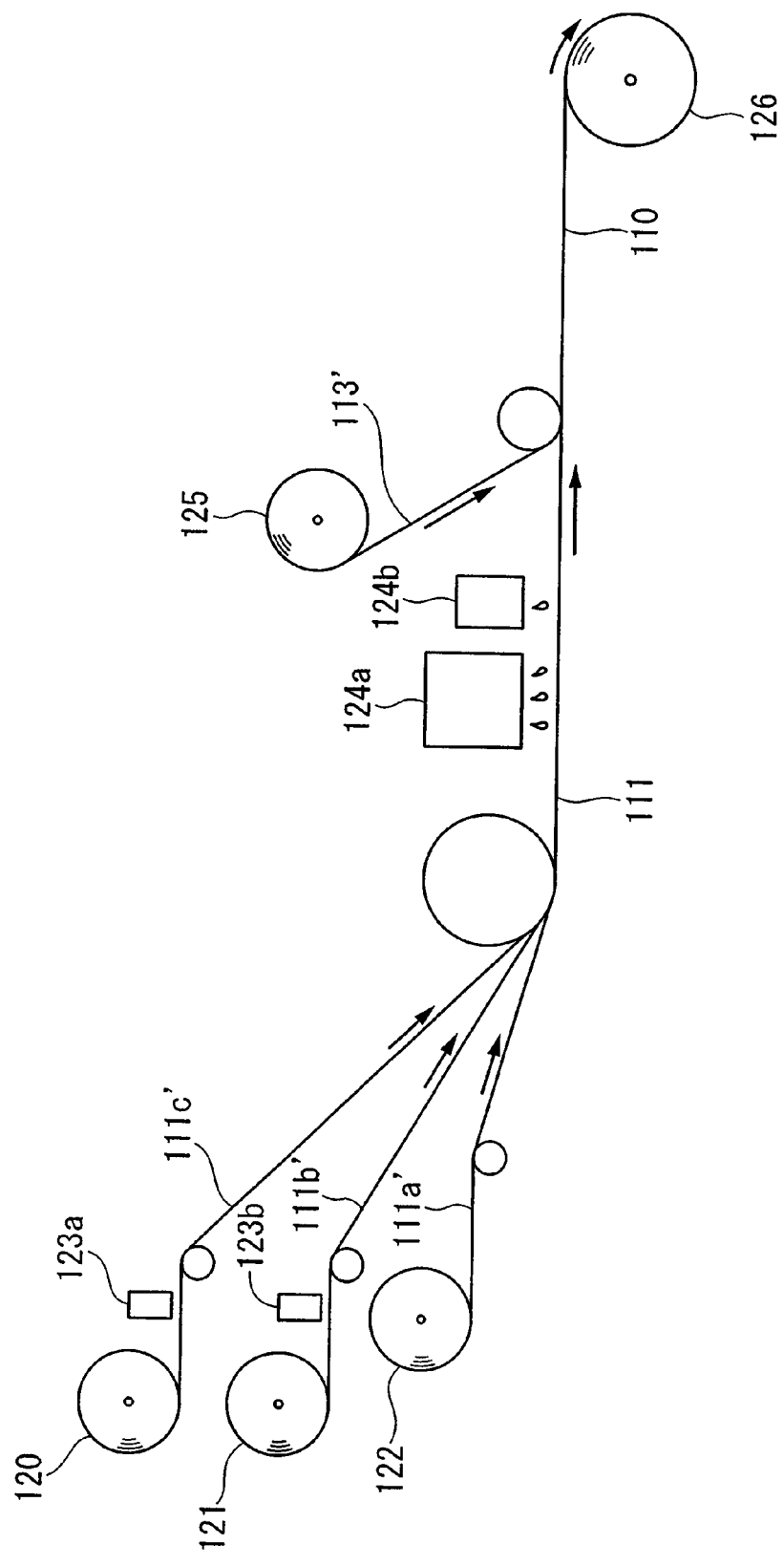
FIG. 20 is a process figure for schematically explaining the production process for the liquid channel device in FIG. 14.

The thus-produced continuous body from the liquid channel device 110 may be wound as shown in FIG. 20 to form a roll 126, or may be folded over. Further, it is also acceptable to render the continuous body into separate sheet-type forms by cutting each. In the case of the roll 126 or the folded forms, it is acceptable to carry out a step in which a perforation or concave-type line is formed in between the various liquid channel devices 110. As a result, folding over the continuous body between the various liquid channel devices 110, or bending the continuous bodies from the liquid channel device 110 becomes easy. In addition, it also becomes easy to cut out separate sheet type forms.

Note that cover plate 113 bends when a pressing load is applied as shown by the arrow A in FIG. 17A, and returns to its original state due to its restorative force when that load is subsequently removed. Provided that cover plate 113 is as described, then the material and thickness thereof are not particularly restricted. Examples of materials which may be cited include resins such as styrene resin, acrylic resin, polycarbonate resin, vinyl chloride resin, PEN resin, polyester resin, epoxy resin, phenol resin, ABS resin, polypropylene resin, fiber-reinforced plastic-type resins or the like. Among these, styrene resin, acrylic resin, polycarbonate resin, vinyl chloride resin, PEN resin, and polyester resin are preferred because they are transparent and enable visual inspection of the condition of the liquid flowing through the liquid channel 112. In the case of a liquid channel device which opens from the closed mode, a thickness in the range of 15~300 µm is preferred as this provides flexibility and restorative force to the cover plate 113.

In the case of a liquid channel device which closes from the open mode, a thickness in the range of 30~500 µm is preferred for the cover plate 113.

In the third step, prior to laminating and adhering the cover plate 113 to the channel formation surface 112a of the base plate 111, it is preferable to first carry out a releasing treatment by coating a releasing agent containing a silicon component or the like to the part 113a of the cover plate 113 that contacts the stopper 115. By applying a releasing agent in this way, it is possible to quickly separate the cover plate 113 and the stopper 115 when removing the load shown by arrow A (FIG. 17B), and easily transition to the open state. It is preferable to carry out an adhesive treatment by coating an adhesive agent to the floor 112b of the liquid channel 112 in the area that is in contact with the stopper 115. By doing so, the stopper 115 adheres with certainty to this area, making it possible to more smoothly separate the stopper 115 from the cover plate 113 side accompanying the above-described releasing treatment.

Note that the above explanation exemplified a design for the stopper 115 forming the opening parts S11~S17 in which the stopper 115 undergoes elastic deformation due to external pressing on the cover plate 113, thereby opening the liquid channel 112 from the closed mode. However, it is also acceptable to provide a design in which the stopper 115 undergoes plastic deformation due to an external pressing on the floor 112b of the liquid channel 112 at the area where the stopper 115 is disposed. In this case, it is necessary to design the middle layer 111b and the outer layer 111a forming the base plate 111 to bend when a pressing load is applied, and to return to their original forms under their restorative force when the load is subsequently removed. In this case (i.e., the case where pressing is applied to the bottom part 112b), it is ideal when the thickness of the sheet 111a' is preferably in the range of 10~300 µm, and more preferably in the range of 15~200 µm.

In addition, in this case, it is preferable to carry out an adhesive treatment to the part 113a of the cover plate 113 that is in contact with the stopper 115, and to carry out a releasing treatment to the part of the floor 112b of the liquid channel 112 that is in contact with the stopper 115.

Similarly, the above explanation exemplified an arrangement in which the liquid channel 112 is sealed by causing a sealing material 117 to extrude out due to external pressing on the cover plate 113 in the area corresponding to the sealing material supply chamber 116, as shown in FIG. 19A and FIG. 19B. However, it is also acceptable to provide an arrangement in which the sealing material 117 is extruded out through external pressing on the floor 116a of the sealing material supply chamber 116. In this case, it is necessary to design the middle layer 111b and the outer layer 111a forming the base plate 111 to bend when a pressing load is applied.

Fifth Embodiment

Figure 21:
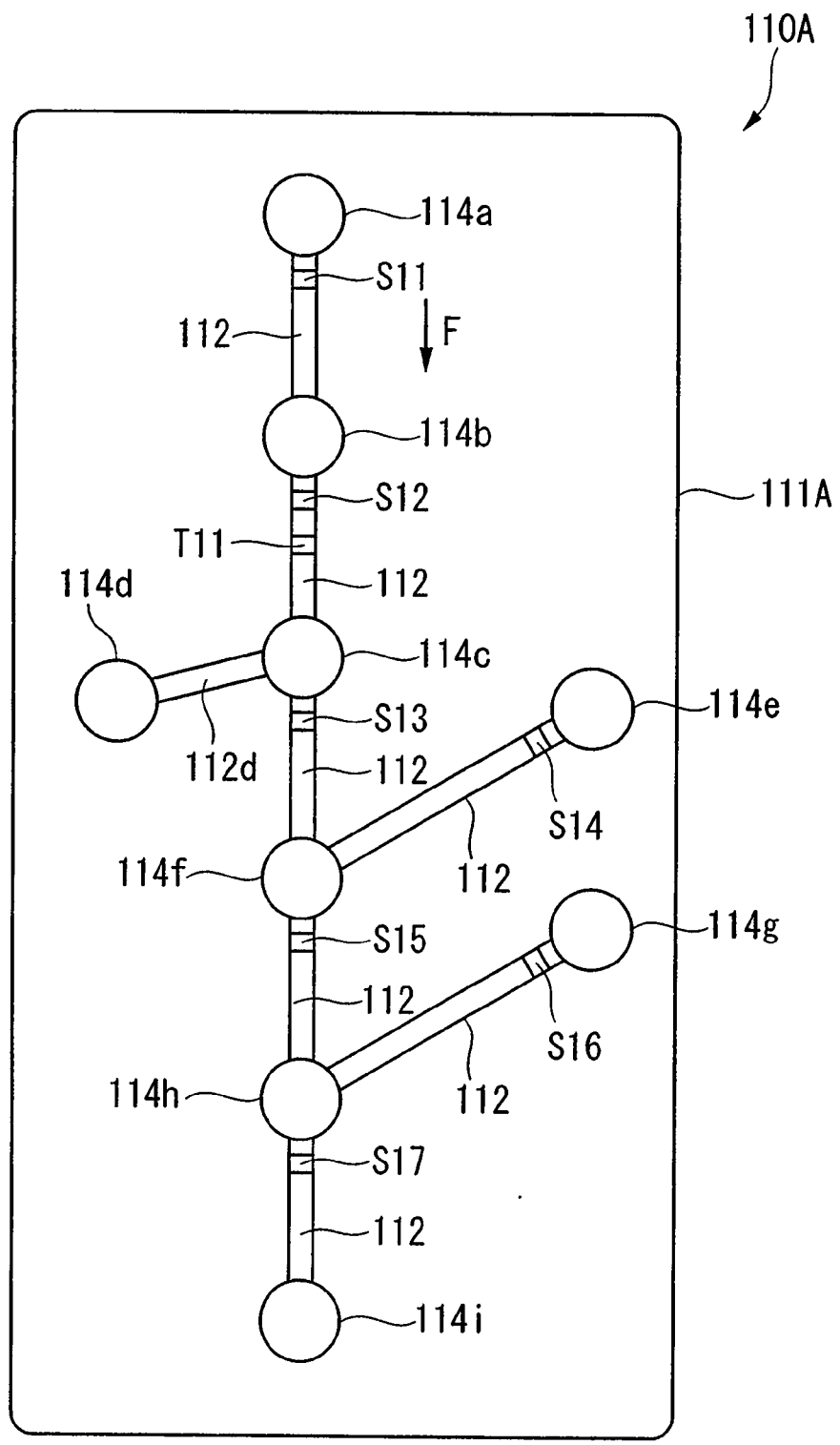
FIG. 21 is a schematic planar perspective view showing the liquid channel device according to the fifth embodiment.
Figure 22:
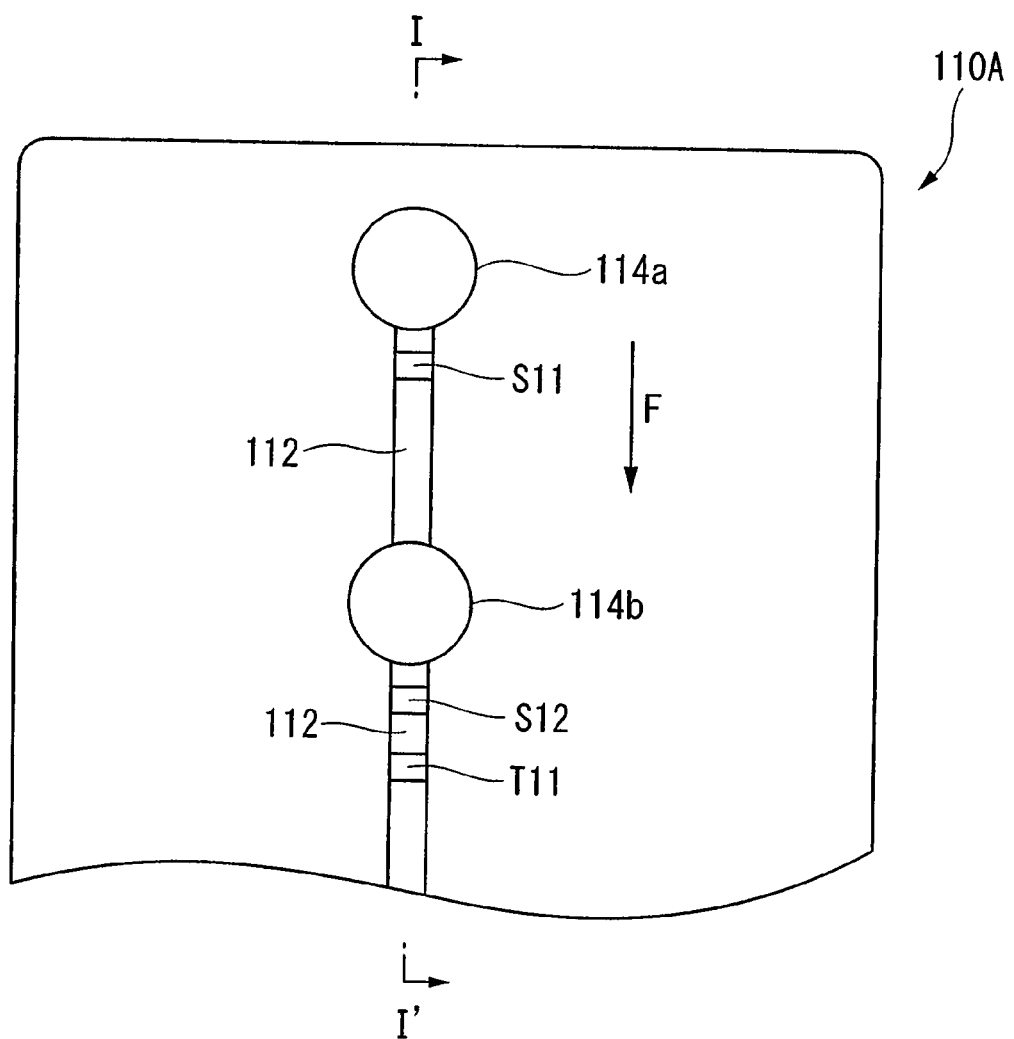
FIG. 22 is a planar perspective view in which a portion of the liquid channel device in FIG. 21 is enlarged.
Figure 23:
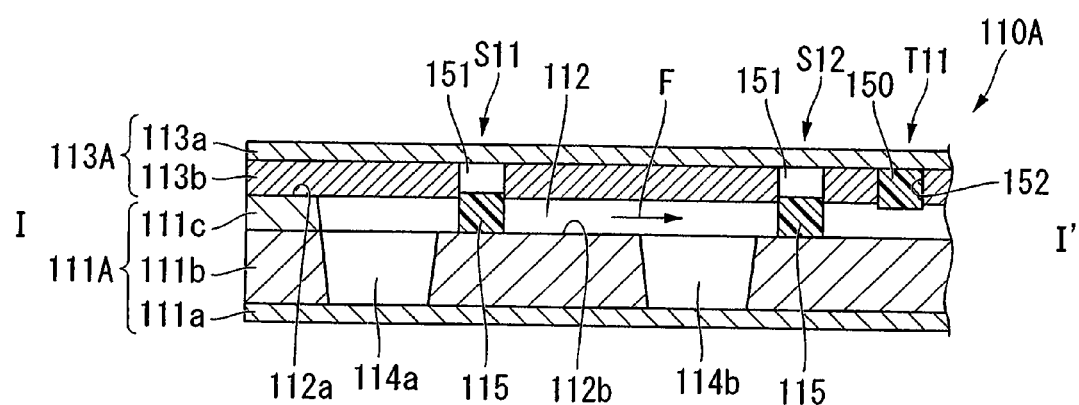
FIG. 23 is a cross-sectional view along the line II-II' in FIG. 22.

FIG. 21 is a planar perspective drawing schematically showing a liquid channel device 110A according to a fifth embodiment. FIG. 22 is a planar perspective drawing in which a portion of the liquid channel device 110A in FIG. 21 has been enlarged. FIG. 23 is a cross-sectional view along the line I-I' in FIG. 22.

A square base plate 111A, formed of a flat plate, and a cover plate 113A, formed to the channel formation surface 112a on the side of the base plate 111A where the liquid channel 112 is formed, are laminated together in this liquid channel device 110A. The remainder of the design is equivalent to that of the fourth embodiment and will therefore be omitted from the discussion.

The base plate 111A of this liquid channel device 110A is made of a plurality of layers as shown in FIG. 23. Specifically, the base plate 111A has a three-layer design comprising an outer layer 111a, a middle layer 111b laminated to the inside of the outer layer 111a, and a inner layer 111c laminated to the inside of the middle layer 111b.

The top part (the portion of the liquid chamber on the cover plate 113A side) of the liquid chambers (only sample introduction chamber 114a and filtering chamber 114b are shown in FIG. 23) and the liquid channel 112 are formed to the inner layer 111c.

The bottom part (the portion other than the aforementioned top part, the portion on the floor side of the liquid chambers) is formed to the middle layer 111b. The surface of the middle layer 111b on its inner layer 111c side forms the floor 112b of the liquid channel 112.

The outer layer 111a is disposed to the outermost side of the base plate 111A, and its surface that is on the middle layer 111b side forms the floor of the liquid chambers.

The cover plate 113A is also made of plural layers. Specifically, the cover plate 113A has a two-layer design comprising the outer layer 113a and the inner layer 113b which is laminated to the inside of the outer layer 113a.

As in the case of the fourth embodiment, this liquid channel device 110A is provided with opening sections S11~S17 for opening a portion of the liquid channel 112 from the closed mode, and the closing part T11 for closing a portion of the liquid channel 112 from the open mode. The design of the opening parts S11~S17 and the closing part T11 are the same as that of the fourth embodiment, therefore an explanation thereof is omitted here.

In this embodiment, the opening sections S11~S17 are equipped with a resin stopper 115 inside the liquid channel 112 which is disposed so as to seal a portion of the liquid channel 112 and stop the flow of liquid, thereby closing that portion of the liquid channel 112, as explained by the example of S11 and S12 in FIG. 23. A concave section 151 capable of housing the stopper 115 is formed to a site opposite the stopper 115 on the inner surface of the cover plate 113A. Specifically, in this embodiment, the concave section 151 is formed by opening a punch-out or the like in the inner surface 113b of the cover plate 113A.

Figure 24A:
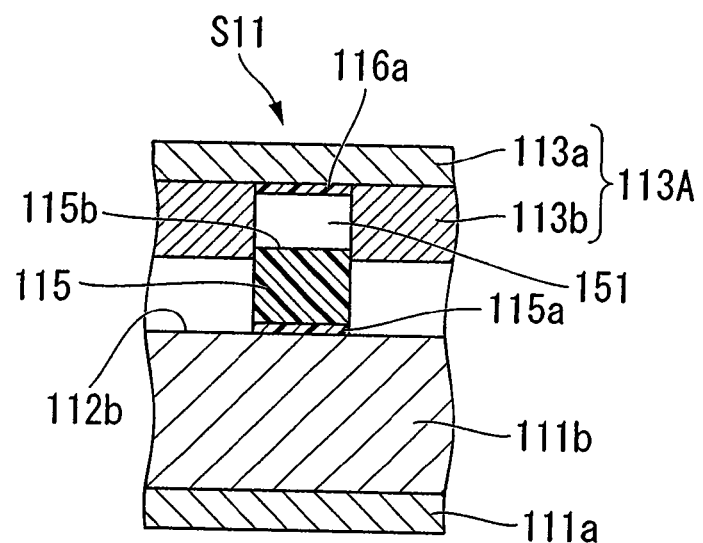
FIG. 24A is an enlarged cross-sectional view of the opening part in FIG. 23.

As shown by the expanded view in FIG. 24A, when in the closed state, the portion (bottom) of the stopper 115 of this embodiment which is in contact with the floor 112b of the liquid channel 112 is fixed in place to the floor 112b of the liquid channel 112 by means of a weakly adhered layer 115a. Further, the height of the stopper 115 is formed to be slightly greater than the height of the liquid channel 112, with the top part 115b side being disposed inside the concave section 151 in a more or less watertight engagement.

A strongly adhered layer 116a, which has a larger adhesive strength than the weakly adhered layer 115a, is formed to a position opposite the top part 115b of the stopper 115 in the concave section 151.

By applying an external pressing force to the floor 112b of the liquid channel 112 or the cover plate 113A in the area where the opening sections S11, S12 are provided (i.e., the area corresponding to the stopper 115 or the concave section 151), the stopper 115 moves from the liquid channel 112 into the concave section 151, thereby opening the liquid channel 112 from the closed mode.

Figure 25A:
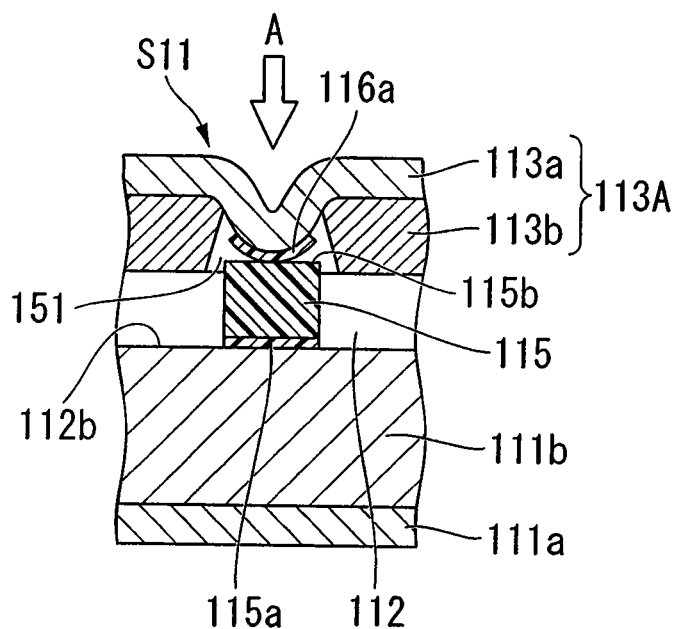
FIG. 25A is a view for explaining the condition when the opening portion operates in the liquid channel device in FIG. 21, and is a cross-sectional view showing the condition when a weight is applied by pressing the cover plate from the outside.
Figure 25B:
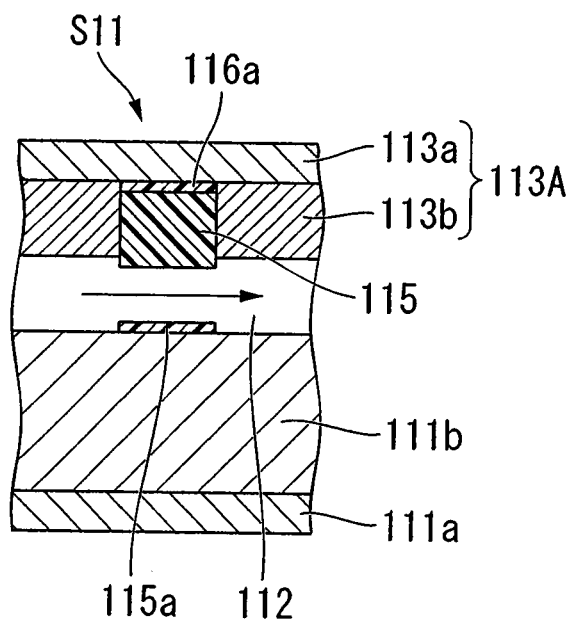
FIG. 25B is a view for explaining the condition when the opening part operates in the liquid channel device in FIG. 21, and is a cross-sectional view showing the state when a weight is removed.

Specifically, as shown by the example of opening section S11 in FIG. 25A and FIG. 25B, the cover plate 113A bends as shown in FIG. 25A when an external pressing load as shown by arrow A is applied to the cover plate 113A. As a result, the strongly adhered layer 116a of the concave section 151 and the top part 115b of the stopper 115 come into contact and become adhered. When the load is subsequently removed, the cover plate 113A returns to its original state due to its restorative force, as shown by FIG. 25B. Accompanying this, the stopper 115 which is adhered in the concave section 151 by the action of the strongly adhered layer 116a separates from the floor 112b of the liquid channel 112, and is thereby housed inside the concave section 151. As a result, the stopper 115 separates from the floor 112b of the liquid channel 112, allowing the liquid to flow.

After a load has been applied by external pressing on the cover plate 113A in the area of provision of the opening sections S11~S17, a pressing operation is employed to the remove the load from these opening sections S11~S17. As a result, the stopper 115 moves from the liquid channel 112 into the concave section 151. As a result, the liquid channel 112 in that area opens from the closed mode.

Note that in FIGS. 25A and 25B, a load is applied to the cover plate 113A by external pressing. However, it is also acceptable to move the stopper 115 from the liquid channel 112 into the concave section 151 by pressing on the floor 112b of the liquid channel 112 in the area of provision of the opening section S11, i.e., by applying an external pressing to the base plate 111A.

In addition, in FIGS. 25A and 25B, the weakly adhered layer 115a remains on the floor 112b side of the liquid channel 112 after the liquid channel 112 has been opened. However, it is also acceptable for the weakly adhered layer 115a to remain in the adhered state on the stopper 115 side.

Figure 24B:
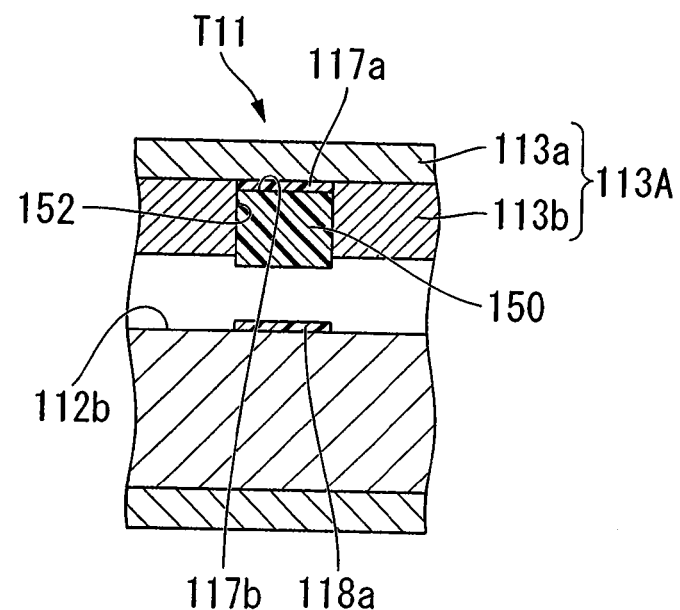
FIG. 24B is an enlarged cross-sectional view of the closing part in FIG. 23.

The closing section T11 of the liquid channel device 110A is provided with a resin stopper 150 as shown in FIG. 24B. This stopper 150 is housed inside the concave section 152 which is formed on the inner surface of the cover plate 113A. Specifically, in this embodiment, the concave section 152 is formed by punching out the inner layer 113b of the cover plate 113A to form a hole. The stopper 150 is housed inside the concave section 152.

In the stopper 150 of this embodiment, when in the open state, the top part 117b adheres in the concave section 152 due to the weakly adhered layer 117a, and is housed therein. The height of the stopper 150 is formed to be slightly greater than the height of the liquid channel 112. When the liquid channel 112 is in the closed state as described below, then the top part 117b side is designed to be engaged in a more or less watertight manner within the concave section 152.

The strongly adhered layer 118a is formed to a position opposite the bottom part of the stopper 150 in the floor 112b of the liquid channel 112.

Further, the stopper 150 moves from within the concave section 152 into the liquid channel 112 by means of external pressing to the cover plate 113A or the floor 112b of liquid channel 112 at the area of provision of the closing section T11 (at the area corresponding to the stopper 150 and the concave section 152), thereby closing the liquid channel 112 from the open mode.

Figure 26A:
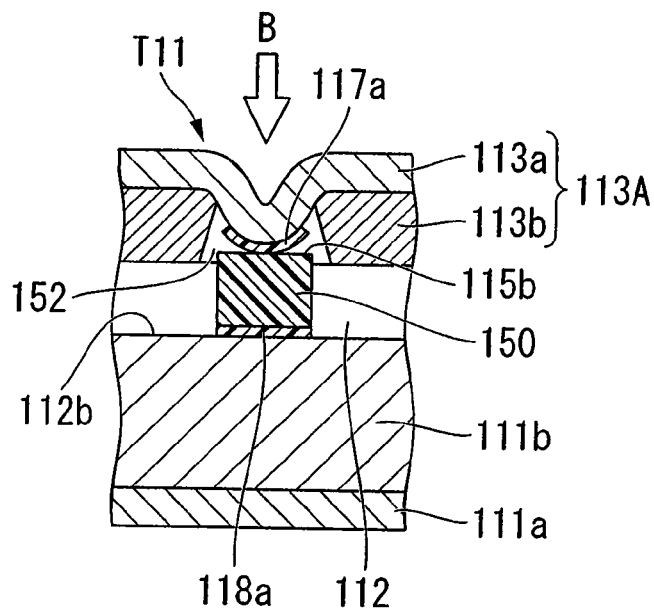
FIG. 26A is a view for explaining the condition when the closing portion operates in the liquid channel device in FIG. 21, and is a cross-sectional view showing the condition when a weight is applied by pressing the cover plate from the outside.
Figure 26B:
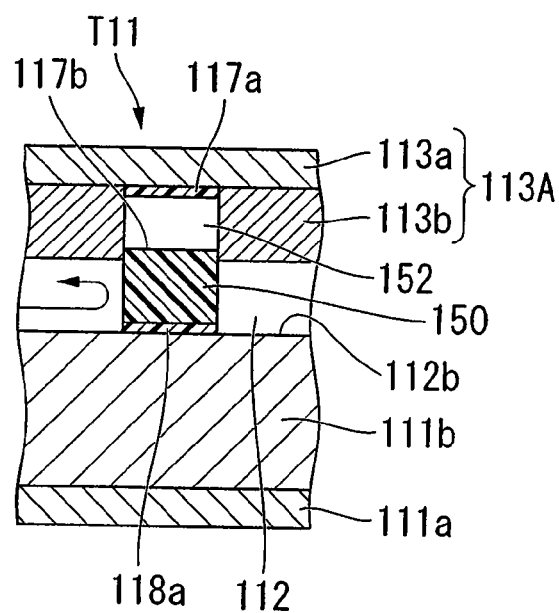
FIG. 26B is a view for explaining the condition when the closing part operates in the liquid channel device in FIG. 21, and is a cross-sectional view showing the state when a weight is removed.

Specifically, as shown in FIGS. 26A and 26B, when a load is applied as shown in the direction of arrow B from the outside onto cover plate 113A, then the cover plate 113A bends as shown in FIG. 26A. As a result, the strongly adhered layer 118a on the floor 112b of the liquid channel 112 and the bottom part of the stopper 150 come into contact and adhere. When the load is subsequently removed, then the cover plate 113A returns to its original state due to its restorative force. In this case, the stopper 150 does not accompany the cover plate 113A, but remains adhered to the floor 112b of the liquid channel 112 due to the action of the strongly adhered layer 118a. Even if the cover plate 113A returns to its original state, the stopper 150 does not accompany it, but rather remains adhered to the liquid channel 112. As a result, the liquid channel 112 is closed by the stopper 150, so that liquid cannot flow through that portion. In this case, as described above, the top part 117b of the stopper 150 enters a state of more or less watertight engagement within the concave section 152.

In a closing section T1 of this kind, once a load has been applied by means of a pressing force from the outside on the cover plate 113 at the area of provision of the closing part T11, the stopper 150 moves from within the concave section 152 to the liquid channel 112 as a result of pressing to remove the load. As a result, the liquid channel 112 closes from the open mode.

Note that in FIGS. 26A and 26B, a load is applied by pressing the cover plate 113A from the outside. However, it is also acceptable to move stopper 150 into the liquid channel 112 in the same manner by external pressing of the floor 112b of the liquid channel 112, i.e., from the outside of the base plate 111A, in the area of provision of the stopping section T11.

Further, in FIGS. 26A and 26B, the weakly adhered layer 117a remains on the concave section 152 side once the liquid channel 112 is closed. However, it is also acceptable for the weakly adhered layer 117a to remain adhered on the stopper 150 side.

In a specific method for formulating a measured liquid employing this type of liquid channel device 110A, the liquid channel device 110A is placed so that the sample introduction chamber 114a is disposed in the upward direction and the measuring chamber 114i is disposed in the downward direction, with the liquid then flowing under gravity from the upstream to the downstream side.

Next, the sample is sampled using a syringe and the cover plate 113A in the area corresponding to the sample introduction chamber 114a is pieced with the syringe needle, to inject the sample into the sample introduction chamber 114a. Next, a pressing operation as described above is applied to the opening section S11 which is provided in between the sample introduction chamber 114a and the filtering chamber 114b, i.e., a load is applied by pressing on the cover plate 113A or on the bottom portion of the liquid channel 112. An operation to remove the load is subsequently carried out, causing the stopper 15 to move within the concave section 151. The liquid channel 112 in this area opens from the closed mode, and the sample is introduced as far as the filter tank 114b under the force of gravity.

In this case, pressing may be performed with the operator's finger, or a pre-programmed pressing device in which the pressing site is defined by X,Y coordinates may be employed to press a specific position.

Next, once filtering is carried out at filtering chamber 114b, then the liquid channel 112 in the area of opening section S12 provided in between the filtering chamber 114b and the metering chamber 114c is opened by similarly moving the stopper 115 within the concave section 151, thereby introducing the sample into the metering chamber 114c under the force of gravity.

Next, once the beginning of overflow of the introduced liquid is confirmed at metering chamber 114c, the stopper 150 is moved from the concave section 152 into the liquid channel 112 at closing section T11 which is provided in between the filtering chamber 114b and the metering chamber 114c, thereby closing the liquid channel 112 in this area.

In this way, the further introduction of liquid from upstream into the metering chamber 114c is prevented, after which the opening section S13 which is provided downstream from the metering chamber 114c is operated to introduce the sample quantified at metering chamber 114c into the first mixing chamber 114f.

The thus-quantified sample is introduced into the first mixing chamber 114f, and the opening section S14 which is in between the first reagent chamber 114e and the first mixing chamber 114f is opened in the same manner. The first reagent is introduced into the first mixing chamber 114f, and the sample and the first reagent are mixed in the first mixing chamber 114f, to formulate an intermediate solution.

Next, the opening section S15 which is in between the first mixing chamber 114f and the second mixing chamber 114h is transitioned to the open state in the same manner. The intermediate solution which was formulated in the first mixing chamber 114f is introduced into the second mixing chamber 114h. The opening section S16 which is in between the second reagent chamber 114g and the second mixing chamber 114h is transitioned to the open state in the same manner, and the second reagent is introduced to the second mixing chamber 114h. The intermediate solution and the second reagent are mixed in the second mixing chamber 114h to formulate a measured liquid.

Next, the opening section S17 which is in between the second mixing chamber 114h and the measuring chamber 114i is transitioned to the open state in the same manner. The measured liquid which was formulated in the second mixing chamber 114h is introduced into the measuring chamber 114i Next, after the measured liquid is introduced into the measuring chamber 114i, the liquid channel device 110A is supplied to the detector and analyzer, and detection and measurement of the desired component is performed.

Note that in the process for formulating the measured liquid in this way, the continuous holes, not shown in the figures, which are provided to the various liquid chambers are suitably opened and closed as necessary. As a result, the liquid flows easily, the accuracy of the liquid volume is improved and control of the flow of the liquid may be carried out.

As in the case of the previously described liquid channel device 110 according to the fourth embodiment, this liquid channel device 110A is provided with the opening sections S11~S17, the closing section T11 which transitions from the open to the closed state, and the opening sections S15, S14, and S16. As a result, this liquid channel device 110A provides the same effects as the liquid channel device 110.

The liquid channel device 110A of this embodiment, i.e., a liquid channel device 110A in which the cover plate 113A is formed of two layers, and the concave section 151,152 are formed to the cover plate 113A, is formed by the flowing method.

In other words, the liquid channel device 110A can be produced by means of a first step in which the liquid channel 112 and the liquid chamber are formed to the base plate 111A, and concavities 151,152 are formed to the cover plate 113A; a second step in which a stopper 115 forming the opening sections S11~S17 are formed to a portion of the liquid channel 112, and a stopper 150 forming the closing sections T11 is formed inside the concave section 152 of the cover plate 113A; and a third step in which the surface of the cover plate 113A on which the concavities 151,152 are formed is laminated to the channel formation surface 112a on the side of the base plate 111A on which the liquid channel 112 and the like are formed.

The method for producing the liquid channel device 110A will now be explained by referencing FIG. 27 that schematically shows the production method for a liquid channel device 110A.

In the first step, a roll 120 of sheet 111c' which forms the inner layer 111c of the base plate 111A, a roll 121 of sheet 111b' which forms the middle layer 111b, and a roll 122 of sheet 111a' which forms the outer layer 111a of the base plate 111A, are prepared in advance.

Next, sheet 111c' is continuously supplied from the roll 120 of the sheet 111c' forming the inner layer 111c and die-cutter 123a is used to punch out linear shapes at sites corresponding to the liquid channel 112 and to punch out areas corresponding to the top part of the metering chamber 114c and other various liquid chambers in the shape of a hole.

Next, sheet 111b' is continuously supplied from the roll 121 of the sheet 111c' forming the middle layer 111b and die-cutter 123b is used to punch out holes at sites corresponding to the bottom portion of the metering chamber 114c and other various liquid chambers.

Next, sheet 111a' is continuously supplied from the roll 122 of the sheet 111a' forming the outer layer 111a and the various sheets 111a', 111b' and 111c' are sequentially laminated to form the base plate 111A.

Here, it is preferable that the various sheets 111a', 111b' and 111c' be adhered using an adhesive agent that is supplied from the adhesive agent supplying device not shown in the figures. However, depending on the material of each of the sheets 111a', 111b', 111c', it is also acceptable to attach the sheets together using heat fusion. It also acceptable to use a sheet coated with a binder or adhesive agent.

In the first step, a roll 125 of sheet 113b' which forms the inner layer 113b of the cover plate 113A, and a roll 126 of sheet 113a' which forms the outer layer 113a of the cover plate 113A are prepared in advance. Next, sheet 113b' is continuously supplied from the roll 125 of the sheet 113b' forming the inner layer 113b and die-cutter 123c is used to punch out sites corresponding to concavities 151,152.

Next, sheet 113a' is continuously supplied from the roll 126 of the sheet 113a' forming the outer layer 113a of the cover plate 113A, and the cover plate 113A is produced by laminating the various sheets 113a',113b'.

Here, it is preferable that the various sheets 113a', 113b' be adhered using an adhesive agent that is supplied from the adhesive agent supplying device not shown in the figures. However, depending on the material of each of the sheets 113a', 113b' it is also acceptable to attach the sheets together using heat fusion. It also acceptable to use a sheet coated with paste or adhesive agent.

As a first step in this way, the various sheets 111a', 111b', 111c', 113a', 113b' are supplied from the various rolls 120, 121, 122, 125, 126, specific forms are punched out from sheets 111b', 111c', 113b', and the various sheets 111a', 111b', and 111c' are subsequently laminated in sequence and adhered. In addition, when employing a process in which the sheets 113a' and 113b' are laminated and adhered, it is possible to continuously produce a plurality of base plates 111A in which the liquid channel 112, liquid chambers and the like are formed, and a plurality of cover plates 113A in which concavities 151,152 are formed.

A method of this type offers low production costs and enables simple and large volume production, and is suitable for industrial applicability, as compared to a method in which photolithography, cutting or the like is employed to form the liquid chambers, liquid channel or concavities to the base plate or the cover plate made of a single plate, or a method in which injection molding or the like is used to form the base plate or the cover plate in which the liquid chambers, liquid channel or concavities are formed.

Note that a method in which the sheets 111b', 111c', 113b' are punched out in a specific shape to form the liquid channel 112, liquid chambers and concavities 151, 152, etc., is excellent with respect to productivity at low cost. However, it is also acceptable to employ other methods (laser, drilling with a knife, heat working, etc.) to form the liquid channel 112, liquid chambers, concavities 151, 152 and the like by opening specific shapes in the sheet 111b', 111c', 113b'.

This embodiment showed a design in which the base plate 111A of the liquid channel device 110A is made of three layers including the outer layer 111a, middle layer 111b, and inner layer 111c. However, it is also acceptable to make the base plate 111A of the liquid channel device 110A of two layers including the outer layer 111a and the inner layer 111c. In this case, the liquid channel 112 and the liquid chambers are formed on top of the sheet 111c' which forms the inner layer 111c. In this case, the depth of the liquid channel 112 and the liquid chambers which are formed is the same.

Examples of resins which may be used for the material of the various sheets 111a', 111b', 111c' forming the outer layer 111a, middle layer 111b, inner layer 111c of the base plate 111A, and the various sheets 113a', 113b' forming the outer layer 113a and inner layer 113b of the base plate 113A include styrene resin, acrylic resin, polycarbonate resin, vinyl chloride resin, PEN resin, polyester resin, epoxy resin, phenol resin, ABS resin, polypropylene resin, fiber-reinforced plastic or the like. Among these, styrene resin, acrylic resin, polycarbonate resin, vinyl chloride resin, PEN resin, and polyester resin are preferred because they are transparent and enable visual inspection of the condition of the liquid flowing through the liquid channel 112.

Note that in this embodiment, a resin roll was employed as the material for the base plate 111A and cover plate 113A, and various resins were cited as examples of the sheet material in order to explain the optimal method for producing the liquid channel device 110A in this case. However, the production method is not limited thereto. For example, in the case where it is necessary to stably support the liquid channel device, it is also possible to use transparent materials such as glass other than resins, and to form the liquid channel, liquid chambers, concavities and the like by suitably employing machining or the like thereto.

The thickness of the various sheets 111a', 111b', 111c' may be suitably designed. In the case of the liquid channel device 110A shown in the figures, the thickness of the sheet 111c' forming the inner layer 111c corresponds to the depth of the liquid channel 112 which is formed. The sum of the thickness of the sheet 111c' forming the inner layer 111c and the thickness of the sheet 111b' forming the middle layer 111b corresponds to the total depth of the channels. Thus, the thickness of the sheet 111b' and the sheet 111c' is decided after taking into consideration the depth obtained from the liquid chambers, liquid channel 112, etc.

Specifically, the thickness of the sheet 111b' is preferably in the range of 25~500 μm, and the thickness of the sheet 111c' is preferably in the range of 10~300 μm.

Further, when operating the opening sections S11~S17 and closing section T11 by pressing on the cover plate 113A, the thickness of the sheet 111a' is preferably 50 μm or more, and more preferably in the range of 100~1000 μm. When the thickness of the sheet 111a' is in this range, the sheet 111a' sufficiently functions as a support layer for the liquid channel device 110A. Conversely, in the case where a pressing force is applied to the base plate 111A, it is required that the base plate 111A bend when a load is applied via pressing and that it have restorative force to return to its original state when the load is subsequently removed. In this case, a thickness in the range of 10~300 μm is preferred.

The width of the liquid channel 112, and the capacity and shape of the various chambers are not particularly restricted and may be suitably set. For example, the width of the liquid channel 112 is preferably in the range of 25~2,000 μm, and more preferably in the range of 500~2,000 μm. The capacity of the liquid chamber is preferably in the range of 50~50,000 μl, and more preferably in the range of 100~1,000 μl.

However, with regard to the waste solution chamber 114d and the like, there is not a particularly optimal capacity; rather these may be freely set according to the function of the various chambers.

The thickness of the various sheets 113a', 113b' may be suitably designed. In the case of the liquid channel device 110A shown in the figures, the thickness of the sheet 113b' forming the inner layer 113b corresponds to the depth of the concavities 151,152 that are formed. Thus, the thickness of the sheet 113b' is decided after taking into consideration the depth obtained from the concavities 151,152. Further, as shown in FIGS. 25A, 25B and FIGS. 26A, 26B, when operating the opening sections S11~S17 and closing section T11 by pressing on the cover plate 113A from the outside, it is required that the sheets 113a', 113b' bend when a load is applied via pressing and that they have restorative force to return to their original state when the load is subsequently removed. Accordingly, it is necessary to take this fact into consideration as well when determining the thickness of these sheets.

In the case where the cover plate 113A is subjected to a pressing force, the thickness of the sheet 113a' is preferably in the range of 10~300 μm, and the thickness of the sheet 113b' is preferably in the range of 25~500 μm. Conversely, in the case where the cover plate 111A is subjected to a pressing force, the thickness of the sheet 113a' is preferably 50 μm or more.

Next, prior to carrying out the second step, in the case of the liquid channel device 110A of this embodiment, an adhesive layer formation step, not shown in the figures, is carried out in which weakly adhered layers 115a, 117a and strongly adhered layers 116a, 118a are formed at specific sites for holding the stopper 115, 150. A method in which a suitable adhesive agent is selected and coated to specific sites is ideal for forming the weakly adhered layers 115a, 117a and the strongly adhered layers 116a, 118a.

The adhesive agent for the strongly adhered layers 116a, 118a and the weakly adhered layers 115a, 117a may be optimally selected from among conventional agents according to the material employed for the base plate 111A, cover plate 113A and stopper 115, 150. In this case, the adhesive force (adhesive strength) of the adhesive agent forming the strongly adhered layers 116a, 118a must be stronger than the adhesive force of the adhesive agent forming the weakly adhered layers 115a, 117a. When the adhesive force of the adhesive agent forming the strongly adhered layers 116a, 118a is less than the adhesive force of the adhesive agent forming the weakly adhered layers 115a,117a, then it may not be possible to move the stoppers 115,150 from the liquid channel 112 into the concave section 151 or from the concave section 152 to the liquid channel 112, or to hold the stoppers 115, 150 in place after moving, even when pressing on the opening sections S11~S17 or the closing section T11. In such cases, it becomes impossible to open or close the liquid channel 112.

It is preferable that the adhesive force of the adhesive agent forming the strongly adhered layers 116a, 118a be 0.1 N/cm or more greater than the adhesive force of the adhesive agent forming the weakly adhered layers 115a, 117a, with a value in the range of 0.1~30 N/cm being more preferred. When the adhesive force of the adhesive agent forming the strongly adhered layers 116a,118a is 0.1 N/cm or more than the adhesive force of the adhesive agent forming the weakly adhered layer 115a, 117a, the opening sections S11~S17 and the closing section T11 can be operated with certainty.

On the other hand, when the difference in the adhesive forces exceeds 30 N/cm, it becomes difficult to form the adhesive layers.

For this reason, it is preferable to set the adhesive force of the strongly adhered layer 116a, 118a to be in the range of 1~30 N/cm, and of the weakly adhered layers 115a, 117a to be in the range of 0.05~5 N/cm.

Examples of adhesive agents employed in the strongly adhered layers 116a, 118a and the weakly adhered layers 115a, 117a which may be cited include acrylics, rubbers, polyurethanes, polyesters, silicon based adhesive agent, and the like. Among these, acrylic adhesive agents or rubber may be used for the strongly adhered layers 116a, 118a. Further, non-woven cloths or polyester fibers may be included as a wick material. Acrylic adhesive agent or silicon-based adhesive agents are preferably employed for the weakly adhered layers 115a, 117a. In order to maintain the difference between the adhesive force of the strongly adhered layers 116a, 118a and the weakly adhered layers 115a, 117a within the above-described suitable range, methods may be cited such as suitably adjusting the glass transition temperature of the resin forming the various adhesive agents, including additives in the adhesive such as tackifiers, curing agents or wick material, and adjusting the amount of these additives.

Note that the term "adhesive force" as employed here is defined as the adhesive strength at 180° peeling from a stainless plate as specified in JIS Z 0237.

Next, in the second step, the stopper 115 is formed to part of the liquid channel 112 which was formed to the base plate 111A in the first step, i.e., the stopper 115 is formed to the various positions where the opening sections S11~S17 are provided. Additionally, from among the concavities 151,152 formed in the cover plate 113A in the first step, the stopper 150 is formed to the concave section 152 corresponding to the closing section T11.

The formation of the stopper 115 is carried out using a method which employs a coating device 124a such as a printer, dispenser, coater (roll coater, knife coater) or the like, to coat a stopper forming material for forming the stopper 115 to specific positions on the continuously supplied base plate 111.

The stopper 150 is also formed by a method in which the stopper forming material is coated and filled in the concavity 152 using the above-mentioned coating device.

A resin composition having a viscosity in the range of 30~600 dPa·s may be optimally employed as the stopper forming material, for example. Further, it is preferable that a resin composition having a viscosity in the above-cited range does not include a solvent.

The type of resin component included in the resin composition is not particularly restricted, as long as it has excellent coating properties (printability, dispensability, etc.), good sealing ability, and stability when employed as the stopper, and has a viscosity in the above range when employed as a stopper forming material.

A suitable plastic component may be included in the resin composition.

A filler may be included in the resin composition for adjusting the viscosity of the stopper forming material. Examples that may be cited include barium sulfate sediment, talc, needle silicon oxide, hollow beads, etc. One or more of the aforementioned may be employed.

A solvent is incorporated in order to adjust the viscosity of the stopper forming material as necessary, and any suitable organic solvent may be employed therefore.

By employing a method for coating the stopper formation material using a printing, dispensing or coating method in this way, the stoppers 115, 150 can be continuously formed to specific sites with good efficiency.

After coating the stopper forming material to the respective specific sites in this way, various steps not shown in the figures, such as a heat drying step, curing step, etc. are carried out as needed based on the composition of the stopper forming material.

Next, in the third step, the surface of the cover plate 113A on which the concavities 151,152 are formed is laminated and adhered to the channel formation surface 112a of the base plate 111A. Further, while it is desirable to adhere the base plate 111A and the sheet 113A using an adhesive agent supplied from an adhesive agent supplying device, not shown in the figures, it is also acceptable, depending on the materials, to attach the base plate 111A and the sheet 113A using heat fusion, etc. Further, a sheet coated in advance with a binder or adhesive agent may be employed.

As a result, it is possible for a plurality of liquid channel devices 110 to produce a continuously linked body.

The thus-produced continuous body from the liquid channel device 110A may be wound as shown in FIG. 27 to form a roll 127, or may be folded over. Further, it is also acceptable to render the continuous body into separate sheet-type forms by cutting each. In the case of the roll 127 or the folded forms, it is acceptable to carry out a step in which a perforation or concave-type line is formed in between the various liquid channel devices 110A. As a result, folding over the continuous body between the various liquid channel devices 110A, or bending the continuous bodies from the liquid channel device 110A become easy. In addition, it also becomes easy to cut out separate sheet-type forms.

Note that the above-described fifth embodiment provides a design in which the stoppers 115,150 are held at specific sites in advance by the weakly adhered layers 115a, 117a at each of the various opening sections S11~S17 and the closing section T11, and thereafter are moved as a result of pressing from the liquid channel 112 to within concave section 151, or from the concave section 152 into the liquid channel 112, and are held at specific sites by the strongly adhered layers 116a, 118a.

However, the present invention is not limited to an embodiment which employs a method utilizing the difference in adhesive strengths to hold the stoppers 115,150 after moving them to specific positions.

For example, if it is possible to maintain the stoppers 115, 150 tightly within the convex sections 151,152 by elastic force, etc., when in the open mode by adjusting the shape and material of the stoppers 115,150, the shape of the convex sections 151,152, and the material of the lid plate 113A in which the convex sections 151,152 are formed, then it is not absolutely necessary to provide the weakly adhered layer 117a or the strongly adhered layer 116a within the convex sections 151, 152.

Figure 28:
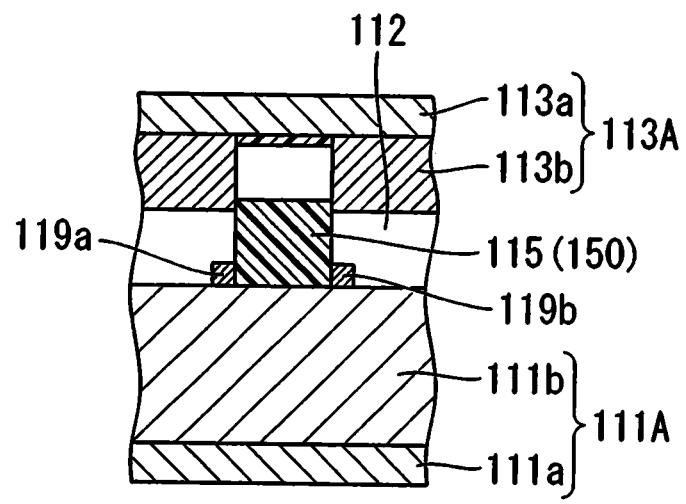
FIG. 28 is a cross-sectional view showing an arrangement in which stopper rests are provided in the liquid channel device in FIG. 21.

Further, it is acceptable to form a pair of stopper rests 119a,119b by creating a projection rising from the floor 112b of the liquid channel 112 as shown in FIG. 28 for example, these stopper rests 119a,119b serving to maintain the stoppers 115,150 at specific sites in the liquid channel 112 with certainty, so that the stoppers 115,150 do not move from this location. When the stopper rests 119a, 119b are formed from an elastic member, then it is possible use the elastic force to hold the stoppers 115,150 so that they do not deviate from the specific sites in liquid channel 112.

Figure 29:
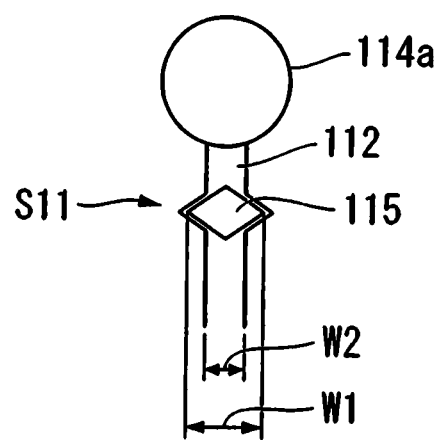
FIG. 29 is a planar view schematically showing an example in which the shape of the stopper in planar perspective is rhombohedral in shape.

In addition, as explained by the example of opening section S11 in FIG. 29, it is also acceptable to employ a method in which the shape of the stopper 115 when viewed in the planar direction is made to be rhombohedral or the like, with the maximum width W1 thereof set to be greater than the width W2 of the liquid channel 112, and an engaging concavity for engaging the ends in the width direction of the stopper 115 is formed in the lateral walls of the liquid channel 112. Employing this method, the ends in the width direction of the stoppers 115,150 engage in the engaging concavity and do not deviate from the specific sites by moving along the liquid channel 112 (i.e., in the vertical direction in the figure). Note that FIG. 29 shows an example of a stopper 115 that is rhombohedral in shape when viewed in the planar direction. However, the shape of the stopper when viewed in the planar direction is not limited to a rhomboid, provided that the stopper 115 is formed to have a maximum width W that is larger than the width W2 of the liquid channel 112, and engaging concavities capable of engaging the stopper 115 are formed in both walls of the liquid channel.

In addition to providing the weakly adhered layers 115a, 117a and the strongly adhered layers 116a,118a, it is acceptable to incorporate the provision of stopper rests 119a,119b, form the stoppers 115,150 to have a rhombohedral shape in planar view, etc., as a means for holding the stoppers 115,150.

Sixth Embodiment

The liquid channel device 110A according to the fifth embodiment described above exemplified a cover plate 113A having a two-layer design comprising an outer layer 113a and an inner layer 113b, and a base plate 111A having a three-layer design comprising an outer layer 111a, middle layer 111b, and inner layer 111c, with concave sections 151,152 formed in the cover plate 113A.

In the sixth embodiment which follows, as shown in FIGS. 30~33, the cover plate 113 is made of one layer, while the base plate 111B has a four-layer design including an outer layer 141a, outside middle layer 141b, inside middle layer 141c, and inner layer 141d. Further, in this embodiment, the concave sections 151, 152 are formed to the floor 112b of the liquid channel rather than to the cover plate 113.

Figure 30:
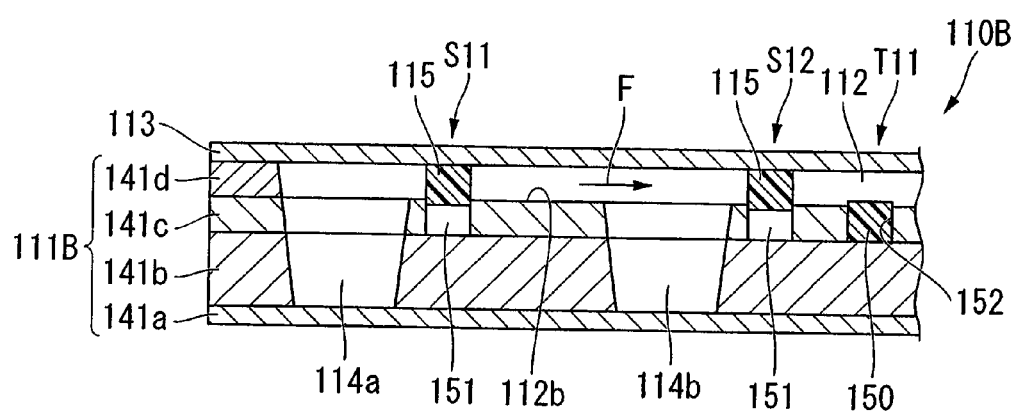
FIG. 30 is a cross-sectional view showing a portion of the liquid channel device according to the sixth embodiment.

As shown in FIG. 30, in the liquid channel device 110B of this embodiment, the base plate 111B has a four-layer structure comprising an outer layer 141a, an outside middle layer 141b which is laminated to the inside of the outer layer 141a, an inside middle layer 141c which is laminated to the inside of the outside middle layer 141b, and an inner layer 141d which is laminated to the inside of the inside middle layer 141c.

The top part (i.e., the portion of the liquid chamber on the cover plate 113 side) of the liquid chambers (only sample introduction chamber 114a and filtering chamber 114b are shown in FIG. 30) and the liquid channel 112 are formed to the inside layer 141d.

The middle part (i.e., the portion other than the aforementioned top part and excluding the portion of the chamber on the floor side) of the liquid chambers and the concave sections 151, 152 are formed to the inside middle layer 141c. The surface of the inside middle layer 141c which is on the inner layer 141d side forms the floor 112b of the liquid channel 112.

The bottom part (i.e., the portion of the floor side of the liquid chamber, excluding the aforementioned top and middle parts) of the liquid chambers are formed to the outside middle layer 141b. The surface of the outside middle layer 141b which is on the inside middle layer 141c side forms the floor of the concave sections 151, 152.

The outer layer 141a is disposed to the outermost side of the base plate 111B, and the surface of the outer layer 141a on the outside middle layer 141b side forms the floor of the liquid chambers.

The cover plate 113 is formed of only one layer.

As exemplified by S11 and S12 in FIG. 30, the opening sections S11~S17 in this liquid channel device 110B are provided with a resin stopper 115 inside the liquid channel 112, the stopper 115 being designed to stop the flow of liquid when disposed so as to cover a portion of the liquid channel 112, thereby closing this portion of the liquid channel. A concave section 151 capable of housing the stopper 115 is formed to a position opposite the stopper 115 on the floor 112b of the liquid channel 112.

Figure 31A:
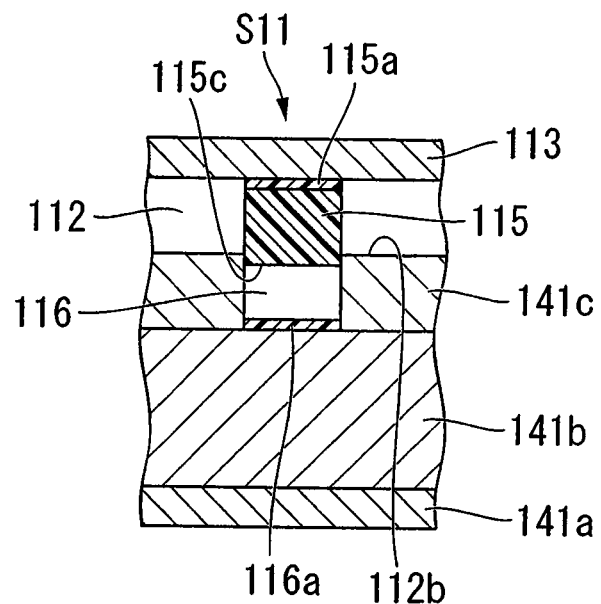
FIG. 31A is an enlarged cross-sectional view of the open part in FIG. 30.

As shown in the enlarged view in FIG. 31A, when in the closed mode, the portion (top part) of the stopper 115 of this embodiment which is in contact with the cover plate 113 is fixed in place to the inner surface of the cover plate 113 by the weakly adhered layer 115a. The height of the stopper 115 is formed to be slightly greater than the height of the liquid channel, with the floor 115c side disposed so as to engage inside the concave section 151 in a more or less watertight fashion.

By external pressing on the floor 112b of the liquid channel 112 or the cover plate 113A in the area where the opening sections S11, S12 are provided, the stopper 115 moves from the liquid channel 112 into the concave section 151, thereby opening the liquid channel 112 from closed mode.

Figure 32A:
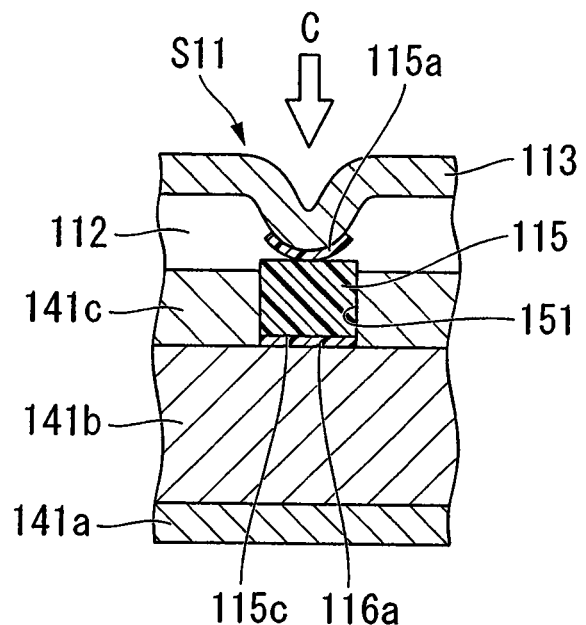
FIG. 32A is a view for explaining the condition when the opening portion operates in the liquid channel device in FIG. 30, and is a cross-sectional view showing the condition when a weight is applied by pressing the cover plate from the outside.
Figure 32B:
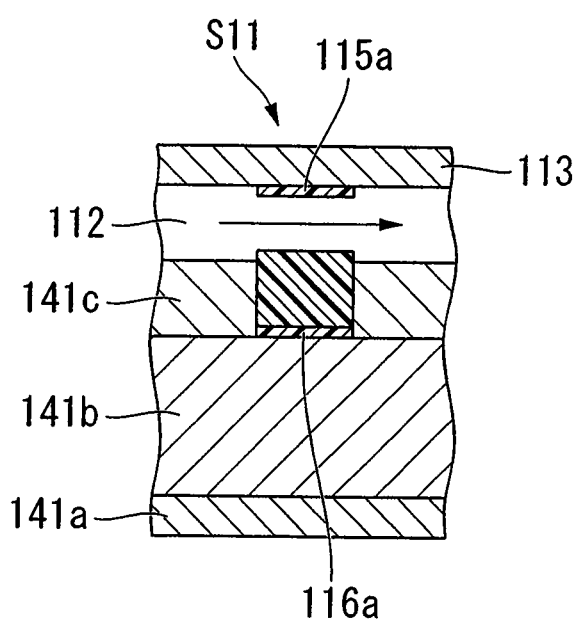
FIG. 32B is a view for explaining the condition when the opening part operates in the liquid channel device in FIG. 30, and is a cross-sectional view showing the state when a weight is removed.

Specifically, as shown by the example of opening section S1 in FIG. 32A and FIG. 32B, when an external load is applied to the cover plate 113 by pressing as shown by arrow C, the cover plate 113 bends as shown by FIG. 32A. The strongly adhered layer 116a of the concave section 151 and the floor 115c of the stopper 115 contact and adhere. When the load is subsequently removed, then, as shown in FIG. 32B, the cover plate 113 returns to its original state due to its restorative force. In this case, the stopper 115 is maintained in the housed state within the concave section 151 due to the action of the strongly adhered layer 116a. As a result, the stopper 115 moves away from the cover plate 113 accompanying the restoration of the cover plate 113, enabling flow of the liquid.

In this type of opening sections S11~S17, an external load is applied by pressing on the cover plate 113 in the area of provision of the opening sections S11~S17. When the load is then removed by means of a subsequent pressing operation, the stopper 115 moves from the liquid channel 112 into the concave section 151, thereby opening that portion of the liquid channel from the closed mode.

Note that in FIG. 32A and FIG. 32B, a load was applied to the cover plate 113 by external pressing, however, it is also possible to move the stopper 115 from the liquid channel 112 into the concave section 151 by external pressing on the floor 112b of the liquid channel 112 in the area of provision of the opening section S11, i.e., by external pressing on the base plate 111B.

Figure 31B:
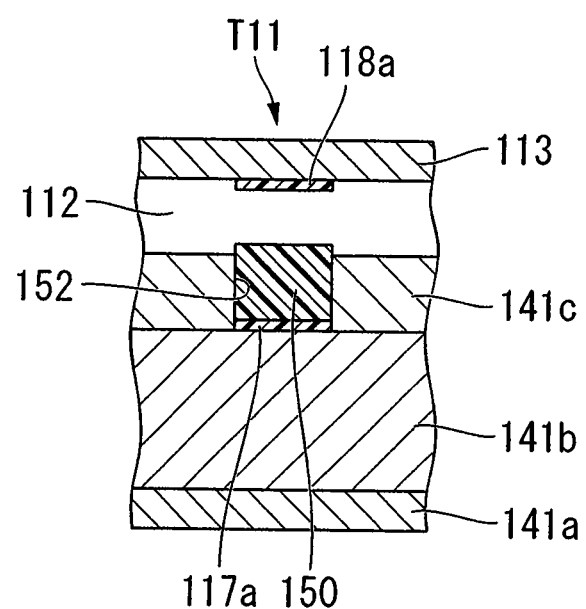
FIG. 31B is an enlarged cross-sectional view of the closed part in FIG. 30.

The closing section T11 of this liquid channel device 110B is provided with a resin stopper 150 as shown in FIG. 31B. This stopper 150 is housed within the concave section 152 which is formed to the floor 112b of the liquid channel 112. Specifically, the concave section 152 is formed by knocking out an opening in the inside middle layer 141c of the base plate 111B, and the stopper 150 is housed therein.

When in the open state, the floor of the stopper 150 of this embodiment adheres to the concave section 152 due to the weakly adhered layer 117a and is housed within the concave section 152. The height of the stopper 150 is formed to be slightly greater than the height of the liquid channel 112. When closing the liquid channel 112 as explained below, the floor side of the stopper 150 engages in a more or less watertight manner inside the concave section 152.

The strongly adhered layer 118a is formed on the inner surface of the cover plate 113, at a position that is opposite the top part of the stopper 150.

The stopper 150 moves from within the concave section 152 into the liquid channel 112 due to external pressing on the floor 112b of the liquid channel 112 or the cover plate 113 in the area of provision of the closing section T11, thereby closing the liquid channel 112 from the open mode.

Figure 33A:
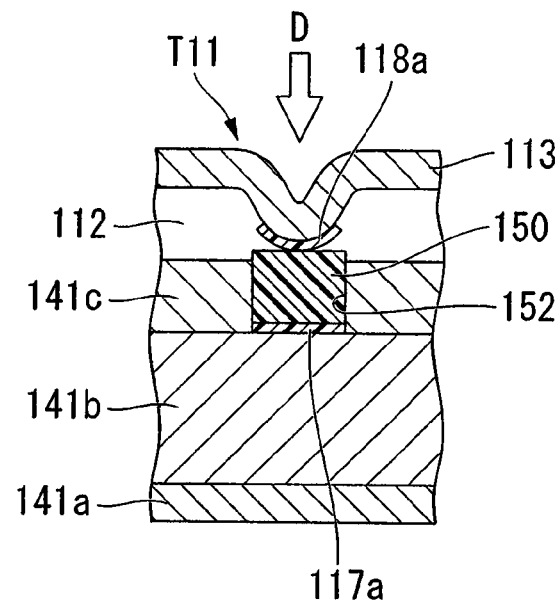
FIG. 33A is a view for explaining the condition when the closing portion operates in the liquid channel device in FIG. 30, and is a cross-sectional view showing the condition when a weight is applied by pressing the cover plate from the outside.
Figure 33B:
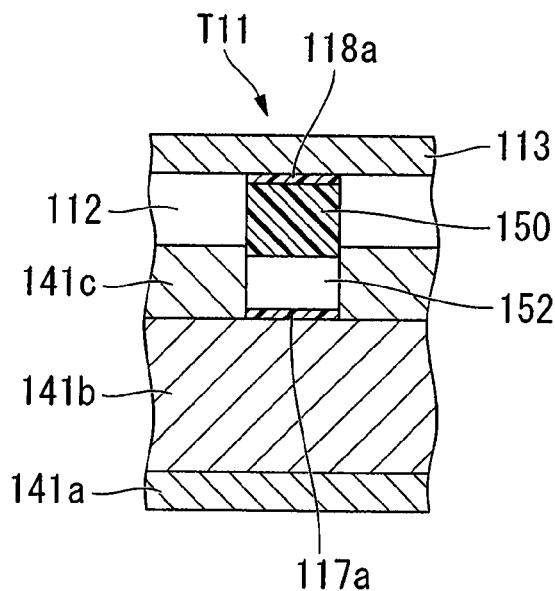
FIG. 33B is a view for explaining the condition when the closing part operates in the liquid channel device in FIG. 30, and is a cross-sectional view showing the state when a weight is removed.

Specifically, as shown in FIG. 33A and FIG. 33B, when an external load is applied to the cover plate 113 by pressing as shown by arrow D, the cover plate 113 bends as shown by FIG. 33A. The strongly adhered layer 118a of the cover plate 113 and the top part of the stopper 150 contact and adhere. When the load is subsequently removed, then, as shown in FIG. 33B, the cover plate 113 returns to its original state due to its restorative force. In this case, the stopper 150 is maintained in the housed state within the cover plate 113 due to the action of the strongly adhered layer 118a. As a result, the stopper 150 moves from the concave section 152 into the liquid channel 112. The liquid channel 112 is thus closed by the stopper 150, so that liquid can no longer flow through this area.

In this type of closing section T11, an external load is applied by pressing on the cover plate 113 in the area of provision of the closing section T11. When the load is then removed by means of a subsequent pressing operation, the stopper 150 moves from the concave section 152 into the liquid channel, thereby closing that portion of the liquid channel 112 from the open mode.

Note that in FIG. 33A and FIG. 33B, a load was applied to the cover plate 113 by external pressing, however, it is also possible to move the stopper 150 from the liquid channel 112 by external pressing on the floor 112b of the liquid channel 112 in the area of provision of the closing section T11, i.e., by external pressing on the base plate 111B.

This liquid channel device 110B of this embodiment can be produced by a method provided with a first step of forming the liquid channel 112, the liquid chambers, and the concave sections 151, 152 to the base plate 111B; a second step of forming the stopper 115 which forms the opening sections S11~S17 to the inner surface of the cover plate 113 in the area of provision of the opening sections S11~S17, and forming the stopper 150 which forms the closing section T11 to the inside of the concave section 152 corresponding to the closing section T11; and a third step of laminating the surface of the cover plate 113 where the stopper 115 is formed to the channel formation surface 112a which is on the side of base plate 111 where the liquid channel 112, etc. is formed.

In the first step, as shown in FIG. 34, a roll 128 of sheet 141d' which forms the inner layer 141d of the base plate 111B, a roll 129 of sheet 141c' which forms the inside middle layer 141c, a roll 130 of sheet 141b' which forms the outside middle layer 141b, and a roll 131 of sheet 141a' which forms the outer layer 141a, are prepared.

Next, the sheet 141d' is continuously supplied from roll 128 of sheet 141d' forming the inner layer 141d, and a die-cutter 123a is used to punch out a linear form at the site corresponding to the liquid channel 112, and punch out a hole at the area corresponding to the top part of metering chamber 114c and the other various liquid chambers.

Next, the sheet 141c' is continuously supplied from roll the 129 of the sheet 141c' forming the inside middle layer 141c, and a die-cutter 123b is employed to punch out holes at the sites corresponding to the middle part of the metering chamber 114c and the other various liquid chambers, and to punch out area corresponding to the concave sections 151, 152.

Next, the sheet 141b' is continuously supplied from roll 130 of sheet 141b' forming the outside middle layer 141b. Next, a die-cutter 123c is employed to punch out holes at the sites corresponding to the bottom part of the metering chamber 114c and the other various liquid chambers.

Next, the sheet 141a' is continuously supplied from roll 131 of sheet 141a' forming the outer layer 141a, and the various sheets 141a', 141b', 141c', 141d' area sequentially laminated, to produce the base plate 111B.

Here, it is preferable that the various sheets 141a', 141b', 141c' and 141d' be adhered together by means of an adhesive supplied from an adhesive supplying device not shown in the figures. However, depending on the material of the various sheets 141a', 141b', 141c' and 141d', it is also acceptable to attach the sheets together using heat fusion or the like. In addition, it is also acceptable to employ a sheet coated in advance with an adhesive or the like.

Next, prior to carrying out the second step, as in the case of the fifth embodiment, an adhesive layer formation step, not shown in the figures, is carried out in which the weakly adhered layers 115a, 117a and the strongly adhered layers 116a, 118a for holding the stopper 115 and 150, are formed at specific sites for holding the stoppers 115, 150.

Next, in the second step, the sheet 113' is continuously supplied from the roll 132 of the sheet 113' for forming the cover plate 113, and the stopper 115 is formed to the inner surface of the cover plate 113 so as to correspond to the position of the opening sections S11~S17. From among the concave sections 151, 152 which are formed to the floor 112b of the liquid channel 112 in the first step, the stopper 150 is formed to the inside of the concave section 152 forming the closing section T11.

As explained in the fifth embodiment, the formation of the stopper 115 is optimally carried out using a method in which a stopper forming material for forming the stopper 115 is coated using a coating device 124a such as a printer, dispenser, coater (roll coater, knife coater) or the like. The formation of the stopper 150 is ideally carried out using a method in which the coating device 124a is used to coat the stopper forming material to the inside of the concave section 152 which is formed to a continuously supplied base plate 111B.

The materials exemplified in the fifth embodiment are ideally employed as the stopper forming material here.

Next, in the third step, the inner surface of the cover plate 113, i.e., the surface on which the stopper 115 is formed is laminated and adhered to the channel formation surface 112a of the base plate 111B. Here, it is preferable that the base plate 111B and the cover plate 113 be adhered together by means of an adhesive supplied from an adhesive supplying device not shown in the figures. However, depending on the material of the base plate 111B and the cover plate 113, it is also acceptable to attach these together using heat fusion or the like. In addition, it is also acceptable to employ a sheet coated in advance with an adhesive or the like. As a result, it is possible to produce a continuous body in which a plurality of liquid channel devices 110B are continuously linked.

The thus-produced continuous body from the liquid channel device 110B may be wound in the same manner as in the fifth embodiment to form a roll 133, or may be folded over. Further, it is also acceptable to render the continuous body into separate sheet-type forms by cutting each. It is acceptable to carry out a step in which a perforation or concave-type line is formed in between the various liquid channel devices 110B.

As in the case of the fifth embodiment, in this embodiment, if it is possible to maintain the stoppers 115,150 tightly within the convex sections 151,152 due to elastic force, etc., when in open mode by adjusting the shape and material of the stoppers 115,150, the shape of the convex sections 151,152, and the material of the base plate 111B in which the convex sections 151,152 are formed, then it is not absolutely necessary to provide the weakly adhered layer 117a or the strongly adhered layer 116a within the convex sections 151, 152.

As in the case of the fifth embodiment, a pair of stopper rests 119a, 119b may be formed for holding the stoppers 115,150.

Further, it is acceptable for the ends of the stoppers 115,150 in the width direction to engage in engaging concavities when in the closed mode, so that the stoppers 115,150 do not deviate from the specific sites along the liquid channel 112 (i.e., deviate in the vertical direction in the figure).

It is also acceptable to employ these means in combination.

In the liquid channel devices 110, 110A, 110B exemplified in the fourth through sixth embodiments above, the liquid channel 112 was formed to only one surface of the base plate 111A, 111B. However, it is also acceptable to form the liquid channel 112 to both surfaces of the base plate 111A, 111B.

Further, there are no limitations on the form of the opening/closing communicating holes which are provided as needed to the various liquid chambers. For example, an embodiment is acceptable in which the communicating holes can be opened or closed by detachment or attachment of a cap capable of engaging with the communicating hole formed in the cover lid 113, 113A. Moreover, opening and closing sections of an equivalent design as the opening sections S11~S17 and the closing section T11 which are provided to the liquid channel 112 may be provided to the communicating holes.

A liquid transport section may be provided as necessary to the various liquid chambers. As a specific design for the liquid transport section, an arrangement may be cited in which external pressing is applied to the floor of the liquid chamber or to the cover plate 113 in the area corresponding to the liquid chamber, causing the internal capacity of the liquid chamber to decrease and expelling the liquid inside the liquid chamber, thereby transporting the liquid downstream. A reverse flow check such as a dam or the like is ideally provided to the liquid chamber which is provided with this type of liquid transport section, for checking the reverse flow of the liquid upstream.

The preceding example disclosed an embodiment in which the action of gravity was employed to move the liquid. However, it is also acceptable to employ centrifugal force. For example, the liquid channel devices 110, 110A, 110B may be set in a centrifuge so that the sample introduction chamber 114a side thereof is positioned on the side of the rotational center, and the measuring chamber 114i side thereof is positioned on the external periphery of the rotation. The liquid channel devices 110, 110A, 110B are then rotated so that the centrifugal force acts from upstream to downstream, with the liquid flowing as a result.

In addition, when rotating the liquid channel devices 110, 110A, 110B and utilizing centrifugal force to cause the liquid to flow in this way, a pressure disk may be employed for the various pressing operations to activate the opening sections S11~S17 and closing section T11. This pressure disk applies pressure at specific sites while moving in the radial direction of rotation over the surface of the cover plates 113,113A of the liquid channel devices 110, 110A, 110B, from the center of rotation to the outer periphery of rotation.

In addition to moving the liquid using gravity or centrifugal force, it is also acceptable to move and cause the liquid to flow by incorporating a method in which the liquid channel 112, a portion of the liquid chambers, or both are heated to expand the air in the liquid channel 112 or liquid chambers, or a method in which an oxygen absorbing agent (readily oxidizable iron powder for example) is sealed into part of the liquid channel 112 to absorb the oxygen and decrease the pressure inside the liquid channel 112.

In the preceding discussion, the method of piercing the cover plate 113,113A with a syringe was exemplified as a method for injecting a sample into the sample introduction chamber 114a. However, it is also acceptable to form a sample injection hole in the cover plates 113,113A in advance and inject the samples via these holes. In this case, a protective tape may be used to cover the sample injection hole, with the injection carried out by piercing the protective tape with the syringe. Alternatively, it is also acceptable to peel off the protective tape and then carry out the injection by introducing the syringe into the sample injection hole.

The sample and reagent that flow through the liquid channel devices 110, 110A, 110B are not particularly restricted. Samples and reagents which are conventionally employed in the medical and environmental fields as well as others, may be suitably combined in use.

For example, in the medical field, such biological derivatives as blood (whole blood), serum, plasma, buffy coat, urine, stercus, saliva, sputum or the like, as well as viruses, or bacterial, mold, yeast, or plant cells, may be cited. It is also acceptable to employ DNA or RNA isolated from these products. Alternatively, it is also acceptable to employ as a sample the products obtained by performing any kind of pre-treatment or dilution on the preceding.

The liquid channel devices 110, 110A, 110B are provided with a filtering chamber 114b downstream from the sample introduction chamber 114a, for filtering the sample which flows from the sample introduction chamber 114a. Thus, by employing a liquid channel device 110, 110A, 110B of this sort, a sample which previously would have required filtering in a separate filtering device can be supplied into the sample introduction chamber 114a of the liquid channel device 110, 110A, 110B without filtering.

The reagent is not particularly restricted, and may be suitably selected in response to the target components. In the case where capturing and analyzing for the presence of an antigen in the sample using the antibody-antigen reaction, it is preferable to use a reagent which includes an antibody to the antigen.

Note that the preceding example disclosed an embodiment in which the antigen was captured by the antibody by prefilling the first reagent chamber 114e and the second reagent chamber 114g with a reagent containing an antibody, and then mixing these reagents with the sample containing the antigen in the first mixing chamber 114f and second mixing chamber 114h. However, the arrangement for capturing the antigen with the antibody is not limited to this embodiment. For example, magnetic beads carrying the antibody or antigen may be fixed in the liquid chambers or along the liquid channel of the liquid channel device 110, 110A, 110B, and the sample may be made to flow through this area, so that the antigens in the same are captured on the antibodies. Next, a suitable reagent may be introduced into the sample introduction chamber 114a via syringe, with the liquid transport section employed as needed, and the thus-captured antigens then washed, denatured, multiplied (concentrated), and separated to increase the accuracy of analysis.

The reactions carried out in the liquid channel devices 110, 110A, 110B are not limited to antibody-antigen reactions. Rather, a variety of chemical reactions, DNA amplifying PCR (polymerase chain reaction), and DNA and other protein capturing reactions can be carried out. It is also acceptable to combine a plurality of reactions, or to carry out only a mixing treatment in the liquid channel device 110. Namely, no reaction may be carried out. Thus, there is no limitation on the method of use of the liquid channel device 110, 110A, 110B.

In order to promote these various reactions and promote flow of the liquid, these treatments can be carried out in the liquid channel 112 or the liquid chambers. For example, chemical treatments using acid or alkali, physical treatments using latex or fluorescent substances, and biochemical treatments using antigens, antibodies, DNA or the like, can be carried out to obtain such surface treatment effects as hydrophilic, lipophilic and water repellency treatments. In addition, it is also acceptable to carry out pigment coating treatments, plasma treatments, frame treatments and the like. Further, it is acceptable to provide a baffle plate, stirring plate or projections, or to form a hydrolyzing profile, as necessary to the liquid channel 112, to create a uniform mixing state for the flowing liquid. Further, the inside of the liquid channel 112 or the chambers may be pressurized or subjected to reduced pressure (vacuum treatment).

Further, colorants, pigments, fluorescent agents and the like may be introduced to the suitable liquid chamber, enabling the sample which reaches the chamber to be colored, or fluorescence to be added to the sample.

It is also acceptable to directly print the liquid chamber name ("metering chamber" for example), the order or details of the procedure which is carried out using these liquid chamber devices 110, 110A, 110B, etc. as needed to optional sites on the base plates 111, 111A, 111B, liquid chambers, liquid channel 112, or cover plates 113, 113A of the liquid channel device 110, 110A, 110B. Alternatively, a display seal printed with the order or details of the procedure, chamber name, etc. may be adhered or a marking with any kind of symbol may be provided. It is also acceptable to render a portion of the cover plate 113, 113A transparent, so that area stands out.

A conventionally known optical or electrical means may be employed as the detecting and analyzing section for the measured liquid that is formulated in the liquid channel devices 110, 110A, 110B. In this case, the liquid channel devices 110, 110A, 110B may be heated or cooled as necessary.

EXPLANATION OF SYMBOLS 10A, 10B liquid channel device
11A, 11B base plate
11e outer layer
11f middle layer
11g inner layer
12 liquid channel
12a channel formation surface
13 cover plate
13a first base layer
13b strongly adhered layer
13c second base layer
13d weakly adhered layer
14c metering chamber
15 first convex section
15a top part of first convex section
16 second convex section
16a top part of second convex section
17 spacer
18 dam plate
S1~S14 opening section
T1~T2 closing section
P1~P5, P1' liquid transport section
G1~G6 reverse flow check
110, 110A, 110B liquid channel device
111, 111A, 111B base plate
111a, 141a outer layer of base plate
111b middle layer of base plate
111c, 141d inner layer of base plate
141b middle layer on outside of base plate
141c middle layer on inside of base plate
112 liquid channel
112a channel formation surface
113, 113A cover plate
113a outer layer of cover plate
113b inner layer of cover plate
S11~S17 opening section
T11 closing section
115, 150 stopper
116 sealing material supply chamber
130 sealing material
151, 152 concave section

The invention claimed is:

1. A liquid channel device including a base plate in which a liquid channel through which a liquid flows and one or more liquid chambers for holding the liquid are formed to at least one surface thereof, and a cover plate which is laminated to the channel formation surface in which the liquid channel and the liquid chambers of the base plate are formed;
   wherein the liquid channel device further includes an opening section for opening a portion of the liquid channel from a closed mode;
   the opening section includes a stopper which is disposed to a portion of the liquid channel, and undergoes plastic deformation by means of external pressing on the cover plate or a floor of the liquid channel, thereby placing the liquid channel in an open mode, and
   the stopper is formed by coating a stopper forming material for forming the stopper to a portion of the liquid channel, and the stopper forming material includes hollow beads which are deformed and broken by subjecting to pressing.

2. The liquid channel device according to claim 1, wherein a portion of the cover plate or the floor of the liquid channel that is in contact with the stopper is subjected to a releasing treatment.

3. A method for producing the liquid channel device according to claim 1 or 2, including:
- a first step of forming the liquid chambers and the liquid channel to the base plate;
- a second step of forming the stopper to a portion of the liquid channel by coating a stopper forming material for forming the stopper to a portion of the liquid channel, the stopper forming material includes hollow beads which are deformed and broken by subjecting to pressing;
- a third step of laminating the cover plate to the channel formation surface of the base plate; and
- in the first step, a top part of the liquid chambers and the liquid channel are formed to a sheet which forms an inner layer of the base plate, and a bottom part of the liquid chambers is formed to a sheet which forms a middle layer of the base plate, after which the sheet forming the inner layer, the sheet forming the middle layer and a sheet forming an outer layer of the base plate are laminated sequentially.

* * * * *